United States Patent
Oh et al.

(10) Patent No.: US 9,884,874 B2
(45) Date of Patent: Feb. 6, 2018

(54) BROMODOMAIN-INHIBITING COMPOUNDS AND PHARMACEUTICAL COMPOSITION COMPRISING SAME FOR PREVENTING OR TREATING A CANCER

(71) Applicant: KAINOS MEDICINE, INC., Gyeonggi-do (KR)

(72) Inventors: Su-Sung Oh, Seoul (KR); Minjeong Choi, Gyeonggi-do (KR)

(73) Assignee: KAINOS MEDICINE, INC., Gyeonggi-Do (KR)

( * ) Notice: Subject to any disclaimer, the term of this patent is extended or adjusted under 35 U.S.C. 154(b) by 0 days.

(21) Appl. No.: 15/129,657

(22) PCT Filed: Apr. 8, 2015

(86) PCT No.: PCT/KR2015/003530
§ 371 (c)(1),
(2) Date: Sep. 27, 2016

(87) PCT Pub. No.: WO2015/156601
PCT Pub. Date: Oct. 15, 2015

(65) Prior Publication Data
US 2017/0174702 A1 Jun. 22, 2017

Related U.S. Application Data

(60) Provisional application No. 61/977,370, filed on Apr. 9, 2014.

(51) Int. Cl.
| | |
|---|---|
| *A61K 31/551* | (2006.01) |
| *C07D 495/14* | (2006.01) |
| *C07D 487/04* | (2006.01) |
| *A61K 45/06* | (2006.01) |
| *A61K 31/5517* | (2006.01) |

(52) U.S. Cl.
CPC .......... *C07D 495/14* (2013.01); *A61K 31/551* (2013.01); *A61K 31/5517* (2013.01); *A61K 45/06* (2013.01); *C07D 487/04* (2013.01)

(58) Field of Classification Search
USPC ......................... 514/215, 219, 221
See application file for complete search history.

(56) References Cited

U.S. PATENT DOCUMENTS

| | | | |
|---|---|---|---|
| 5,593,988 A * | 1/1997 | Tahara ................. | C07D 487/04 514/210.21 |
| 5,712,274 A | 1/1998 | Sueoka et al. ............... | 514/219 |
| 2010/0286157 A1 | 11/2010 | Miyoshi et al. ............... | 514/220 |
| 2012/0220573 A1 | 8/2012 | Gosmini et al. ............... | 514/220 |
| 2013/0252331 A1 | 9/2013 | Bradner et al. ............... | 435/375 |

FOREIGN PATENT DOCUMENTS

| | | | |
|---|---|---|---|
| CN | 103119160 A | 11/2012 | .......... C07D 487/04 |
| CN | 102781943 A | 5/2013 | .......... C12N 15/09 |
| WO | WO 2011/054844 A1 | 5/2011 | .......... C07D 487/04 |
| WO | WO 2011/143669 A2 | 11/2011 | .......... C07D 487/14 |
| WO | WO 2013-033268 | 3/2013 | .......... C07D 487/04 |

OTHER PUBLICATIONS

Hester, J.B. Jr., et al., (1980). "8-Chloro-1-methyl-6-phenyl-4H-s-triazolo[4,3-a][1.4]benzodiazepines with substituents at C-4". *J. Med. Chem.*, 23:643-647.

International Search Report (ISR) dated Mar. 20, 2015 in PCT/KR2015/003530 published as WO 2015/156601 with English Translation.

Written Opinion of the International Searching Authority dated Jul. 21, 2015 in PCT/KR2015/003530.

Extended European Search Report dated Jul. 25, 2017, issued in European Patent Application No. 15776821.9.

Chinese Office Action from corresponding Chinese Application No. 201580016461.0 dated Jun. 2, 2017.

* cited by examiner

*Primary Examiner* — Pancham Bakshi
(74) *Attorney, Agent, or Firm* — Harness, Dickey & Pierce, P.L.C.

(57) ABSTRACT

Provided is a novel compound having bromodomain and extra terminal domain (BET) protein inhibiting activities, and a pharmaceutical composition comprising the same which can be useful for prevention or treatment of precancerous transformation or cancer.

8 Claims, 4 Drawing Sheets

BROMODOMAIN-INHIBITING COMPOUNDS AND PHARMACEUTICAL COMPOSITION COMPRISING SAME FOR PREVENTING OR TREATING A CANCER

CROSS-REFERENCE TO RELATED APPLICATIONS

This application is a national phase application of PCT Application No. PCT/KR2015/003530, filed on Apr. 8, 2015, which claims the benefit and priority of U.S. Provisional Application No. 61/977,370, filed Apr. 9, 2014. The entire disclosures of the applications identified in this paragraph are incorporated herein by reference.

FIELD OF THE INVENTION

The present invention relates to a compound inhibiting the bromodomain and extra terminal domain (BET) proteins; a method of preparation thereof; a pharmaceutical composition comprising the same; and a method for preventing or treating precancerous transformation or cancer using the compound.

BACKGROUND OF THE INVENTION

Gene expression is regulated by a variety of different mechanisms at several different levels. Epigenetic mechanisms regulate gene expression by modifying DNA without changing nucleotide sequences or modifying histones that wrap the DNA molecules and restrict access of DNA binding proteins such as transcription factors. Histone modifications include acetylation, methylation, phosphorylation, ubiquitinylation, and a few others. These modifications are called 'writing' and the enzymes responsible for the "writing" are called "writers". And these histone modifications are reversible, and the enzymes that carry out the reverse mechanisms, such as histone deacetylases and histone demethylases, are called "erasers".

These epigenetic modifications are typically recognized by so called "readers", leading to activating or silencing the gene expression depending on specific chromatin context of each writing-reading combination. Bromodomain (BRD)-containing proteins bind to the acetylated histones through the BRDs, which are about 110 amino acids long in length (P. Filippakopoulos, et al., Cell, 2012, 149:214-231). This highly conserved bromodomain, comprised of four antiparallel alpha-helices and two connecting loops, is found in a number of different classes of proteins including histone acetylases, eukaryotic transcription factors and co-regulators, DNA helicases, chromatin-remodeling complexes and others.

Bromodomain and extra terminal domain (BET) proteins are a subfamily of bromodomain-containing proteins that have two bromodomains and one extra-terminal domain (ET). The subfamily is comprised of 4 members including BRD2, BRD3, BRD4, and BRDT (BRD5). BET proteins play an important role in several transcriptional programs, and implicate in aberrant transcriptional events that are responsible for several types of human diseases including inflammation and cancer (A. C. Belkina, et al., Nature Reviews Cancer, 2012, 12 (7):465-477; and R. K. Prinjha, et al., Trends in Pharmacological Sciences, 2012, 33:146-153). Deregulated expression of BRD2, BRD3 and BRD4 is oncogenic in humans. Reciprocal chromosomal translocations between human BRD3 (9q34.2) or BRD4 (19p13.1) genes and the NUT gene (15q14) produce a fused oncoprotein causing an NUT midline carcinoma (NMC), and an aggressive cancer with high mortality (C. A. French, et al., Cancer Research, 2003, 63(2):304-307; and C. A. French, et al., Oncogene, 2008, 27:2237-2242). BRD4 is often up-regulated in melanoma (M. F. Segura, et al., Cancer Research, 2013, 73(20):6264-6276).

Numerous small-molecule inhibitors of BET proteins have been developed which prevent binding of BRD to acetylated histones (S. Muller et al., Med Chem Comm, 2014, 5:288-296). Most of these compounds are acetylated-lysine mimics, and show strong anti-tumor activity against hematological cancers and solid cancers such as mixed lineage leukemia (MLL)-fusion leukemia (Dawson M A et al., Nature, 2011, 478:529-533), multiple myeloma (J. E. Delmore et al., Cell, 2011, 146:904-917, and Aristeidis Chaidos et al., Blood 2014, 123:697-705), glioblastoma (Zhixiang C. et al., Clinical cancer research, 2013, 19:1748-1759), neuroblastoma (J. A. Mertz et al., Cancer Discovery 2013, 3:308-323), prostate cancer (A. Wyce et al., Oncotarget 2013, 4:2419-2429), lung cancer (Shimamura T. et al., Clinical cancer research, 2013, 19:6183-6192), melanoma (M. F. Segura, et al., Cancer Research 2013, 73(20):6264-6276), and autoimmune diseases. Notably, BRD inhibitors inhibited the expression of the oncogene c-myc, which had a critical effect on cell proliferation in many different types of cancers. Therefore, BRD inhibitors or BET protein inhibitors potentially represent a new class of therapeutics to prevent or treat precancerous transformation or a cancer.

SUMMARY OF THE INVENTION

Accordingly, it is an object of the present invention to provide novel compounds that selectively inhibit bromodomain-containing proteins such as BRD2, BRD3 and BRD4.

It is another object of the present invention to provide a pharmaceutical composition comprising said compound as an active ingredient.

It is a further object of the present invention to provide a method for preventing or treating precancerous transformation or a cancer using the compounds.

In accordance with one aspect of the present invention, there is provided a compound of formula (I), or a pharmaceutically acceptable salt, a hydrate, a solvate, or an isomer thereof:

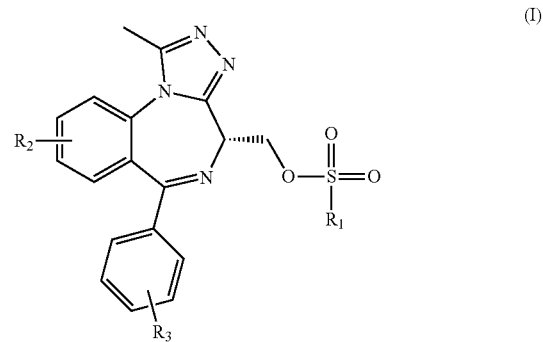

(I)

wherein, $R_1$ is selected from the group consisting of hydrogen, $C_{1-10}$ alkyl, $C_{1-10}$ alkylaryl, $C_{3-10}$ cycloalkyl, $C_{3-10}$ cycloalkyl$C_{1-10}$ alkyl, $C_{1-10}$ alkyl$C_{3-10}$ cycloalkyl, formyl, heterocyclyl, heterocyclyl$C_{1-10}$ alkyl, halo$C_{1-10}$ alkyl, heteroaryl, aralkyl, heteroaryl$C_{1-10}$ alkyl, heteroarylaryl, fused bicyclyl, biaryl, aryloxyaryl, heteroaryloxyaryl, aryloxyheteroaryl, heteroaryloxyheteroaryl, $C_{2-10}$ alkenyl, $C_{2-10}$ alkynyl, azido, nitro, cyano, ORa, NRbRb' and CORc, wherein, Ra, Rb, Rb' and Rc are each independently selected from the group consisting of hydrogen, $C_{1-10}$ alkyl, $C_{1-10}$ alkylaryl, $C_{3-10}$ cycloalkyl, $C_{3-10}$ cycloalkyl$C_{1-10}$ alkyl, $C_{1-10}$ alkylcycloalkyl, formyl, heterocyclyl, heterocyclylalkyl, halo$C_{1-10}$ alkyl, heteroaryl, aralkyl, heteroaryl $C_{1-10}$ alkyl, heteroarylaryl, fused bicyclyl, biaryl, aryloxyaryl, heteroaryloxyaryl, aryloxyheteroaryl, heteroaryloxyheteroaryl, $C_{2-10}$ alkenyl, $C_{2-10}$ alkynyl, azido, nitro and cyano;

$R_2$ is selected from the group consisting of hydrogen, hydroxyl, halo, $C_{1-6}$ alkyl, halo $C_{1-6}$ alkyl, $C_{1-6}$ alkoxy, halo $C_{1-6}$ alkoxy, nitro, cyano, $CF_3$, —$OCF_3$, —COORd, —CONHRd, and heteroaromatic groups selected from the group consisting

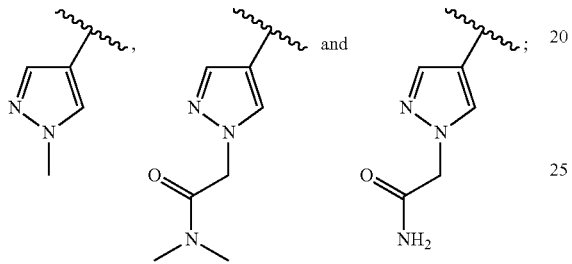

$R_3$ is selected from the group consisting of hydrogen, hydroxyl, halo, $C_{1-6}$ alkyl, halo $C_{1-6}$ alkyl, $C_{1-6}$ alkoxy, halo $C_{1-6}$ alkoxy, nitro, cyano, $CF_3$, —$OCF_3$, —COORd and —CONHRd; and Rd is $C_{1-3}$ alkyl or hydroxy $C_{1-3}$ alkyl.

Also, there is provided a compound of formula (II), or a pharmaceutically acceptable salt, a hydrate, a solvate, or an isomer thereof:

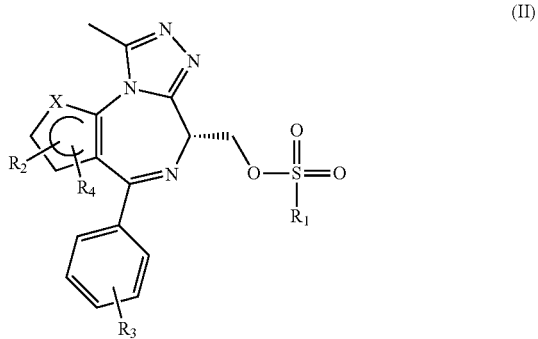

(II)

wherein,
X is C or S;

$R_1$ is selected from the group consisting of hydrogen, $C_{1-10}$ alkyl, $C_{1-10}$ alkylaryl, $C_{3-10}$ cycloalkyl, $C_{3-10}$ cycloalkyl$C_{1-10}$ alkyl, $C_{1-10}$ alkyl$C_{3-10}$ cycloalkyl, formyl, heterocyclyl, heterocyclyl$C_{1-10}$ alkyl, halo$C_{1-10}$ alkyl, heteroaryl, aralkyl, heteroaryl$C_{1-10}$ alkyl, heteroarylaryl, fused bicyclyl, biaryl, aryloxyaryl, heteroaryloxyaryl, aryloxyheteroaryl, heteroaryloxyheteroaryl, $C_{2-10}$ alkenyl, $C_{2-10}$ alkynyl, azido, nitro, cyano, ORa, NRbRb' and CORc, wherein, Ra, Rb, Rb' and Rc are each independently selected from the group consisting of hydrogen, $C_{1-10}$ alkyl, $C_{1-10}$ alkylaryl, $C_{3-10}$ cycloalkyl, $C_{3-10}$ cycloalkyl$C_{1-10}$ alkyl, $C_{1-10}$ alkylcycloalkyl, formyl, heterocyclyl, heterocyclylalkyl, halo$C_{1-10}$ alkyl, heteroaryl, aralkyl, heteroaryl $C_{1-10}$ alkyl, heteroarylaryl, fused bicyclyl, biaryl, aryloxyaryl, heteroaryloxyaryl, aryloxyheteroaryl, heteroaryloxyheteroaryl, $C_{2-10}$ alkenyl, $C_{2-10}$ alkynyl, azido, nitro and cyano;

$R_2$ and $R_4$ are each independently selected from the group consisting of hydrogen, hydroxyl, halo, $C_{1-6}$ alkyl, halo $C_{1-6}$ alkyl, $C_{1-6}$ alkoxy, halo $C_{1-6}$ alkoxy, nitro, cyano, $CF_3$, —$OCF_3$, —COORd, —CONHRd, and heteroaromatic groups selected from the group consisting of:

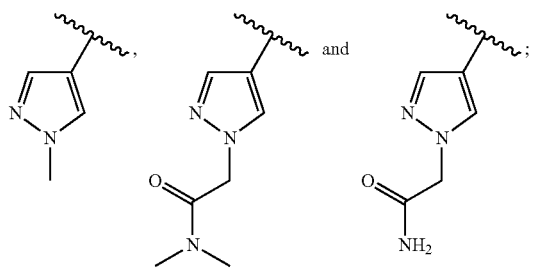

$R_3$ is selected from the group consisting of hydrogen, hydroxyl, halo, $C_{1-6}$ alkyl, halo $C_{1-6}$ alkyl, $C_{1-6}$ alkoxy, halo $C_{1-6}$ alkoxy, nitro, cyano, $CF_3$, —$OCF_3$, —COORd and —CONHRd; and Rd is $C_{1-3}$ alkyl or hydroxy $C_{1-3}$ alkyl.

In accordance with another aspect of the present invention, there is provided a pharmaceutical composition for preventing or treating precancerous transformation or a cancer, which comprises the compound of formula (I) or (II), or a pharmaceutically acceptable salt, a hydrate, a solvate or an isomer thereof as an active ingredient, and a pharmaceutically acceptable carrier.

In accordance with a further aspect of the present invention, there is provided a method for preventing or treating precancerous transformation or a cancer in a mammal, which comprises administering the compound of formula (I) or (II), or a pharmaceutically acceptable salt, a hydrate, a solvate, or an isomer thereof to the mammal in need thereof.

In accordance with a still further aspect of the present invention, there is provided a use of the compound of formula (I) or (II), or a pharmaceutically acceptable salt, a hydrate, a solvate, or an isomer thereof for the manufacture of a medicament for preventing or treating precancerous transformation or a cancer.

The compounds of the present invention may be more potent, more metabolically stable and more effective in cancer treatment than other bromodomain inhibitors that do not have the sulfonate derivatives and sulfamate derivatives.

Further, the compounds of the present invention may exhibit excellent in vivo pharmacological and pharmacokinetical properties.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
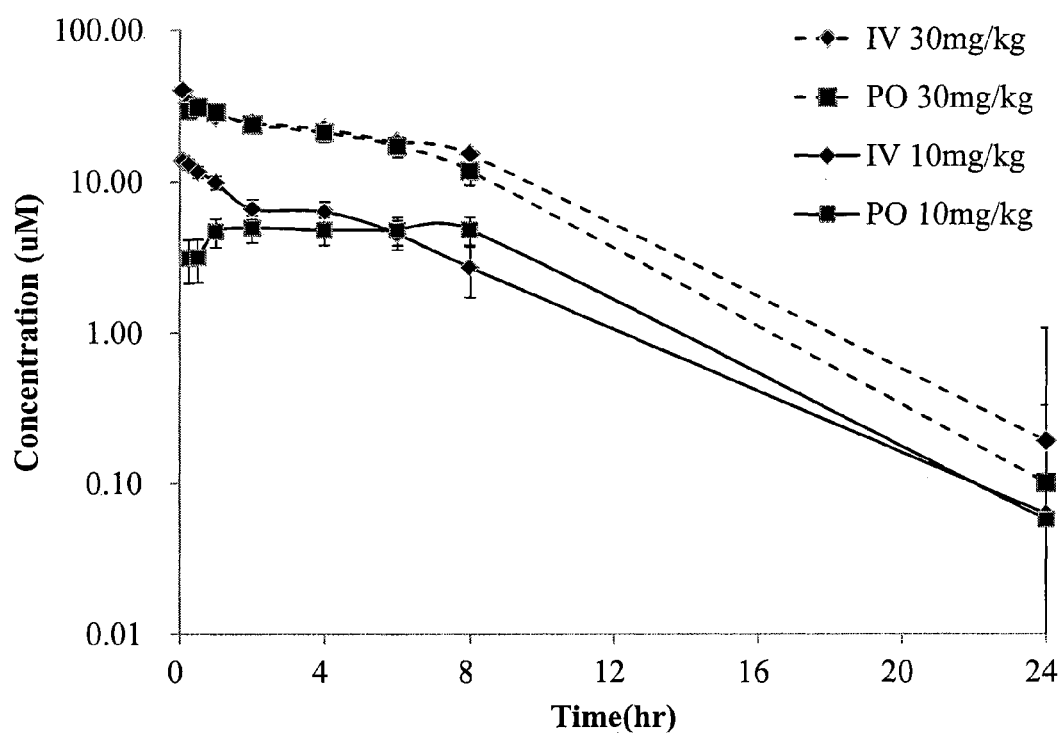
FIG. 1: Pharmacokinetics of Compound 1 in mouse through PO administration route.

While the terms used in the description of the invention are believed to be well understood by one of ordinary skill in the art, definitions, where provided herein, are set forth to facilitate description of the invention, and to provide illustrative examples for use of the terms.

The term "alkyl" is used herein to refer to a hydrocarbon containing normal, secondary, tertiary, or cyclic carbon atoms (e.g., linear saturated aliphatic hydrocarbon groups, branched saturated aliphatic hydrocarbon groups, or a saturated or unsaturated non-aromatic hydrocarbon mono or multi-ring system (e.g., cycloalkyl)). When the term "alkyl" is used without reference to a number of carbon atoms, it is to be understood to refer to a $C_{1-10}$ alkyl.

The term "aryl" is used herein to refer to cyclic, aromatic hydrocarbon groups which have 1 to 3 aromatic rings. The aryl group may have fused thereto a second or third ring which is a heterocyclo, cycloalkyl, or heteroaryl ring, provided in that case the point of attachment will be to the aryl portion of the ring system. Examples of "aryl" groups include, but are not limited to, phenyl, naphthyl, tetrahydronaphthyl, biphenyl, indanyl, anthracyl or phenanthryl, as well as substituted derivatives thereof.

The term "heteroaryl" is used herein to refer to an aryl group in which at least one of the carbon atoms in the aromatic ring has been replaced by a heteroatom selected from oxygen, nitrogen and sulfur. The nitrogen and/or sulfur heteroatoms may optionally be oxidized and the nitrogen heteroatoms may optionally be quaternized. The heteroaryl group may be a 5- to 6-membered monocyclic, 7- to 11-membered bicyclic, or 10- to 16-membered tricyclic ring system.

The term "alkenyl" is used herein to refer to a straight or branched chain hydrocarbon containing from 2 to 10 carbon atoms and containing at least one carbon-carbon double bond formed by the removal of two hydrogens.

The term "alkynyl" is used herein to refer to a straight or branched chain hydrocarbon containing from 2 to 10 carbon atoms and containing at least one carbon-carbon triple bond.

The term "alkoxy" is used herein to refer to an alkyl group, as defined herein, appended to the parent molecular moiety through an oxygen atom.

The term "aralkyl" is used herein to refer to an aryl-alkyl group in which the aryl and alkyl are as defined herein. Preferred aralkyls comprise a lower alkyl group.

The term "aryloxy" is used herein to refer to an aryl group, as defined herein, appended to the parent molecular moiety through an oxygen atom.

The term "carbocyclyl" (alone or in combination with another term(s)) is used herein to refer to a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" being the atoms bound together to form the ring or rings of a cyclic substituent). A carbocyclyl may be a single ring, which typically contains from 3 to 6 ring atoms.

The term "cycloalkyl" is used herein to refer to monocyclic or multicyclic (e.g., bicyclic, tricyclic, etc.) hydrocarbons containing from 3 to 12 carbon atoms that is completely saturated or has one or more unsaturated bonds but does not amount to an aromatic group.

The term "cyano" is used herein to refer to a —CN group.

The term "halo" or "halogen" is used herein to refer to —Cl, —Br, —I, or —F.

The term "haloalkyl" is used herein to refer to an alkyl, as defined herein, wherein at least one hydrogen atom is replaced with halogen atoms.

The term "heterocyclyl" is used herein to include a saturated (e.g., "heterocycloalkyl"), partially unsaturated (e.g., "heterocycloalkenyl" or "hetercycloalkynyl") or completely unsaturated (e.g., "heteroaryl") ring system, which have 3 to 12 atoms including at least one heteroatom, such as nitrogen, oxygen, or sulfur.

The terms "first" and "second" are used herein for the purpose of distinguishing between two compounds, or between two compositions, as will be clearer from the description.

The phrase "medically effective amount" means an amount of a composition or compound that treats the particular disease, condition or disorder; ameliorates, relieves, or decreases one or more symptoms associated with the particular disease, condition or disorder; and/or delays or prevents the onset of symptoms of, or a pathological process associated with the particular disease, condition or disorder described herein in more detail.

The term "pharmaceutically acceptable carrier" is used herein to mean any compound or composition or carrier medium useful in any one or more of administration, delivery, storage, stability of a composition or compound described herein.

The pharmaceutically acceptable carriers include, but are not limited to, a diluent, water, saline, a suitable vehicle (e.g., liposome, microparticle, nanoparticle, emulsion, and capsule), a buffer, a medical parenteral vehicle, an excipient, an aqueous solution, a suspension, a solvent, an emulsion, a detergent, a chelating agent, a solubilizing agent, a salt, a colorant, a polymer, a hydrogel, a surfactant, an emulsifier, an adjuvant, a filler, a preservative, a stabilizer, an oil, a binder, a disintegrant, an absorbant, a flavor agent, and the like as broadly known in the art.

Hereinafter, the present invention is described in detail.

The present invention provides a compound of formula (I), or a pharmaceutically acceptable salt, a hydrate, a solvate, or an isomer thereof:

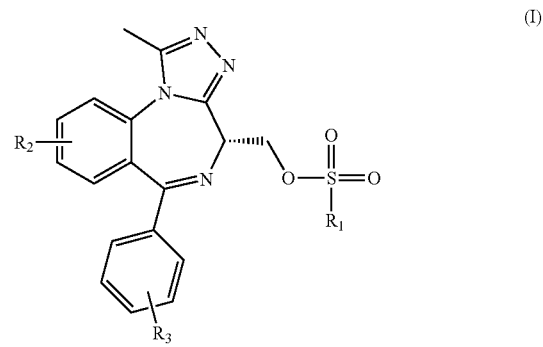

(I)

wherein, $R_1$ is selected from the group consisting of hydrogen, $C_{1-10}$ alkyl, $C_{1-10}$ alkylaryl, $C_{3-10}$ cycloalkyl, $C_{3-10}$ cycloalkyl$C_{1-10}$ alkyl, $C_{1-10}$ alkyl$C_{3-10}$ cycloalkyl, formyl, heterocyclyl, heterocyclyl$C_{1-10}$ alkyl, halo$C_{1-10}$ alkyl, heteroaryl, aralkyl, heteroaryl$C_{1-10}$ alkyl, heteroarylaryl, fused bicyclyl, biaryl, aryloxyaryl, heteroaryloxyaryl, aryloxyheteroaryl, heteroaryloxyheteroaryl, $C_{2-10}$ alkenyl, $C_{2-10}$ alkynyl, azido, nitro, cyano, ORa, NRbRb' and CORc, wherein, Ra, Rb, Rb' and Rc are each independently selected from the group consisting of hydrogen, $C_{1-10}$ alkyl, $C_{1-10}$ alkylaryl, $C_{3-10}$ cycloalkyl, $C_{3-10}$ cycloalkyl$C_{1-10}$ alkyl, $C_{1-10}$ alkylcycloalkyl, formyl, heterocyclyl, heterocyclylalkyl, halo$C_{1-10}$ alkyl, heteroaryl, aralkyl, heteroaryl $C_{1-10}$ alkyl, heteroarylaryl, fused bicyclyl, biaryl, aryloxyaryl, heteroaryloxyaryl, aryloxyheteroaryl, heteroaryloxyheteroaryl, $C_{2-10}$ alkenyl, $C_{2-10}$ alkynyl, azido, nitro and cyano;

$R_2$ is selected from the group consisting of hydrogen, hydroxyl, halo, $C_{1-6}$ alkyl, halo $C_{1-6}$ alkyl, $C_{1-6}$ alkoxy, halo $C_{1-6}$ alkoxy, nitro, cyano, $CF_3$, —$OCF_3$, —COORd, —CONHRd, and heteroaromatic groups selected from the group consisting of:

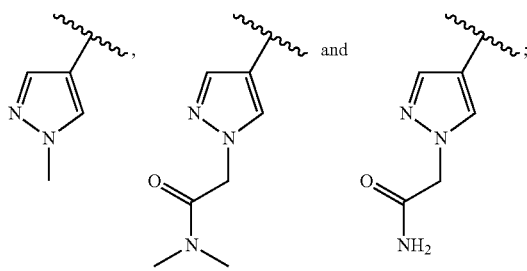

$R_3$ is selected from the group consisting of hydrogen, hydroxyl, halo, $C_{1-6}$ alkyl, halo $C_{1-6}$ alkyl, $C_{1-6}$ alkoxy, halo $C_{1-6}$ alkoxy, nitro, cyano, $CF_3$, —$OCF_3$, —COORd and —CONHRd; and Rd is $C_{1-3}$ alkyl or hydroxy $C_{1-3}$ alkyl.

Preferably, $R_1$ is $C_{1-6}$ alkyl, $C_{3-10}$ cycloalkyl, aralkyl or NRbRb', wherein Rb and Rb' are each independently hydrogen or $C_{1-6}$ alkyl; and $R_2$ is hydrogen, $C_{1-6}$ alkoxy, —CONHRd or heteroaromatic groups selected from the group consisting of:

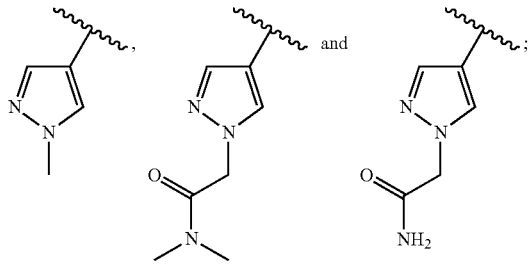

$R_3$ is halo; and

Rd is $C_{1-3}$ alkyl or hydroxy $C_{1-3}$ alkyl.

Also, the present invention provides a compound of formula (II), or a pharmaceutically acceptable salt, a hydrate, a solvate, or an isomer thereof:

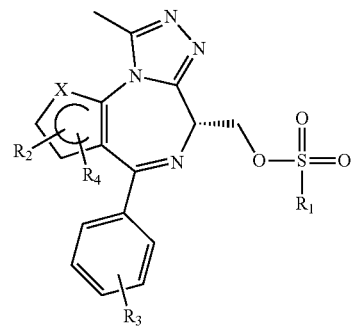

(II)

wherein,

X is C or S;

$R_1$ is selected from the group consisting of hydrogen, $C_{1-10}$ alkyl, $C_{1-10}$ alkylaryl, $C_{3-10}$ cycloalkyl, $C_{3-10}$ cycloalkyl$C_{1-10}$ alkyl, $C_{1-10}$ alkyl$C_{3-10}$ cycloalkyl, formyl, heterocyclyl, heterocyclyl$C_{1-10}$ alkyl, halo$C_{1-10}$ alkyl, heteroaryl, aralkyl, heteroaryl$C_{1-10}$ alkyl, heteroarylaryl, fused bicyclyl, biaryl, aryloxyaryl, heteroaryloxyaryl, aryloxyheteroaryl, heteroaryloxyheteroaryl, $C_{2-10}$ alkenyl, $C_{2-10}$ alkynyl, azido, nitro, cyano, ORa, NRbRb' and CORc, wherein, Ra, Rb, Rb' and Rc are each independently selected from the group consisting of hydrogen, $C_{1-10}$ alkyl, $C_{1-10}$ alkylaryl, $C_{3-10}$ cycloalkyl, $C_{3-10}$ cycloalkyl$C_{1-10}$ alkyl, $C_{1-10}$ alkylcycloalkyl, formyl, heterocyclyl, heterocyclylalkyl, halo$C_{1-10}$ alkyl, heteroaryl, aralkyl, heteroaryl $C_{1-10}$ alkyl, heteroarylaryl, fused bicyclyl, biaryl, aryloxyaryl, heteroaryloxyaryl, aryloxyheteroaryl, heteroaryloxyheteroaryl, $C_{2-10}$ alkenyl, $C_{2-10}$ alkynyl, azido, nitro and cyano;

$R_2$ and $R_4$ are each independently selected from the group consisting of hydrogen, hydroxyl, halo, $C_{1-6}$ alkyl, halo $C_{1-6}$ alkyl, $C_{1-6}$ alkoxy, halo $C_{1-6}$ alkoxy, nitro, cyano, $CF_3$, —$OCF_3$, —COORd, —CONHRd, and heteroaromatic groups selected from the group consisting of:

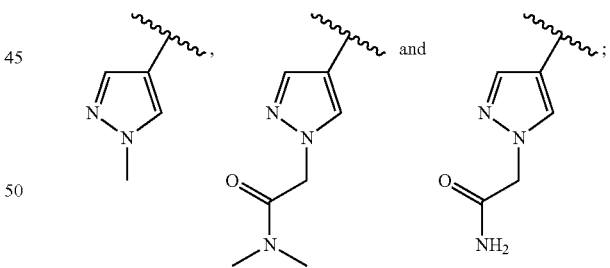

$R_3$ is selected from the group consisting of hydrogen, hydroxyl, halo, $C_{1-6}$ alkyl, halo $C_{1-6}$ alkyl, $C_{1-6}$ alkoxy, halo $C_{1-6}$ alkoxy, nitro, cyano, $CF_3$, —$OCF_3$, —COORd and —CONHRd; and Rd is $C_{1-3}$ alkyl or hydroxy $C_{1-3}$ alkyl.

Preferably, X is S;

$R_1$ is $C_{1-6}$ alkyl or NRbRb', wherein Rb and Rb' are each independently hydrogen or $C_{1-6}$ alkyl;

$R_2$ and $R_4$ are each independently hydrogen or $C_{1-6}$ alkyl; and $R_3$ is halo.

Examples of more preferred compound according to the present invention are:

(R)-(6-(4-chlorophenyl)-8-methoxy-1-methyl-4H-benzo[f] [1,2,4]triazolo[4,3-a][1,4]diazepin-4-yl)methyl methanesulfonate;

(R)-(6-(4-chlorophenyl)-8-methoxy-1-methyl-4H-benzo[f] [1,2,4]triazolo[4,3-a][1,4]diazepin-4-yl)methyl ethanesulfonate;

(R)-(6-(4-chlorophenyl)-8-methoxy-1-methyl-4H-benzo[f] [1,2,4]triazolo[4,3-a][1,4]diazepin-4-yl)methyl propane-1-sulfonate;

(R)-(6-(4-chlorophenyl)-8-methoxy-1-methyl-4H-benzo[f] [1,2,4]triazolo[4,3-a][1,4]diazepin-4-yl)methyl cyclopropanesulfonate;

(R)-(6-(4-chlorophenyl)-8-methoxy-1-methyl-4H-benzo[f] [1,2,4]triazolo[4,3-a][1,4]diazepin-4-yl)methyl benzenesulfonate;

(R)-(6-(4-chlorophenyl)-1-methyl-4H-benzo[f][1,2,4]triazolo[4,3-a][1,4]diazepin-4-yl)methyl methanesulfonate;

(R)-(6-(4-cyanophenyl)-8-methoxy-1-methyl-4H-benzo[f] [1,2,4]triazolo[4,3-a][1,4]diazepin-4-yl)methyl methanesulfonate;

(R)-(6-(4-chlorophenyl)-8-methoxy-1-methyl-4H-benzo[f] [1,2,4]triazolo[4,3-a][1,4]diazepin-4-yl)methyl sulfamate;

(R)-(6-(4-chlorophenyl)-8-methoxy-1-methyl-4H-benzo[f] [1,2,4]triazolo[4,3-a][1,4]diazepin-4-yl)methyl dimethylsulfamate;

(R)-(6-(4-chlorophenyl)-8-methoxy-1-methyl-4H-benzo[f] [1,2,4]triazolo[4,3-a][1,4]diazepin-4-yl)methyl methylsulfamate;

(R)-(6-(4-chlorophenyl)-1-methyl-8-(1-methyl-1H-pyrazol-4-yl)-4H-benzo[f][1,2,4]triazolo[4,3-a][1,4]diazepin-4-yl)methyl methanesulfonate;

(R)-(8-(1-(2-amino-2-oxoethyl)-1H-pyrazol-4-yl)-6-(4-chlorophenyl)-1-methyl-4H-benzo[f][1,2,4]triazolo[4,3-a][1,4]diazepin-4-yl)methyl methanesulfonate;

(R)-(6-(4-chlorophenyl)-8-(1-(2-(dimethylamino)-2-oxoethyl)-1H-pyrazol-4-yl)-1-methyl-4H-benzo[f][1,2,4]triazolo[4,3-a][1,4]diazepin-4-yl)methyl methanesulfonate;

(R)-(6-(4-chlorophenyl)-8-((2-hydroxyethyl)carbamoyl)-1-methyl-4H-benzo[f][1,2,4]triazolo[4,3-a][1,4]diazepin-4-yl)methyl methanesulfonate;

(R)-(4-(4-chlorophenyl)-2,3,9-trimethyl-6H-thieno[3,2-f][1,2,4]triazolo[4,3-a][1,4]diazepin-6-yl)methyl methanesulfonate;

(R)-(4-(4-chlorophenyl)-2,3,9-trimethyl-6H-thieno[3,2-f][1,2,4]triazolo[4,3-a][1,4]diazepin-6-yl)methyl sulfamate;

(R)-(4-(4-chlorophenyl)-2,3,9-trimethyl-6H-thieno[3,2-f][1,2,4]triazolo[4,3-a][1,4]diazepin-6-yl)methyl dimethylsulfamate; and (R)-(4-(4-chlorophenyl)-2,3,9-trimethyl-6H-thieno[3,2-f][1,2,4]triazolo[4,3-a][1,4]diazepin-6-yl)methyl methylsulfamate.

The compounds of the present invention comprise sulfonate derivatives and sulfamate derivatives that selectively inhibit BRD-containing proteins such as BRD2, BRD3 and BRD4.

The compounds of the present invention were evaluated for in vitro potency using the BRD binding and cancer cell anti-proliferative activity assay. In vivo efficacy of the compounds has been confirmed by using cancer-induced animal models. The compounds of the present invention exhibited a significant inhibition of BRD binding activity to acetylated histone peptides, and excellent pharmacokinetic properties in mouse, rat and dog.

The compounds of the present invention may be used in vitro or in vivo to inhibit growth of a cancer cell; or in vitro or in vivo to treat a mammal in need thereof.

The compounds of formula (I) or (II) can form salts, and salts of the compounds are included within the scope of the invention.

The terms "salt" or "pharmaceutically acceptable salt", as used herein, refer to inorganic or organic salts of a compound. These salts can be prepared, for example, by reacting the compound of formula (I) or (II) with an amount of acid or base, such as an equivalent amount, in a medium such as one in which the salt formed then precipitates, or in an aqueous medium followed by lyophilization. Representative salts include bisulfate, sulfate, benzene sulfonate, camphorsulfonate, laurylsulfonate, methanesulfonate, naphthalenesulfonate, toluenesulfonate, acetate, trifluoroacetate, benzoate, borate, butyrate, citrate, formate, fumarate, hydrobromide, hydrochloride, hydroiodide, lactate, laurate, maleate, malonate, mesylate, nitrate, oxalate, phosphate, hexafluorophosphate, propionate, salicylate, stearate, succinate, tartrate, thiocyanate, and the like. The salts may include base salts based on the alkali and alkaline earth metals, such as calcium, sodium, lithium, magnesium, and potassium; or with organic bases such as with organic amines (e.g., dicyclohexylamine, t-butyl amine, methylamine, dimethylamine, triethylamine, ethylamine, procaine, morpholine, N-methylpiperidine, dibenzylamine, and the like); or as an ammonium salt.

The compounds of formula (I) or (II) may exist in a solvated form or unsolvated form. Solvates of the compound of the present invention may be formed in a synthetic process in which the compound becomes physically associated with one or more solvent molecules (e.g., by ionic and/or covalent bonding). Optionally, it may be converted to a solvate by dissolving the compound in desired amounts of a solvent of choice (e.g., organic solvent, water, or mixtures thereof) to form a solution, heating the solution at a temperature higher than ambient temperature, and cooling the solution at a rate sufficient to form crystals of the solvate, which may then be further isolated using methods known in the art. Examples of suitable solvents include methanolates, ethanolates, hydrates (where the solvent molecule is water), and the like.

The compounds of formula (I) or (II) may contain asymmetric or chiral centers, and thus exist in different isomeric forms. All stereoisomers (e.g., geometric isomers, optical isomers, and the like), enantiomeric forms, diastereomeric forms, tautomeric forms and positional isomers of the compounds of the invention are also included within the scope of the invention. A first conformational form of a compound can be separated from a second and different conformational form of the compound by using methods known in the art such as chromatography, crystallization, and methods of synthesis which selectively result in a particular desired conformational form.

Further, the present invention provides a pharmaceutical composition for preventing or treating precancerous transformation or a cancer, which comprises the compound of formula (I) or (II), or a pharmaceutically acceptable salt, a hydrate, a solvate, or an isomer thereof as an active ingredient, and a pharmaceutically acceptable carrier.

The precancerous transformation or a cancer is selected from the group consisting of autoimmune diseases, epithelial tumors, melanoma, leukemia such as acute promyelocytic leukemia, lymphoma, solid or non-lymphoid tumors such as osteogenic sarcoma, colon cancer, pancreatic cancer, breast cancer, prostate cancer, ovarian cancer, brain cancer, cervical cancer, and lung cancer.

The pharmaceutical composition according to the present invention may be administered once, or multiple times, as needed, to deliver a medically effective amount of the composition, e.g., an amount effective to mediate modulation of a disease, disorder, or condition by inhibiting BRD in an individual receiving the composition. For example, a medically effective amount of the pharmaceutical composition comprising the compound of the invention may be an amount that enters into cells which are contacted with the compound, and which results in inhibiting BRD within the cells. Such a medically effective amount of the pharmaceutical composition will depend on such factors as the mode of administration, the formulation for administration, disease to be modulated, the size and health of the individual to receive such a composition, and other factors which can be taken into consideration by a medical practitioner skilled in the art.

An amount of the pharmaceutical composition to be administered may vary from 0.01 milligrams to about 1,000 milligrams, and more typically from about 1 milligram per day to about 200 milligram per day. One skilled in the art can apply known principles and models of drug delivery and pharmacokinetics to ascertain a likely range of dosages to be tested in preclinical and clinical studies for determining a medically effective amount of a compound of the invention.

The pharmaceutically acceptable carrier may be selected from the group consisting of a binder (e.g., syrup, sorbitol, gum, corn starch, gelatin and acacia), a filler (e.g., lactose, sugar, starch and calcium phosphate), an excipient (e.g., dicalcium phosphate), a disintegrating agent (e.g., vegetable starch and alginic acid), a lubricant (e.g., magnesium stearate) and a flavoring agent (e.g., sweetening agent, natural and artificial flavors).

The pharmaceutically acceptable carrier may facilitate one or more of storage, stability, administration, and delivery, of the composition. The carrier may be particulate, so that the composition may be in, for example, a powder or solid form. The carrier may be in a semi-solid, gel, or liquid formula, so that the pharmaceutical composition may be ingested, injected, applied, or otherwise administered. The carrier may be gaseous, so that the pharmaceutical composition may be inhaled.

For oral administration of the pharmaceutical composition containing the compound of the present invention, suitable formulations may be presented in the form of tablets, caplets, capsules, and the like, in which typically the compound of the present invention may be present in a predetermined amount as a powder, granules, solution, or suspension as the sole active ingredient, or in combination with an additional one or more pharmaceutical agents. Such oral formulations may be coated or uncoated to modify their disintegration and/or absorption. Coating may be performed using conventional coating agents and methods known in the art.

The mode of administration of the compound or pharmaceutical composition of the present invention to an individual in need thereof may be any mode known in the art to be suitable for delivering a pharmaceutical composition, and particularly suitable for treating a disease, disorder or condition by inhibiting BRD. The pharmaceutical composition may be administered intravenously, intraperitoneally, orally, subcutaneously, intramuscularly, intranasally, transdermally, by perfusion, and by peristaltic techniques.

The pharmaceutical composition according to the present invention may further comprise at least one additional pharmaceutical agent.

Specifically, the pharmaceutical composition may also be combined with other therapies, such as one or more additional pharmaceutical agents, to treat a disease, disorder or condition, i.e., precancerous transformation or a cancer. Such combination therapy may be administered concurrently, sequentially, or in regimen alternating between the composition of the invention and the other therapy.

In addition, the compounds having BRD inhibition activity of the present invention, when used to treat precancerous transformation or a cancer, may be used in combination with one or more chemotherapeutic agents, with the potential for synergistically enhancing apoptosis and/or growth inhibition of cancer cells by the combination.

Such chemotherapeutic agents include, but are not limited to, LSD1 blockers, peroxisome proliferating-activator receptor (PPAR) ligands (e.g., rosiglitazone); alkylating agents (e.g., nitrogen mustards, such as mechlorethamine, chlorambucil, cyclophosphamide, ifosfamide, and melphalan; nitrosoureas, such as streptozocin, carmustine, and lomustine; alkyl sulfonates, such as busulfan; triazines, such as dacarbazine and temozolomide; ethylenimines, such as thiotepa and altretamine; and platinum-based drugs, such as cisplatin, carboplatin, and oxalaplatin); antimetabolites (e.g., 5-fluorouracil, 6-mercaptopurine, capecitabine, cladribine, clofarabine, cytarabine, floxuridine, fludarabine, gemcitabine, hydroxyurea, methotrexate, pemetrexed, pentostatin, and thioguanine); anti-tumor antibiotics (e.g., anthracyclines, such as daunorubicin, doxorubicin, epirubicin, and idarubicin; and actinomycin-D, bleomycin, mitomycin-C, and mitoxantrone); topoisomerase inhibitors (e.g., topoisomerase I inhibitors such as topotecan and irinotecan; and topoisomerase II inhibitors, such as etoposide, teniposide, and mitoxantrone); mitotic inhibitors (e.g., taxanes, such as paclitaxel and docetaxel; epothilones such as ixabepilone; vinca alkaloids, such as vinblastine, vincristine, and vinorelbine; and estramustine); corticosteroids (e.g., prednisone, methylprednisolone, and dexamethasone); proteosome inhibitors (e.g., bortezomib); targeted therapies (e.g., imatinib, gefitinib, sunitinib, rituximab, alemtuzumab, trastuzumab, and bortezomib); differentiating agents (e.g., retinoids, tretinoin, and bexarotene); and hormonal agents (e.g., anti-estrogens, such as fulvestrant, tamoxifen, and toremifene; aromatase inhibitors, such as anastrozole, exemestane, and letrozole; progestins, such as megestrol acetate; estrogens; anti-androgens, such as bicalutamide, flutamide, and nilutamde; gonadotropin-releasing hormone (GnRH), also known as luteinizing hormone-releasing hormone (LHRH) agonists or analogs, such as' leuprolide and goserelin).

Furthermore, the present invention provides a method for preventing or treating precancerous transformation or a cancer in a mammal, which comprises administering the compound of formula (I) or (II), or a pharmaceutically acceptable salt, a hydrate, a solvate, or an isomer thereof to the mammal in need thereof.

The mammal may be a human.

In these methods, one or more compounds of the present invention may be administered in a medically effective amount as the sole pharmaceutical agent, or may be administered in combination therapy wherein a medically effective amount of the compound of the present invention is administered with a medically effective amount of at least one additional pharmaceutical agent.

Therefore, the method for preventing or treating precancerous transformation or a cancer may comprise the steps of: (i) administering to the mammal in need thereof a first composition comprising the compound of formula (I) or (II), and a pharmaceutically acceptable carrier; and (ii) administering to the mammal in need thereof a second composition comprising at least one additional pharmaceutical agent comprising a chemotherapeutic agent.

In the method, the first and second compositions are administered simultaneously, or sequentially and in any order.

In addition, the present invention provides a use of the compound of the present invention for the manufacture of a medicament for preventing or treating precancerous transformation or a cancer.

The present invention also provides a kit comprising the compounds or the pharmaceutical composition of the present invention and instructions for its use.

The following Examples are intended to further illustrate the present invention without limiting its scope.

NMR spectra were recorded in CDCl$_3$ and DMSO-d$_6$ solution in 5-mm o.d. tubes (Norell, Inc. 507-HP) at 30° C. and were collected on Varian VNMRS-400 at 400 MHz for $^1$H. The chemical shifts (δ) are relative to tetramethylsilane (TMS=0.00 ppm) and expressed in ppm. LC/MS was taken on Ion-trap Mass Spectrometer on FINNIGAN Thermo LCQ Advantage MAX, Agilent LC 1200 series (Column: YMC Hydrosphere (C18, Ø4.6×50 mm, 3 μm, 120 Å, 40° C.) operating in ESI(+) ionization mode; flow rate=1.0 mL/min; and Mobile phase=–0.01% heptafluorobutyric acid (HFBA) and 1.0% isopropyl alcohol (IPA) in water or CH$_3$CN).

Examples 1 to 5

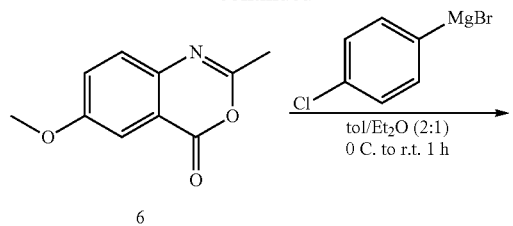

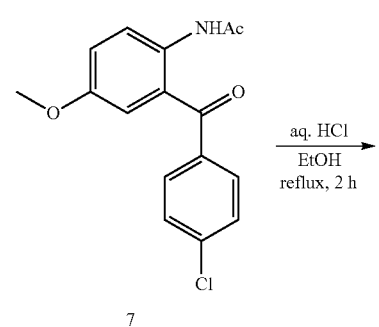

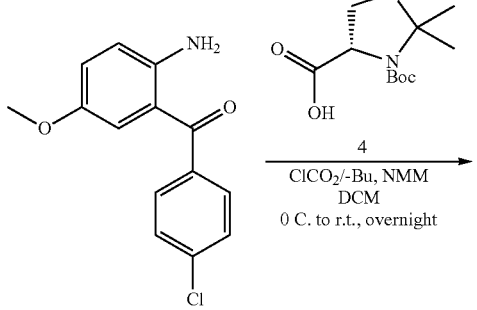

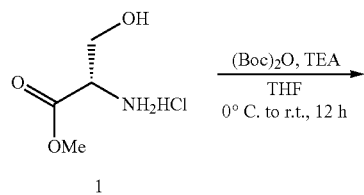

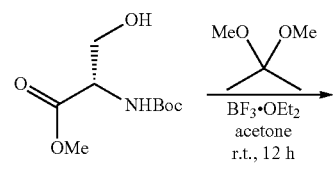

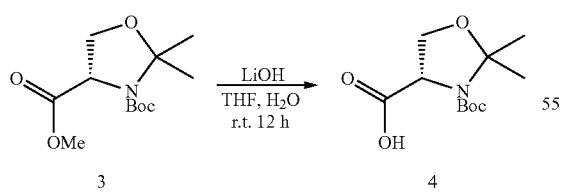

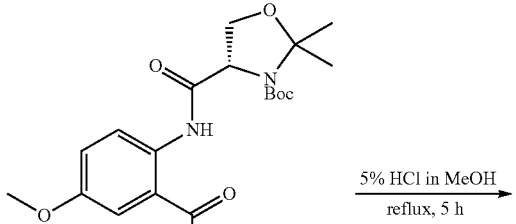

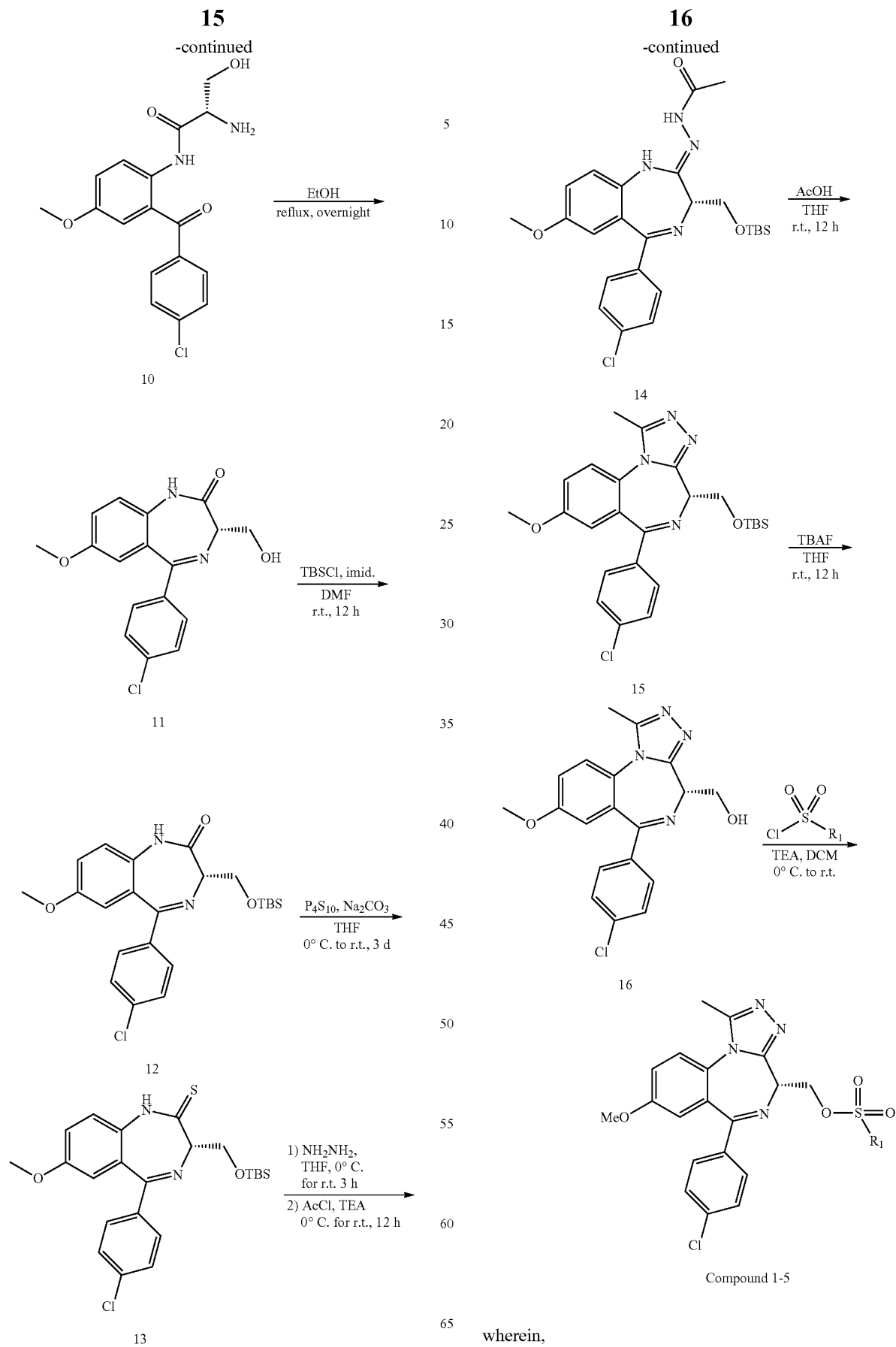
wherein,
R₁ has the same meanings as defined above.

Step 1: Preparation of (S)-methyl 2-((tert-butoxycarbonyl)amino)-3-hydroxypropanoate (Intermediate 2)

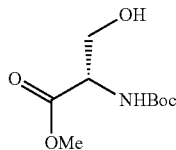

To a solution of (L)-serinemethyl ester HCl (5.00 g, 32.1 mmol) in dry tetrahydrofuran (THF) (64.3 mL) was added triethylamine (TEA) (9.85 mL, 70.7 mmol) followed by a solution of (Boc)$_2$O (7.46 mL, 32.1 mmol) in THF (30 mL) at 0° C. The reaction mixture was stirred for 12 hours at room temperature. After concentration of the resulting mixture in vacuo, the residue was partitioned between ethyl acetate (EtOAc) and water. The aqueous layer was extracted with EtOAc twice. The combined organic layers were dried over Na$_2$SO$_4$, filtered and concentrated in vacuo to obtain the title compound (7.16 g, >99%) as colorless oil, which was used for the next reaction without further purification.

$^1$H-NMR (400 MHz, CDCl$_3$): δ 5.54 (d, J=6.4 Hz, 1H), 4.39 (brs, 1H), 3.96 (ABX, J$_{AB}$=11.2 HZ, J$_{BX}$=3.6 Hz, 1H), 3.89 (ABX, J$_{AB}$=11.2 Hz, J$_A$=3.6 Hz, 1H), 3.79 (s, 3H), 2.81 (brs, 1H), 1.46 (s, 9H).

Step 2: Preparation of (S)-3-tert-butyl-4-methyl 2,2-dimethyloxazolidine-3,4-dicarboxylate (Intermediate 3)

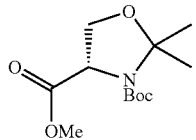

To a solution of (S)-methyl 2-((tert-butoxycarbonyl)amino)-3-hydroxypropanoate (6.16 g, 28.1 mmol) and 2,2-dimethoxypropane (34.4 mL, 281 mmol) in dry acetone (55 mL) was added boron trifluoride diethyl ether (BF$_3$.OEt$_2$) (0.214 mL, 1.68 mmol) at room temperature. The reaction mixture was stirred for 12 hours at room temperature. After concentration of the resulting mixture in vacuo, the residue was diluted with dichloromethane (DCM), and washed with 50% aq. NaHCO$_3$ solution and water twice. The separated organic layer was dried over Na$_2$SO$_4$, filtered and concentrated in vacuo. The residue was purified by column chromatography on SiO$_2$ (Hex:EtOAc=10:1) to obtain the title compound (6.75 g, 93%) as a yellow oil.

$^1$H-NMR (400 MHz, CDCl$_3$): (two sets from rotamers) δ 4.38 (dd, J=6.8, 2.8 Hz, 1H), 4.15 (ddd, J=9.2, 9.2, 7.2 Hz, 2H), 3.76 (s, 3H), 1.83 (s, 3H), 1.54 (s, 3H), 1.42 (s, 9H). δ 4.49 (dd, J=6.8, 2.8 Hz, 1H), 4.05 (ddd, J=9.2, 9.2, 3.2 Hz, 2H), 3.76 (s, 3H), 1.64 (s, 3H), 1.50 (s, 12H).

Step 3: Preparation of (S)-3-(tert-butoxycarbonyl)-2,2-dimethyloxazolidine-4-carboxylic acid (Intermediate 4)

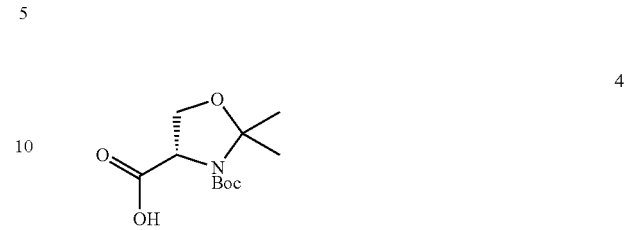

To a solution of (S)-3-tert-butyl-4-methyl 2,2-dimethyloxazolidine-3,4-dicarboxylate (6.75 g, 26.0 mmol) in THF (80 mL) and water (40 mL) was added lithium hydroxide hydrate (1.20 g, 28.6 mmol) at room temperature. The reaction mixture was stirred for 12 hours at room temperature. After evaporation of volatile solvents, the residue was diluted with EtOAc, neutralized with 2 N aq. HCl, washed with brine, dried over Na$_2$SO$_4$, filtered and concentrated in vacuo to obtain the title compound (6.32 g, 99%), which was used for the next reaction without further purification.

$^1$H-NMR (400 MHz, CDCl$_3$): (two sets of rotamers) δ 4.40-4.51 (m, 1H), 4.17-4.28 (m, 1H), 4.11-4.15 (m, 1H), 1.62 and 1.67 (s and s, 3H), 1.51 and 1.54 (s and s, 3H), 1.43 and 1.51 (s and s, 9H).

Step 4: Preparation of 6-methoxy-2-methyl-4H-benzo[d][1,3]oxazin-4-one (Intermediate 6)

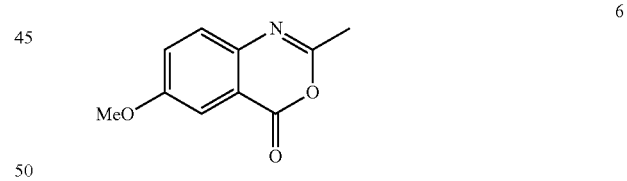

A mixture of 2-amino-5-methoxybenzoic acid (5.00 g, 29.9 mmol) and acetic anhydride (28.2 mL, 299 mmol) was refluxed for 4 hours and then concentrated in vacuo. The residue was diluted with toluene and concentrated in vacuo twice in order to remove remaining acetic acid. The residual solid was purified by column chromatography on SiO$_2$ (Hex:EtOAc=3:1 to 1:1 to 1:2) to obtain the title compound (5.68 g, 99%) as a pale yellow solid.

$^1$H-NMR (400 MHz, CDCl$_3$): δ 7.56 (d, J=2.8 Hz, 1H), 7.48 (d, J=8.8 Hz, 1H), 7.36 (dd, J=8.8, 3.2 Hz, 1H), 3.90 (s, 3H), 2.45 (s, 3H).

Step 5: Preparation of N-(2-(4-chlorobenzoyl)-4-methoxyphenyl)acetamide (Intermediate 7)

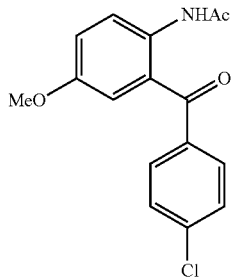

To a solution of 6-methoxy-2-methyl-4H-benzo[d][1,3]oxazin-4-one (5.68 g, 29.7 mmol) in a toluene (66 mL)/Et$_2$O (33 mL) at 0° C. was added dropwise (4-chlorophenyl)magnesium bromide (35.7 mL, 35.7 mmol, 1 M solution in THF). The reaction mixture was allowed to warm to room temperature and stirred for 1 hour. After being quenched with 1 N aq. HCl, the separated aqueous layer was extracted with EtOAc twice. The combined organic layers were washed with brine, dried over Na$_2$SO$_4$, filtered and concentrated in vacuo to obtain the title compound, which was used for the next reaction without further purification.

LC/MS m/z 303.99 [M+H]$^+$, Rt=0.64 min

Step 6: Preparation of (2-amino-5-methoxyphenyl)(4-chlorophenyl)methanone (Intermediate 8)

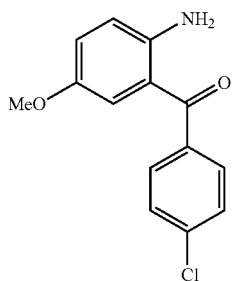

The crude N-(2-(4-chlorobenzoyl)-4-methoxyphenyl)acetamide obtained in step 5 was dissolved in EtOH (60 mL), and then 6 N aq. HCl (23 mL) was added thereto. The reaction mixture was refluxed for 2 hours and concentrated in vacuo. The residue was dissolved in EtOAc and neutralized with 1 N aq. NaOH. The separated aqueous layer was extracted with EtOAc twice and the combined organic layers were washed with brine, dried over Na$_2$SO$_4$, filtered and concentrated in vacuo. The residue was purified by column chromatography on SiO$_2$ (Hex:EtOAc=10:1 to 7:1 to 5:1) to obtain the title compound (5.10 g, 65% for 2 steps) as a yellow solid.

$^1$H-NMR (400 MHz, CDCl$_3$): δ 7.63 (dd, J=6.4, 1.6 Hz, 2H), 7.44 (dd, J=6.8, 1.6 Hz, 2H), 7.00 (dd, J=8.8, 3.2 Hz, 1H), 6.89 (d, J=3.2 Hz, 1H), 6.72 (d, J=8.8 Hz, 1H), 5.71 (brs, 2H), 3.66 (s, 3H).

Step 7: Preparation of (S)-tert-butyl 4-((2-(4-chlorobenzoyl)-4-methoxyphenyl)carbamoyl)-2,2-dimethyloxazolidine-3-carboxylate (Intermediate 9)

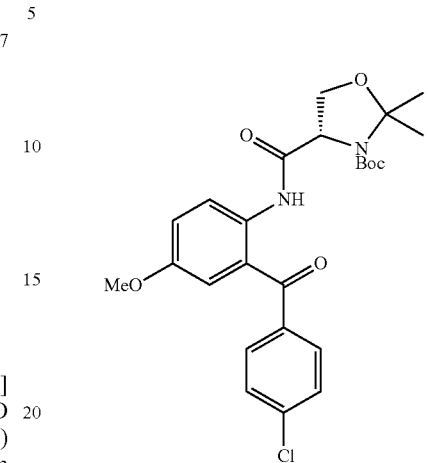

To a solution of (S)-3-(tert-butoxycarbonyl)-2,2-dimethyloxazolidine-4-carboxylic acid (4.78 g, 19.5 mmol) in DCM (100 mL) was added N-methylmorpholine (2.57 mL, 23.4 mmol) followed by isobutyl chloroformate (3.07 mL, 23.4 mmol) at 0° C. After stirred for 30 min at room temperature, (2-amino-5-methoxyphenyl)(4-chlorophenyl)methanone (5.10 g, 19.5 mmol) was added to the mixture. The resulting mixture was stirred overnight at room temperature. The reaction mixture was diluted with DCM, washed with 2 N aq. HCl, saturated aq. NaHCO$_3$ and water, dried over Na$_2$SO$_4$, filtered and concentrated in vacuo. The residue was purified by column chromatography on SiO$_2$ (Hex:EtOAc=5:1 to 3:1 to 1:1) to obtain the title compound (8.50 g, 89%) as viscous yellow oil.

$^1$H-NMR (400 MHz, CDCl$_3$): (two sets from rotamers) δ 10.83 and 10.73 (brs and brs, 1H), 8.56 (brs, 1H), 7.69 (d, J=7.6 Hz, 2H), 7.45 (d, J=8.4 Hz, 2H), 7.14 (d, J=8.0 Hz, 1H), 6.98 (brs, 1H), 4.21-4.51 (m, 3H), 3.76 (s, 3H), 1.84 and 1.79 (s and s, 3H), 1.59 and 1.57 (s and s, 4H), 1.46 (s, 3H), 1.24-1.29 (m, 5H).

Step 8: Preparation of (S)-2-amino-N-(2-(4-chlorobenzoyl)-4-methoxyphenyl)-3-hydroxy-propanamide (Intermediate 10)

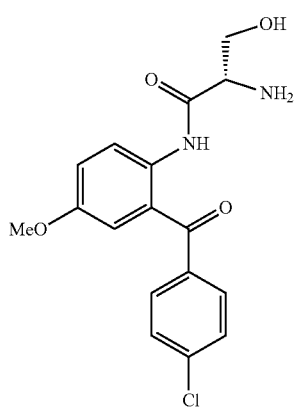

To a solution of (S)-tert-butyl 4-((2-(4-chlorobenzoyl)-4-methoxyphenyl)carbamoyl)-2,2-dimethyloxazolidine-3-carboxylate (3.00 g, 6.14 mmol) in MeOH (30 mL) was added conc. 5% HCl (6.0 mL) at room temperature. The reaction mixture was refluxed for 5 hours and then concentrated in vacuo. The residue was diluted with EtOAc and washed with saturated aq. NaHCO₃ and brine, dried over Na₂SO₄, filtered and concentrated in vacuo to obtain the title compound as a yellow solid, which was used for the next reaction without further purification.

¹H-NMR (400 MHz, CDCl₃): δ 11.33 (s, 1H), 8.42 (d, J=9.2 Hz, 1H), 7.73 (d, J=8.8 Hz, 2H), 7.46 (d, J=8.4 Hz, 2H), 7.13 (dd, J=9.2, 2.8 Hz, 1H), 6.99 (d, J=3.2 Hz, 1H), 3.94 (ABX, $J_{AB}$=10.7 Hz, $J_{BX}$=5.5 Hz, 1H), 3.79 (ABX, $J_{AB}$=10.7 Hz, $J_{AX}$=4.9 Hz, 1H), 3.77 (s, 3H), 3.58 (dd, J=5.6, 5.2 Hz, 1H), 2.01 (brs, 2H). *OH peak was not observed.

Step 9: Preparation of (S)-5-(4-chlorophenyl)-3-(hydroxymethyl)-7-methoxy-1H-benzo[e][1,4]-diazepin-2(3H)-one (Intermediate 11)

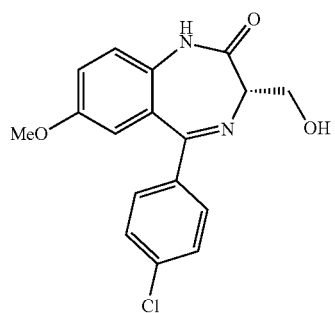

11

The crude (S)-2-amino-N-(2-(4-chlorobenzoyl)-4-methoxyphenyl)-3-hydroxy-propanamide obtained in step 8 was dissolved in EtOH (30 mL), and the reaction mixture was refluxed overnight and concentrated in vacuo to obtain the title compound (2.10 g, >99%) as a yellow solid, which was used for the next reaction without further purification.

¹H-NMR (400 MHz, CDCl₃): δ 7.95 (brs, 1H), 7.54 (d, J=8.4 Hz, 2H), 7.37 (d, J=8.4 Hz, 2H), 7.11 (dd, J=8.8, 2.4 Hz, 1H), 7.06 (d, J=8.8 Hz, 1H), 6.77 (d, J=2.8 Hz, 1H), 4.39-4.45 (m, 1H), 4.21-4.25 (m, 1H), 3.80 (dd, J=7.2, 5.2 Hz, 1H), 3.74 (s, 3H), 2.83 (m, 1H).

Step 10: Preparation of (S)-3-(((tert-butyldimethylsilyl)oxy)methyl)-5-(4-chlorophenyl)-7-methoxy-1H-benzo[e][1,4]diazepin-2(3H)-one (Intermediate 12)

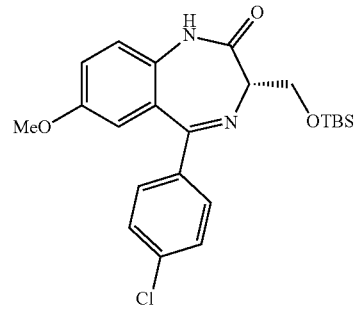

12

To a solution of crude (S)-5-(4-chlorophenyl)-3-(hydroxymethyl)-7-methoxy-1H-benzo[e][1,4]-diazepin-2(3H)-one (1.90 g, 5.74 mmol) in DMF (30 mL) were added imidazole (0.665 g, 9.77 mmol) followed by t-butyldimethylsilyl chloride (TBDMS-Cl) (1.30 g, 8.62 mmol) at room temperature. The reaction mixture was stirred at room temperature for 12 hours. After concentration of the resulting mixture in vacuo, the residue was diluted with EtOAc, washed with 2 N aq. HCl, saturated aq. NaHCO₃, water and brine successively, dried over Na₂SO₄, filtered and concentrated in vacuo. The residue was purified by column chromatography on SiO₂ (Hex:EtOAc=7:1 to 5:1 to 3:1) to obtain the title compound (2.30 g, 90%) as a white solid.

¹H-NMR (400 MHz, CDCl₃): δ 9.27 (brs, 1H), 7.51 (dd, J=8.4, 2.0 Hz, 2H), 7.33 (d, J=8.4, 2.0 Hz, 2H), 7.14 (d, J=8.8 Hz, 1H), 7.08 (dd, J=8.8, 2.8 Hz, 1H), 6.74 (d, J=2.8 Hz, 1H), 4.56 (ABX, $J_{AB}$=10.1 Hz, $J_A$=6.5 Hz, 1H), 4.29 (ABX, $J_{AB}$=10.1 Hz, $J_{AX}$=6.7 Hz, 1H), 3.74 (dd, J=6.8, 6.0 Hz, 1H), 3.73 (s, 3H), 0.94 (s, 9H), 0.18 (s, 3H), 0.16 (s, 3H).

Step 11: Preparation of (S)-3-(((tert-butyldimethylsilyl)oxy)methyl)-5-(4-chlorophenyl)-7-methoxy-1H-benzo[e][1,4]diazepine-2(3H)-thione (Intermediate 13)

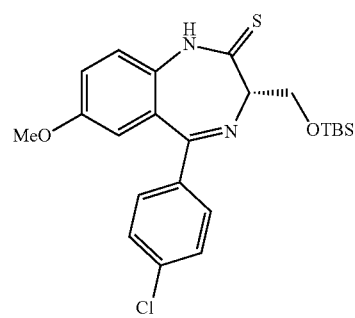

13

A mixture of P₄S₁₀ (1.00 g, 2.25 mmol) and sodium carbonate (0.238 g, 2.25 mmol) in THF (23 mL) was stirred for 1 hour at room temperature and cooled to 0° C. After addition of a solution of (S)-3-(((tert-butyldimethylsilyl)oxy)methyl)-5-(4-chlorophenyl)-7-methoxy-1H-benzo[e]

[1,4]diazepin-2(3H)-one (2.00 g, 4.49 mmol) in THF (5.0 mL) to the reaction mixture, the reaction mixture was stirred at 0° C. for 30 min and then for 3 days at room temperature. After filtration of the resulting mixture through a Celite pad, the filtrate was concentrated in vacuo. The residue was dissolved in EtOAc, washed with saturated aq. NaHCO$_3$ twice and brine, dried over Na$_2$SO$_4$, filtered and concentrated in vacuo. The residue was purified by column chromatography on SiO$_2$ (Hex:EtOAc=5:1) to obtain the title compound (1.48 g, 71%) as a viscous oil.

$^1$H-NMR (400 MHz, CDCl$_3$): δ 10.77 (brs, 1H), 7.51 (dd, J=8.4, 1.6 Hz, 2H), 7.33 (d, J=8.4, 2.4 Hz, 2H), 7.20 (d, J=9.2 Hz, 1H), 7.08 (dd, J=9.2, 3.2 Hz, 1H), 6.76 (d, J=3.2 Hz, 1H), 4.63 (ABX, J$_{AB}$=10.1 Hz, J$_{BX}$=7.3 Hz, 1H), 4.47 (ABX, J$_{AB}$=10.1 Hz, J$_{AX}$=5.5 Hz, 1H), 3.88 (dd, J=7.2, 5.6 Hz, 1H), 3.74 (s, 3H), 0.93 (s, 9H), 0.17 (s, 3H), 0.15 (s, 3H).

Step 12: Preparation of (R,Z)—N'-(3-(((tert-butyldimethylsilyl)oxy)methyl)-5-(4-chlorophenyl)-7-methoxy-1H-benzo[e][1,4]diazepin-2(3H)-ylidene) acetohydrazide (Intermediate 14)

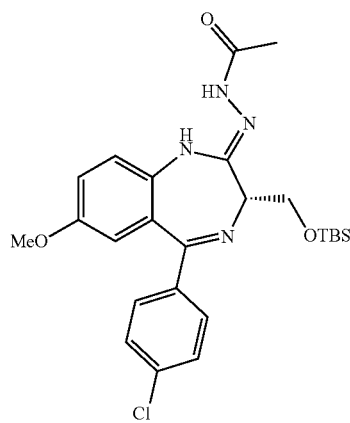

14

To a solution of (S)-3-(((tert-butyldimethylsilyl)oxy) methyl)-5-(4-chlorophenyl)-7-methoxy-1H-benzo[e][1,4] diazepine-2(3H)-thione (1.48 g, 3.21 mmol) in THF (32 mL) was added hydrazine monohydrate (0.604 mL, 19.3 mmol) at 0° C. The reaction mixture was stirred for 3 hours at room temperature and cooled to 0° C. After addition of TEA (2.68 mL, 19.3 mmol) followed by acetyl chloride (1.37 mL, 19.3 mmol), the reaction mixture was stirred at room temperature for 12 hours. After concentration of the resulting mixture in vacuo, the residue was dissolved in DCM and washed with water. The separated organic layer was dried over Na$_2$SO$_4$, filtered and concentrated in vacuo to obtain the title compound as a white solid, which was used for the next reaction without further purification.

$^1$H-NMR (400 MHz, CDCl$_3$): δ 10.66 (s, 1H), 8.52 (s, 1H), 7.52 (d, J=8.4 Hz, 2H), 7.32 (d, J=8.8 Hz, 2H), 7.17 (d, J=8.8 Hz, 1H), 7.04 (dd, J=8.8, 2.8 Hz, 1H), 6.65 (d, J=2.4 Hz, 1H), 4.49 (ABX, J$_{AB}$=9.9 Hz, J$_{BX}$=6.9 Hz, 1H), 4.30 (ABX, J$_{AB}$=9.9 Hz, J$_A$=5.9 Hz, 1H), 3.97 (dd, J=6.6, 6.4 Hz, 1H), 3.71 (s, 3H), 2.25 (s, 3H), 0.93 (s, 9H), 0.15 (s, 3H), 0.12 (s, 3H).

Step 13: Preparation of (R)-4-(((tert-butyldimethylsilyl)oxy)methyl)-6-(4-chlorophenyl)-8-methoxy-1-methyl-4H-benzo[f][1,2,4]triazolo[4,3-a][1,4]diazepine (Intermediate 15)

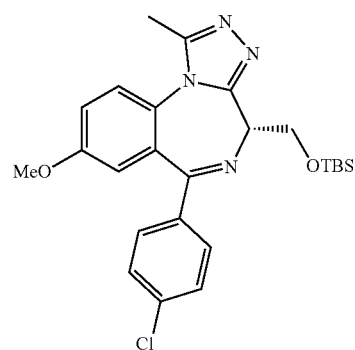

15

To a solution of above crude (R,Z)—N'-(3-(((tert-butyldimethylsilyl)oxy)methyl)-5-(4-chlorophenyl)-7-methoxy-1H-benzo-[e][1,4]diazepin-2(3H)-ylidene)acetohydrazide (1.61 g, 3.21 mmol) in THF (30 mL) was added acetic acid (6.00 mL, 105 mmol) at room temperature. The reaction mixture was stirred at room temperature for 12 hours, After concentration of the resulting mixture in vacuo, the residue was diluted with EtOAc, washed with saturated aq. NaHCO$_3$, dried over Na$_2$SO$_4$, filtered and concentrated in vacuo to obtain the title compound (1.48 g, 95% for 2 steps) as a viscous yellow oil.

$^1$H-NMR (400 MHz, CDCl$_3$): δ 7.55 (d, J=8.4 Hz, 2H), 7.39 (d, J=8.8 Hz, 1H), 7.35 (d, J=8.4 Hz, 2H), 7.20 (dd, J=9.2, 2.8 Hz, 1H), 6.90 (d, J=2.8 Hz, 1H), 4.71 (d, J=6.8 Hz, 2H), 4.17 (t, J=6.4 Hz, 1H), 3.82 (s, 3H), 2.61 (s, 3H), 0.95 (s, 9H), 0.21 (s, 3H), 0.17 (s, 3H).

Step 14: Preparation of (R)-(6-(4-chlorophenyl)-8-methoxy-1-methyl-4H-benzo[f][1,2,4]-triazolo[4,3-a][1,4]diazepin-4-yl)methanol (Intermediate 16)

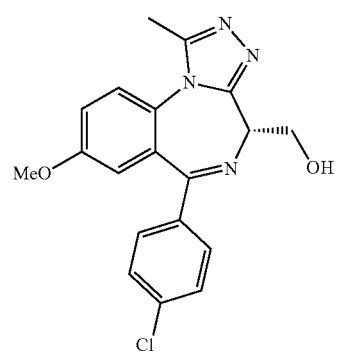

16

To a solution of (R)-4-(((tert-butyldimethylsilyl)oxy) methyl)-6-(4-chlorophenyl)-8-methoxy-1-methyl-4H-benzo [f][1,2,4]triazolo[4,3-a][1,4]diazepine (1.48 g, 3.06 mmol) in THF (15 mL) was added tetra-n-butylammonium fluoride (TBAF) (6.13 mL, 6.13 mmol, 1 M solution in THF) at room temperature. The reaction mixture was stirred at room temperature for 12 hours and quenched with saturated aq. NH₄Cl. The mixture was extracted with EtOAc twice. The combined organic layers were washed with brine, dried over Na₂SO₄, filtered and concentrated in vacuo. The residue was purified by column chromatography on SiO₂ (EtOAc only to EtOAc:MeOH=8:1 to 4:1) to obtain the title compound (983 mg, 87%) as a yellow solid.

$^1$H-NMR (400 MHz, CDCl₃): δ 7.55 (d, J=8.4 Hz, 2H), 7.40 (d, J=9.2 Hz, 1H), 7.35 (d, J=8.8 Hz, 2H), 7.22 (dd, J=8.8, 3.2 Hz, 1H), 6.89 (d, J=2.8 Hz, 1H), 4.64 (ABX, $J_{AB}$=11.6 Hz, $J_{BX}$=5.6 Hz, 1H), 4.53 (ABX, $J_{AB}$=11.6 Hz, $J_{AX}$=6.8 Hz, 1H), 3.24 (dd, J=6.4, 6.0 Hz, 1H), 3.81 (s, 3H), 2.64 (s, 3H). *OH peak was not observed.

LC/MS m/z 369.2 [M+H]$^+$, Rt=2.45 min.

Example 1: Preparation of (R)-(6-(4-chlorophenyl)-8-methoxy-1-methyl-4H-benzo[f]-[1,2,4]triazolo[4,3-a][1,4]diazepin-4-yl)methyl methanesulfonate (Compound 1)

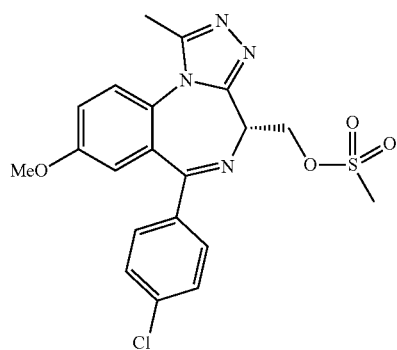

Compound 1

To a solution of (R)-(6-(4-chlorophenyl)-8-methoxy-1-methyl-4H-benzo[f][1,2,4]-triazolo-[4,3-a][1,4]diazepin-4-yl)methanol (Intermediate 16, 50.0 mg, 0.136 mmol) in DCM (3.0 mL) was added methane sulfonyl chloride (MsCl) (0.0210 mL, 0.271 mmol) followed by TEA (0.0470 mL, 0.339 mmol) at 0° C. The reaction mixture was stirred at 0° C. for 15 min and diluted with DCM. The resulting mixture was washed with 2 N aq. HCl and saturated aq. NaHCO₃, dried over Na₂SO₄, filtered and concentrated in vacuo. The residue was purified by column chromatography on SiO₂ (EtOAc:MeOH=10:1) to obtain the title compound (56.0 mg, 92%) as a yellow oil.

$^1$H-NMR (400 MHz, CDCl₃): δ 7.55 (d, J=8.4 Hz, 2H), 7.42 (d, J=8.8 Hz, 1H), 7.36 (d, J=8.4 Hz, 2H), 7.24 (dd, J=9.2, 2.8 Hz, 1H), 6.90 (d, J=2.8 Hz, 1H), 5.30 (ABX, $J_B$=10.3 Hz, $J_{BX}$=7.1 Hz, 1H), 5.17 (ABX, $J_{AB}$=10.3 Hz, $J_A$=6.5 Hz, 1H), 4.46 (dd, J=6.8, 6.4 Hz, 1H), 3.83 (s, 3H), 3.21 (s, 3H), 2.63 (s, 3H).

LC/MS m/z 447.1 [M+H]$^+$, Rt=2.87 min

Example 2: Preparation of (R)-(6-(4-chlorophenyl)-8-methoxy-1-methyl-4H-benzo[f][1,2,4]triazolo[4,3-a][1,4]diazepin-4-yl)methyl ethanesulfonate (Compound 2)

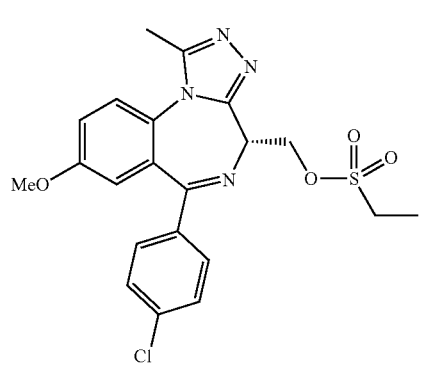

Compound 2

To a solution of (R)-(6-(4-chlorophenyl)-8-methoxy-1-methyl-4H-benzo[f][1,2,4]-triazolo-[4,3-a][1,4]diazepin-4-yl)methanol (Intermediate 16, 0.100 g, 0.271 mmol) in DCM (3.0 mL) was added ethanesulfonyl chloride (70.0 mg, 0.542 mmol) followed by TEA (0.0940 mL, 0.678 mmol) at 0° C. The reaction mixture was stirred at room temperature for 5 hours. After concentration of the resulting mixture in vacuo, the residue was purified by column chromatography on SiO₂ (EtOAc:MeOH=10:1 to 5:1) to obtain the title compound (68.0 mg, 54%) as brown oil.

$^1$H-NMR (400 MHz, CDCl₃): δ 7.55 (d, J=8.4 Hz, 2H), 7.42 (d, J=8.8 Hz, 1H), 7.36 (d, J=8.8 Hz, 2H), 7.24 (dd, J=8.8, 2.8 Hz, 1H), 6.90 (d, J=2.8 Hz, 1H), 5.28 (ABX, $J_{AB}$=10.3 Hz, $J_{BX}$=6.9 Hz, 1H), 5.18 (ABX, $J_{AB}$=10.3 Hz, $J_{AX}$=6.3 Hz, 1H), 4.46 (dd, J=6.8, 6.8 Hz, 1H), 3.83 (s, 3H), 3.33 (q, J=7.2 Hz, 2H), 2.63 (s, 3H), 1.50 (t, J=7.6 Hz, 3H).

LC/MS m/z 461.2 [M+H]$^+$, Rt=3.17 min

Example 3: Preparation of (R)-(6-(4-chlorophenyl)-8-methoxy-1-methyl-4H-benzo[f][1,2,4]triazolo[4,3-a][1,4]diazepin-4-yl)methyl propane-1-sulfonate (Compound 3)

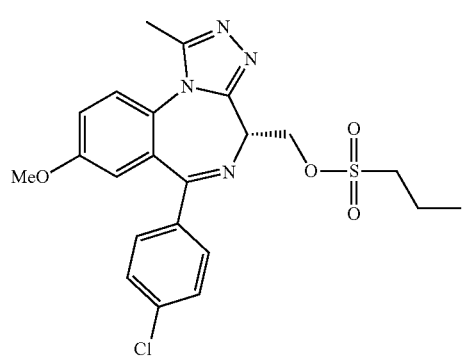

Compound 3

To a solution of (R)-4-(((tert-butyldimethylsilyl)oxy)methyl)-6-(4-chlorophenyl)-8-methoxy-1-methyl-4H-benzo[f][1,2,4]triazolo[4,3-a][1,4]diazepine (Intermediate 15, 50.0 mg, 0.136 mmol) in DCM (1 mL) was added propane- 1-sulfonyl chloride (30.5 μL, 0.271 mmol) followed by TEA (47.2 μL, 0.339 mmol) at 0° C. The reaction mixture was stirred at room temperature for 3 hours and diluted with DCM. The resulting mixture was washed with 2 N aq. HCl and saturated aq. NaHCO$_3$, dried over Na$_2$SO$_4$, filtered and concentrated in vacuo. The residue was purified by column chromatography on SiO$_2$ (EtOAc:MeOH=10:1) to obtain the title compound (63.0 mg, 98%) as a white solid.

$^1$H-NMR (400 MHz, CDCl$_3$): δ 7.55 (d, J=8.4 Hz, 2H), 7.41 (d, J=8.8 Hz, 1H), 7.36 (d, J=8.4 Hz, 2H), 7.23 (dd, J=9.0, 3.0 Hz, 1H), 6.89 (d, J=2.8 Hz, 1H), 5.27 (ABX, J$_{AB}$=10.3 Hz, J$_{BX}$=6.4 Hz, 1H), 5.18 (ABX, J$_{AB}$=10.3 Hz, J=7.6 Hz, 1H), 4.46 (t, J=6.6 Hz, 1H), 3.82 (s, 3H), 3.27 (t, J=7.8 Hz, 2H), 2.63 (s, 3H), 2.15-1.93 (m, 2H), 1.12 (t, J=7.4 Hz, 3H).

LC-MS m/z 475.1 [M+H]$^+$, Rt=3.13 min.

Example 4: Preparation of (R)-(6-(4-chlorophenyl)-8-methoxy-1-methyl-4H-benzo[f][1,2,4]triazolo[4,3-a][1,4]diazepin-4-yl)methyl cyclopropanesulfonate (Compound 4)

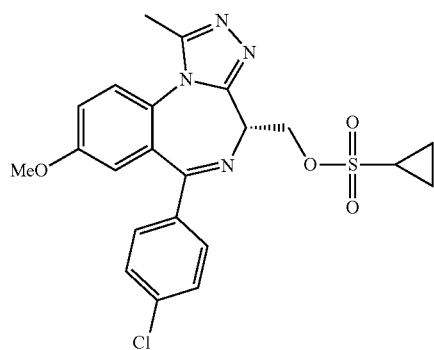

Compound 4

To a solution of (R)-4-(((tert-butyldimethylsilyl)oxy)methyl)-6-(4-chlorophenyl)-8-methoxy-1-methyl-4H-benzo[f][1,2,4]triazolo[4,3-a][1,4]diazepine (Intermediate 15, 60.0 mg, 0.163 mmol) in THF (0.81 mL) was added lithium bis(trimethylsilyl)amide (LHMDS) (1.6 M in THF, 0.122 mL, 0.195 mmol) followed by cyclopropanesulfonyl chloride (0.249 mL, 0.244 mmol) at −78° C. The reaction mixture was allowed to warm to room temperature and stirred at room temperature overnight. After quenched with saturated aq. NH$_4$Cl, the mixture was diluted with DCM, washed with 2 N aq. HCl and saturated aq. NaHCO$_3$, dried over Na$_2$SO$_4$, filtered and concentrated in vacuo. The residue was purified by column chromatography on SiO$_2$ (EtOAc:MeOH=10:1) to obtain the title compound (33.0 mg, 43%) as a yellow solid.

$^1$H-NMR (400 MHz, CDCl$_3$): δ 7.56 (d, J=8.0 Hz, 2H), 7.41 (d, J=8.8 Hz, 1H), 7.36 (d, J=7.6 Hz, 2H), 7.23 (dd, J=9.0, 2.2 Hz, 1H), 6.89 (d, J=2.4 Hz, 1H), 5.32 (ABX, J$_{AB}$=10.2 Hz, J$_{BX}$=5.6 Hz, 1H), 5.23 (ABX, J$_{AB}$=10.2 Hz, J$_{AX}$=8.0 Hz, 1H), 4.46 (t, J=6.4 Hz, 1H), 3.82 (s, 3H), 2.73-2.65 (m, 1H), 2.63 (s, 3H), 1.37-1.33 (m, 2H), 1.20-1.15 (m, 2H).

LC-MS m/z 473.2 [M+H]$^+$, Rt=3.31 min.

Example 5: Preparation of (R)-(6-(4-chlorophenyl)-8-methoxy-1-methyl-4H-benzo[f][1,2,4]triazolo[4,3-a][1,4]diazepin-4-yl)methyl benzenesulfonate (Compound 5)

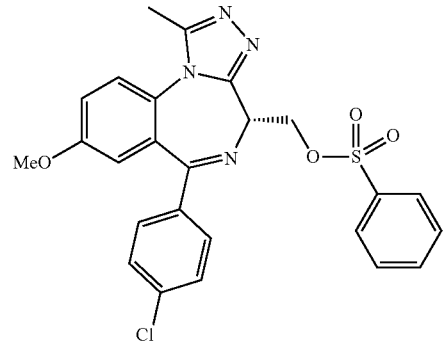

Compound 5

To a solution of (R)-(6-(4-chlorophenyl)-8-methoxy-1-methyl-4H-benzo[f][1,2,4]-triazolo-[4,3-a][1,4]-diazepin-4-yl)methanol (Intermediate 16, 50.0 mg, 0.136 mmol) in DCM (3.0 mL) was added benzenesulfonyl chloride (48.0 mg, 0.271 mmol) followed by TEA (0.0470 mL, 0.339 mmol) at 0° C. The reaction mixture was stirred at room temperature for 3 hours. After concentration of the resulting mixture in vacuo, the residue was purified by column chromatography on SiO$_2$ (EtOAc:MeOH=10:1) to obtain the title compound (14.0 mg, 20%) as brown oil.

$^1$H-NMR (400 MHz, CDCl$_3$): δ 8.02 (d, J=7.6 Hz, 2H), 7.69 (t, J=7.6 Hz, 1H), 7.59 (t, J=8.0 Hz, 2H), 7.50 (d, J=8.4 Hz, 2H), 7.38 (d, J=8.8 Hz, 1H), 7.34 (d, J=8.4 Hz, 2H), 7.22 (dd, J=8.8, 2.0 Hz, 1H), 6.89 (d, J=2.0 Hz, 1H), 5.02-5.12 (m, 2H), 4.45 (dd, J=8.0, 4.8 Hz, 1H), 3.83 (s, 3H), 2.60 (s, 3H).

LC/MS m/z 509.2 [M+H]$^+$, Rt=2.94 min

Example 6: Preparation of (R)-(6-(4-chlorophenyl)-1-methyl-4H-benzo[f][1,2,4]triazolo[4,3-a][1,4]diazepin-4-yl)methyl methanesulfonate (Compound 6)

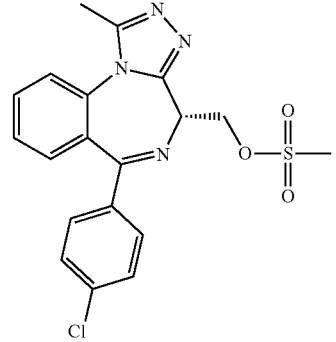

Compound 6

The procedure to preparing (R)-(6-(4-chlorophenyl)-1-methyl-4H-benzo[f][1,2,4]triazolo[4,3-a][1,4]diazepin-4-yl)methanol was repeated except that 2-aminobenzoic acid (2.0 g, 14.6 mmol) was used instead of 2-amino-5-methoxybenzoic acid. To a solution of (R)-(6-(4-chlorophenyl)-1- methyl-4H-benzo[f][1,2,4]triazolo[4,3-a][1,4]diazepin-4-yl)methanol (596 mg, 1.76 mmol) in DCM (8.0 mL) was added MsCl (0.274 mL, 3.52 mmol) followed by TEA (0.613 mL, 4.40 mmol) at 0° C. The reaction mixture was stirred at room temperature for 4 hours. After dilution with DCM, the resulting mixture was washed with 2 N aq. HCl and saturated aq. NaHCO$_3$, dried over Na$_2$SO$_4$, filtered and concentrated in vacuo. The residue was purified by column chromatography on SiO$_2$ (EtOAc:MeOH=10:1) to obtain the title compound (645 mg, 88%) as a yellow oil.

$^1$H-NMR (400 MHz, CDCl$_3$): δ 7.74 (td, J=7.7, 1.6 Hz, 1H), 7.55-7.46 (m, 5H), 7.36 (d, J=8.8 Hz, 2H), 5.32 (ABX, J$_B$=10.1 Hz, J$_{BX}$=6.7 Hz, 1H), 5.17 (ABX, J$_{AB}$=10.1 Hz, J$_{AX}$=6.9 Hz, 1H), 4.46 (t, J=6.6 Hz, 1H), 3.21 (s, 3H), 2.67 (s, 3H).

LC-MS m/z 417.2 [M+H]$^+$, Rt=2.59 min.

Example 7: Preparation of (R)-(6-(4-cyanophenyl)-8-methoxy-1-methyl-4H-benzo[f][1,2,4]triazolo[4,3-a][1,4]diazepin-4-yl)methyl methanesulfonate (Compound 7)

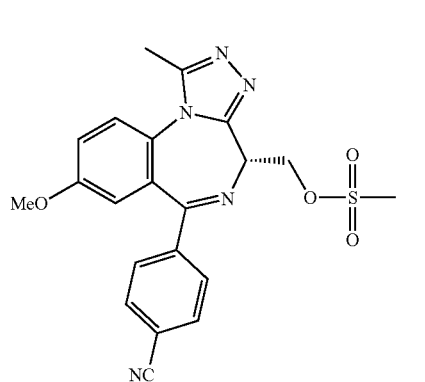

Compound 7

The procedure in accordance with Example 1 was repeated except that 1,4-dibromobenzene (4.19 g, 0.18 mmol) was used instead of (4-chlorophenyl)magnesium bromide to obtain the title compound (23 mg, 47%)

$^1$H-NMR (400 MHz, CDCl$_3$): δ 7.73 (d, J=8.4 Hz, 2H), 7.69 (d, J=8.4 Hz, 2H), 7.45 (d, J=8.8 Hz, 1H), 7.28-7.25 (m, 1H), 6.84 (d, J=2.8 Hz, 1H), 5.31 (ABX, J$_{AB}$=10.4 Hz, J$_{BX}$=7.1 Hz, 1H), 5.20 (ABX, J$_{AB}$=10.4 Hz, J$_{AX}$=6.1 Hz, 1H), 4.51 (t, J=6.8 Hz, 1H), 3.83 (s, 3H), 3.20 (s, 3H), 2.64 (s, 3H).

LC-MS m/z 438.2 [M+H]$^+$, Rt=2.89 min.

Example 8: Preparation of (R)-(6-(4-chlorophenyl)-8-methoxy-1-methyl-4H-benzo[f][1,2,4]triazolo[4,3-a][1,4]diazepin-4-yl)methyl sulfamate (Compound 8)

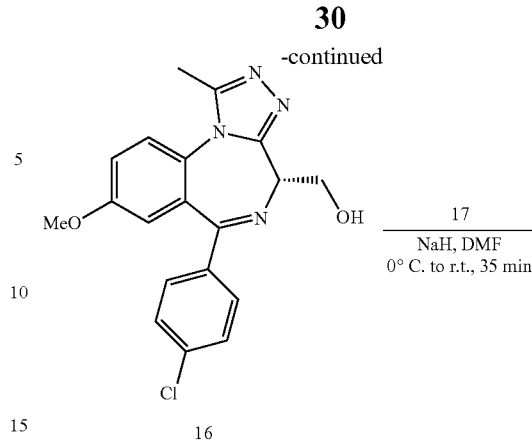

Compound 8

Step 1: Preparation of sulfamoyl chloride (2M solution in CH$_3$CN) (Intermediate 17)

17

A round bottom flask equipped with stir bar and rubber septum was charged with sulfurisocyanatidic chloride (200 mg, 1.41 mmol). The flask was cooled to 0° C., and then HCO$_2$H (288 μL, 7.50 mmol) as added thereto dropwise. After vigorous stirring for 5 min at 0° C., CH$_3$CN (0.70 mL) was added to the mixture. The mixture was stirred vigorously at 0° C. for 1 hour, warmed to room temperature for overnight to obtain a solution of the title compound in CH$_3$CN (approx. 2 M), which was used for the next reaction without further purification.

Step 2: Preparation of (R)-(6-(4-chlorophenyl)-8-methoxy-1-methyl-4H-benzo[f][1,2,4]triazolo[4,3-a][1,4]diazepin-4-yl)methyl sulfamate (Compound 8)

Compound 8

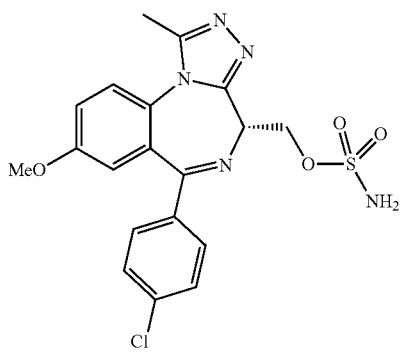

To a solution of ((R)-6-(4-chlorophenyl)-8-methoxy-1-methyl-4H-benzo[f][1,2,4]triazolo[4,3-a][1,4]diazepin-4-yl)methanol (Intermediate 16, 50.0 mg, 0.136 mmol) in DMF (0.70 mL) was added NaH (55 wt %, 8.87 mg, 0.203 mmol) followed by sulfamoyl chloride (2 M solution in CH₃CN, 0.203 mL, 0.406 mmol) at 0° C. The reaction mixture was stirred at room temperature for 35 min and then diluted with EtOAc. The resulting mixture was washed with 2 N aq. HCl and saturated aq. NaHCO₃, dried over Na₂SO₄, filtered and concentrated in vacuo. The residue was purified by column chromatography on SiO₂ (EtOAc:MeOH=10:1) to obtain the title compound (48.0 mg, 79%) as a white solid.

¹H-NMR (400 MHz, CDCl₃): δ 7.54 (d, J=8.0 Hz, 2H), 7.42 (d, J=8.8 Hz, 1H), 7.36 (d, J=8.0 Hz, 2H), 7.24 (dd, J=9.4, 2.6 Hz, 1H), 6.89 (d, J=2.4 Hz, 1H), 5.86 (s, 2H), 5.33 (dd, J=18, 10 Hz, 1H), 5.04 (dd, J=10.4, 5.6 Hz, 1H), 4.46 (t, J=6.6 Hz, 1H), 3.82 (s, 3H), 2.63 (s, 3H).

LC-MS m/z 448.2 [M+H]⁺, Rt=2.97 min.

Example 9: Preparation of (R)-(6-(4-chlorophenyl)-8-methoxy-1-methyl-4H-benzo[f][1,2,4]triazolo[4,3-a][1,4]diazepin-4-yl)methyl dimethylsulfamate (Compound 9)

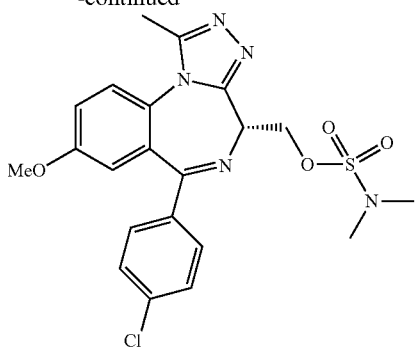

Compound 9

To a solution of (R)-(6-(4-chlorophenyl)-8-methoxy-1-methyl-4H-benzo[f][1,2,4]triazolo[4,3-a][1,4]diazepin-4-yl)methyl sulfamate (97.0 mg, 0.217 mmol) in DMF (0.11 mL) was added NaH (55 wt %, 20.8 mg, 0.476 mmol) followed by methyl iodide (MeI) (54.2 μL, 0.866 mmol) at 0° C. The reaction mixture was stirred at room temperature for 2 hours and diluted with EtOAc. The resulting mixture was washed with 2 N aq. HCl and saturated aq. NaHCO₃, dried over Na₂SO₄, filtered and concentrated in vacuo. The residue was purified by prep-HPLC to obtain the title compound (38.0 mg, 37%) as a white solid.

¹H-NMR (400 MHz, CDCl₃): δ 7.55 (d, J=8.4 Hz, 2H), 7.41 (d, J=9.2 Hz, 1H), 7.36 (d, J=8.4 Hz, 2H), 7.23 (dd, J=9.0, 3.0 Hz, 1H), 6.89 (d, J=2.8 Hz, 1H), 5.23 (ABX, $J_{AB}$=10.3 Hz, $J_{BX}$=5.9 Hz, 1H), 5.12 (ABX, $J_{AB}$=10.3 Hz, $J_{AX}$=7.7 Hz, 1H), 4.47 (t, J=6.8 Hz, 1H), 3.82 (s, 3H), 3.01 (s, 6H), 2.63 (s, 3H).

LC-MS m/z 476.2 [M+H]⁺, Rt=2.92 min.

Example 10: Preparation of (R)-(6-(4-chlorophenyl)-8-methoxy-1-methyl-4H-benzo[f][1,2,4]triazolo[4,3-a][1,4]diazepin-4-yl)methyl methylsulfamate (Compound 10)

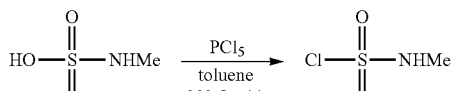

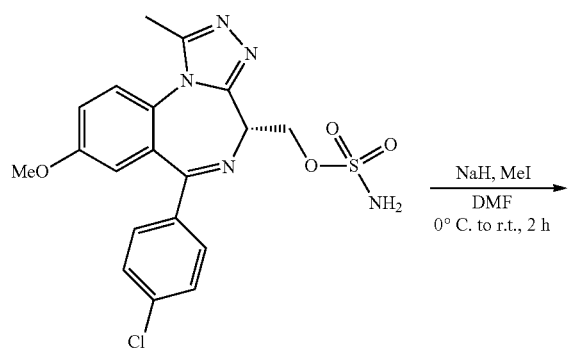

Compound 8

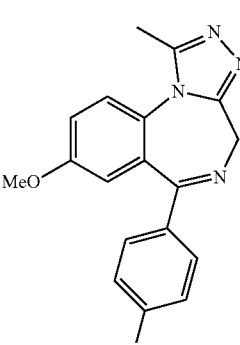

16

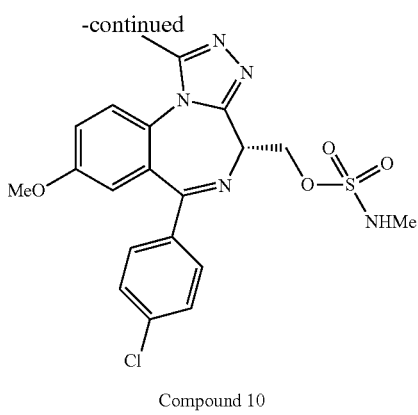

Compound 10

Step 1: Preparation of methylsulfamoyl chloride (Intermediate 18)

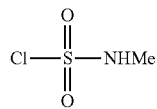

To a solution of methylsulfamic acid (100 mg, 0.900 mmol) in toluene (1.0 mL) was added PCl$_5$ (187 mg, 0.900 mmol) under a nitrogen atmosphere. The reaction mixture was slowly heated to 80° C. and stirred for 4 hours. After being cooled to room temperature, the reaction mixture was concentrated in vacuo to obtain the title compound (99.0 mg, 85%), which was used for the next reaction without further purification.

$^1$H-NMR (400 MHz, CDCl$_3$): δ 13.8 (brs, 1H), 2.96 (s, 3H).

Step 2: Preparation of (R)-(6-(4-chlorophenyl)-8-methoxy-1-methyl-4H-benzo[f][1,2,4]triazolo[4,3-a][1,4]diazepin-4-yl)methyl methylsulfamate (Compound 10)

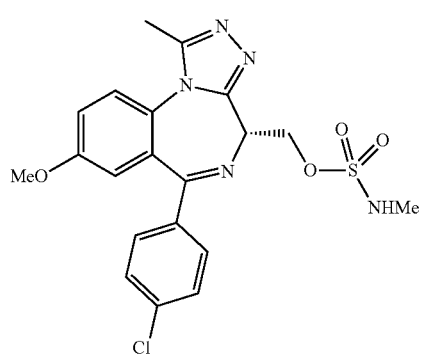

Compound 10

To a solution of (R)-(6-(4-chlorophenyl)-8-methoxy-1-methyl-4H-benzo[f][1,2,4]triazolo[4,3-a][1,4]diazepin-4-yl)methanol (50.0 mg, 0.136 mmol) in DMF (0.70 mL) were added NaH (55 wt %, 8.87 mg, 0.203 mmol) followed by methylsulfamoyl chloride (52.7 mg, 0.407 mmol) at 0° C. The reaction mixture was stirred at room temperature for 40 min and diluted with EtOAc. The resulting mixture was washed with 2 N aq. HCl and saturated aq. NaHCO$_3$, dried over Na$_2$SO$_4$, filtered and concentrated in vacuo. The residue was purified by column chromatography on SiO$_2$ (EtOAc:MeOH=10:1) to obtain the title compound (45.0 mg, 72%) as a white solid.

$^1$H-NMR (400 MHz, CDCl$_3$): δ 7.54 (d, J=8.4 Hz, 2H), 7.41 (d, J=8.8 Hz, 1H), 7.36 (d, J=8.4 Hz, 2H), 7.23 (dd, J=8.8, 2.8 Hz, 1H), 6.89 (d, J=2.8 Hz, 1H), 5.23 (brs, 1H), 5.25 (ABX, J$_{AB}$=10.2 Hz, J$_{BX}$=6.2 Hz, 1H), 5.05 (ABX, J$_{AB}$=10.2 Hz, J=7.0 Hz, 1H), 4.46 (t, J=6.8 Hz, 1H), 2.90 (d, J=5.2 Hz, 3H), 3.83 (s, 3H), 2.63 (s, 3H).

LC-MS m/z 462.2 [M+H]$^+$, Rt=2.95 min.

Example 11: Preparation of (R)-(6-(4-chlorophenyl)-1-methyl-8-(1-methyl-1H-pyrazol-4-yl)-4H-benzo[f][1,2,4]triazolo[4,3-a][1,4]diazepin-4-yl)methyl methanesulfonate (Compound 11)

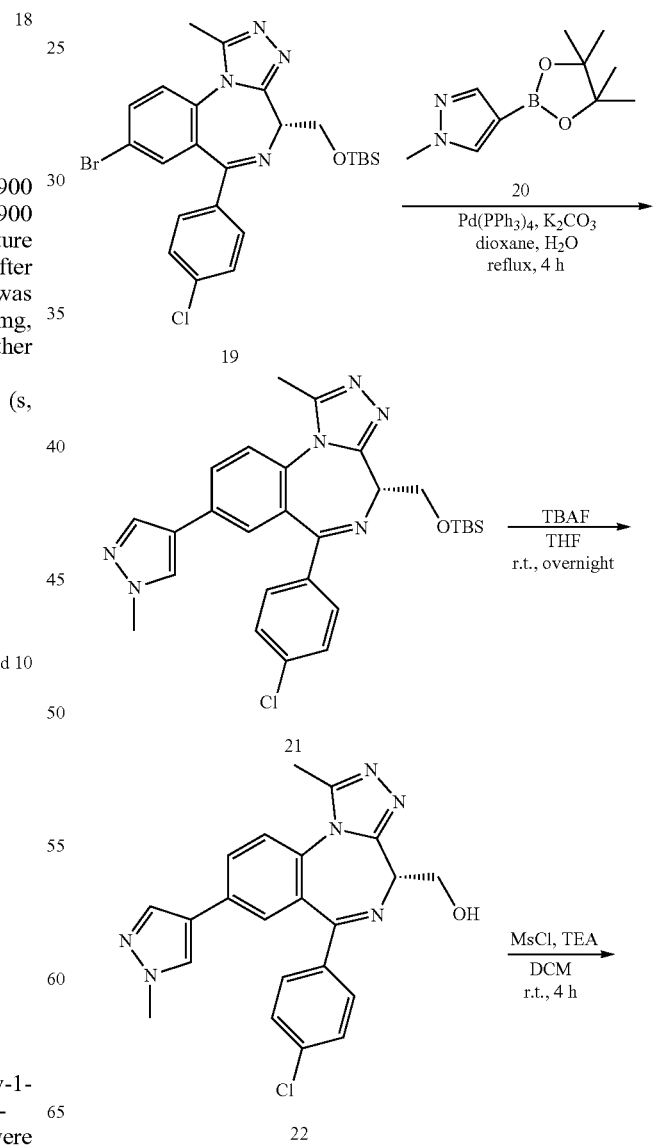

-continued

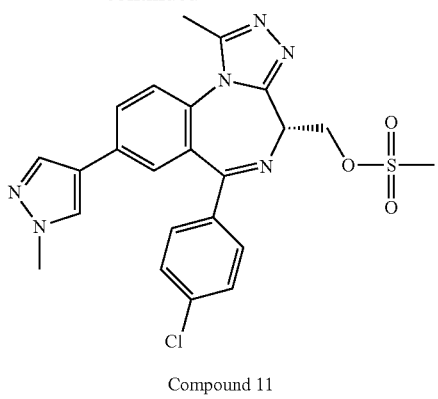

Compound 11

Step 1: Preparation of (R)-8-bromo-4-(((tert-butyldimethylsilyl)oxy)methyl-6-(4-chlorophenyl)-1-methyl-4H-benzo[f][1,2,4]triazolo[4,3-a][1,4]diazepine (Intermediate 19)

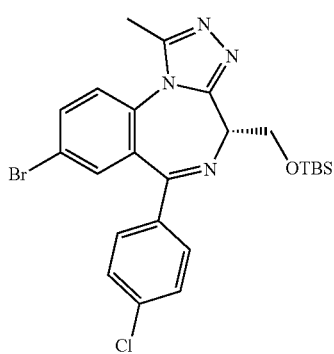

19

(Z)—N'—((R,Z)-7-bromo-3-((tert-butyldimethylsilyloxy)methyl)-5-(4-chlorophenyl)-1H-benzo[e][1,4]diazepin-2(3H)-ylidene)acetohydrazide was synthesized in a similar manner, employing 2-amino-5-bromobenzoic acid (2 g, 9.26 mmol) as a starting material. To a solution of (Z)—N'—((R,Z)-7-bromo-3-((tert-butyldimethylsilyloxy)methyl)-5-(4-chlorophenyl)-1H-benzo[e][1,4]diazepin-2-(3H)-ylidene)acetohydrazide (115 mg, 0.209 mmol) in THF (30 mL) was added acetic acid (395 µL, 6.90 mmol) at room temperature. The reaction mixture was stirred at room temperature overnight. After concentration of the resulting mixture in vacuo, the residue was diluted with EtOAc, washed with saturated aq. NaHCO₃, dried over Na₂SO₄, filtered and concentrated in vacuo to obtain the title compound (105 mg, 94% for 2 steps) as a viscous yellow oil.

¹H-NMR (400 MHz, CDCl₃): δ 7.81 (d, J=8.4 Hz, 1H), 7.59 (s, 1H), 7.51 (d, J=8.4 Hz, 2H), 7.37 (d, J=9.2 Hz, 2H), 7.35 (d, J=8.0 Hz, 1H), 4.70 (d, J=6.4 Hz, 2H), 4.15 (t, J=6.2 Hz, 1H), 2.62 (s, 3H), 0.95 (s, 9H), 0.20 (s, 3H), 0.17 (s, 3H).

Step 2: Preparation of (R)-4-(((tert-butyldimethylsilyl)oxy)methyl)-6-(4-chlorophenyl)-1-methyl-8-(1-methyl-1H-pyrazol-4-yl)-4H-benzo[f][1,2,4]triazolo-[4,3-a][1,4]diazepine (Intermediate 21)

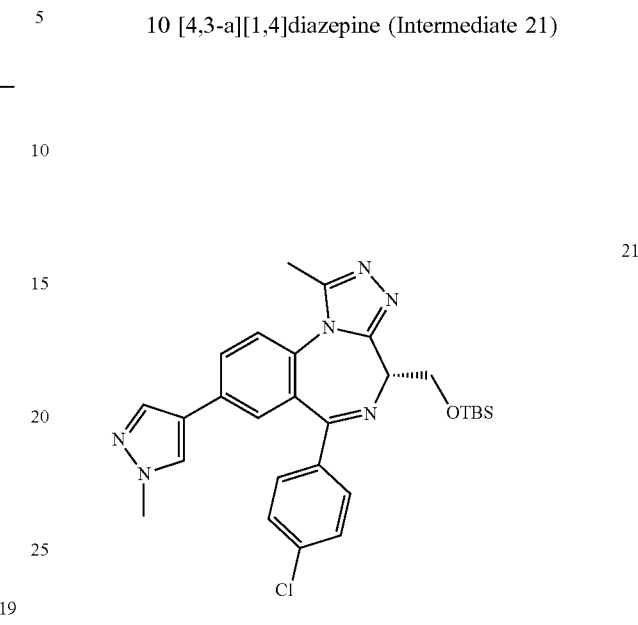

21

A dried round bottom flask charged with (R)-8-bromo-4-(((tert-butyldimethylsilyl)oxy)methyl)-6-(4-chlorophenyl)-1-methyl-4H-benzo[f][1,2,4]triazolo[4,3-a][1,4]diazepine (110 mg, 0.207 mmol), 1-methyl-4-(4,4,5,5-tetramethyl-1,3,2-dioxaborolan-2-yl)-1H-pyrazole (52.0 mg, 0.248 mmol), dioxane (8.0 mL) and water (4.0 mL) was evacuated and refilled with nitrogen several times. After addition of Pd(PPh₃)₄ (24.0 mg, 0.021 mmol) and K₂CO₃ (57.2 mg, 0.414 mmol) at room temperature, the reaction mixture was refluxed for 4 hours. After being cooled to room temperature, the reaction mixture was treated with water (5.0 mL) and then filtered through a Celite pad. The filtrate was partitioned between saturated aq. NaHCO₃ (5.0 mL) and DCM (10 mL). The separated aqueous layer was extracted with DCM, and the combined organic layers were washed with brine, dried over Na₂SO₄, filtered and concentrated in vacuo. The residue was purified by column chromatography on SiO₂ (EtOAc:MeOH=10:1) to obtain the title compound (65.0 mg, 59%) as a yellow solid.

¹H-NMR (400 MHz, CDCl₃): δ 7.75 (dd, J=8.4, 1.6 Hz, 1H), 7.73 (s, 1H), 7.60 (s, 1H), 7.57 (d, J=8.4 Hz, 2H), 7.47 (d, J=2.0 Hz, 1H), 7.45 (d, J=8.4 Hz, 1H), 7.35 (d, J=8.4 Hz, 1H), 4.72 (d, J=6.8 Hz, 2H), 4.21 (t, J=6.4 Hz, 1H), 3.95 (s, 3H), 2.65 (s, 3H), 0.95 (s, 9H).

Step 3: Preparation of (R)-(6-(4-chlorophenyl)-1-methyl-8-(1-methyl-1H-pyrazol-4-yl)-4H-benzo[f][1,2,4]triazolo[4,3-a][1,4]diazepin-4-yl)methanol (Intermediate 22)

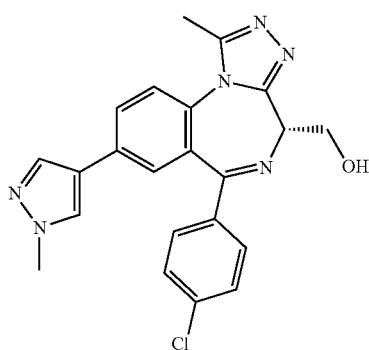

22

To a solution of (R)-4-(((tert-butyldimethylsilyl)oxy)methyl)-6-(4-chlorophenyl)-1-methyl-8-(1-methyl-1H-pyrazol-4-yl)-4H-benzo[f][1,2,4]triazolo [4,3-a][1,4]diazepine (65.0 mg, 0.122 mmol) in THF (1.0 mL) was added TBAF (244 μL, 0.244 mmol, 1 M solution in THF) at room temperature. The reaction mixture was stirred at room temperature overnight and quenched with saturated aq. NH$_4$Cl. The mixture was extracted with EtOAc twice. The combined organic layers were washed with brine, dried over Na$_2$SO$_4$, filtered and concentrated in vacuo. The residue was purified by column chromatography on SiO$_2$ (EtOAc only to EtOAc:MeOH=8:1 to 4:1) to obtain the title compound (23.0 mg, 45%) as a yellow solid.

LC/MS m/z 419.12 [M+H]$^+$, Rt=0.24 min.

Step 4: Preparation of (R)-(6-(4-chlorophenyl)-1-methyl-8-(1-methyl-1H-pyrazol-4-yl)-4H-benzo[f][1,2,4]triazolo[4,3-a][1,4]diazepin-4-yl)methyl methanesulfonate (Compound 11)

Compound 11

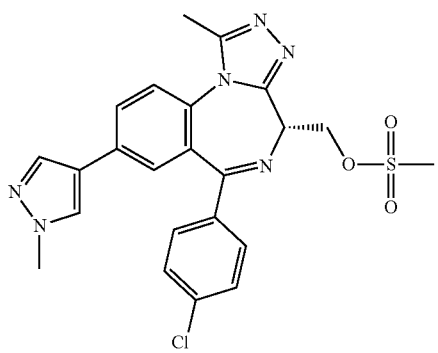

To a solution of (R)-(6-(4-chlorophenyl)-1-methyl-8-(1-methyl-1H-pyrazol-4-yl)-4H-benzo[f][1,2,4]triazolo[4,3-a][1,4]diazepin-4-yl)methanol (23.0 mg, 0.055 mmol) in DCM (0.50 mL) was added MsCl (8.56 μL, 0.115 mmol) followed by TEA (19.1 μL, 0.137 mmol) at 0° C. The reaction mixture was stirred at room temperature for 4 hours. After diluted with DCM, the resulting mixture was washed with 2 N aq. HCl and saturated aq. NaHCO$_3$, dried over Na$_2$SO$_4$, filtered and concentrated in vacuo. The residue was purified by column chromatography on SiO$_2$ (EtOAc:MeOH=10:1) to obtain the title compound (14.0 mg, 52%) as a yellow solid.

$^1$H-NMR (400 MHz, CDCl$_3$): δ 7.78 (d, J=7.6 Hz, 1H), 7.73 (s, 1H), 7.60 (s, 1H), 7.56 (d, J=8.0 Hz, 2H), 7.47 (d, J=8.4 Hz, 1H), 7.46 (s, 1H), 7.37 (d, J=8.0 Hz, 2H), 5.31 (ABX, J$_{AB}$=10.4 Hz, J$_{BX}$=7.0 Hz, 1H), 5.18 (ABX, J$_{AB}$=10.4 Hz, J$_{AX}$=6.6 Hz, 1H), 4.50 (t, J=6.6 Hz, 1H), 3.95 (s, 3H), 3.20 (s, 3H), 2.67 (s, 3H).

LC-MS m/z 497.3 [M+H]$^+$ Rt=3.06 min.

Examples 12 and 13

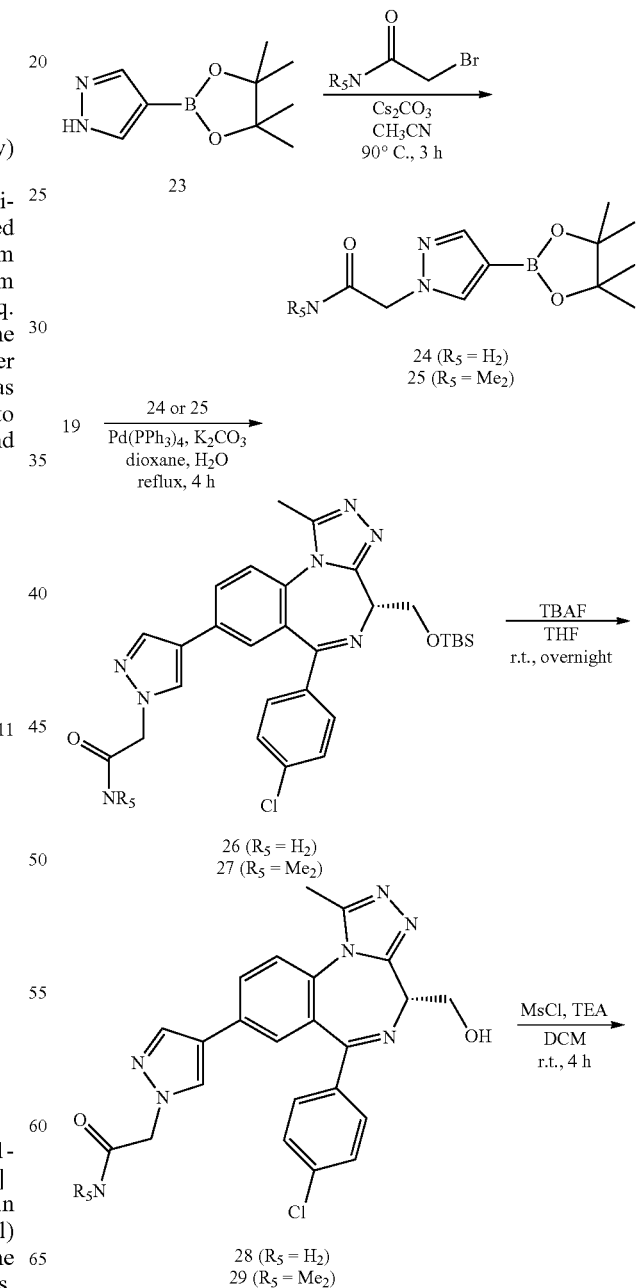

-continued

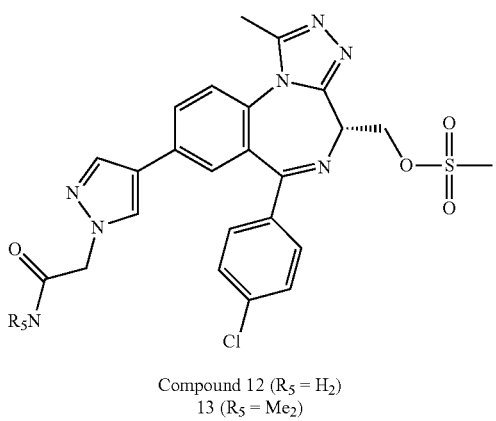

Compound 12 (R₅ = H₂)
13 (R₅ = Me₂)

Example 12: Preparation of (R)-(8-(1-(2-amino-2-oxoethyl)-1H-pyrazol-4-yl)-6-(4-chlorophenyl)-1-methyl-4H-benzo[f][1,2,4]triazolo[4,3-a][1,4]diazepin-4-yl)methyl methanesulfonate (Compound 12)

Step 1: Preparation of 2-(4-(4,4,5,5-tetramethyl-1,3,2-dioxaborolan-2-yl)-1H-pyrazol-1-yl) acetamide (Intermediate 24)

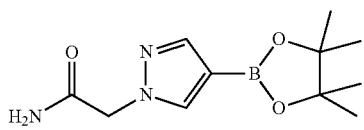

A mixture of 4-(4,4,5,5-tetramethyl-1,3,2-dioxaborolan-2-yl)-1H-pyrazole (200 mg, 1.03 mmol), 2-bromoacetamide (213 mg, 1.54 mmol) and Cs₂CO₃ (1.27 g, 3.92 mmol) in CH₃CN (5.0 mL) was stirred at 90° C. for 3 hours. After being cooled to room temperature, the reaction mixture was diluted with water and extracted with EtOAc twice. The combined organic layers were dried over Na₂SO₄, filtered and concentrated in vacuo to obtain the title compound (174 mg, 67%) as a white solid, which was used for the next reaction without further purification.

¹H-NMR (400 MHz, CDCl₃): δ 7.89 (s, 1H), 7.76 (s, 1H), 6.21 and 5.41 (brs, 2H), 4.83 (s, 2H), 1.32 (s, 12H).

Step 2: Preparation of (R)-2-(4-(4-(((tert-butyldimethylsilyl)oxy)methyl)-6-(4-chlorophenyl)-1-methyl-4H-benzo[f][1,2,4]triazolo[4,3-a][1,4]diazepin-8-yl)-1H-pyrazol-1-yl)acetamide (Intermediate 26)

A dried round bottom flask was charged with (R)-8-bromo-4-(((tert-butyldimethylsilyl)oxy)methyl)-6-(4-chlorophenyl)-1-methyl-4H-benzo[f][1,2,4]triazolo[4,3-a][1,4]diazepine (300 mg, 0.564 mmol), 2-(4-(4,4,5,5-tetramethyl-1,3,2-dioxaborolan-2-yl)-1H-pyrazol-1-yl)acetamide (142 mg, 0.564 mmol), dioxane (2.0 mL) and water (1.0 mL) was evacuated and refilled with nitrogen several times. After addition of Pd(PPh₃)₄ (65.2 mg, 0.056 mmol) and K₂CO₃ (156 mg, 1.13 mmol) to the mixture at room temperature, the reaction mixture was refluxed for 4 hours. After being cooled to room temperature, the reaction mixture was treated with water (5.0 mL) and then filtered through a Celite pad. The filtrate was partitioned between saturated aq. NaHCO₃ (5.0 mL) and DCM (10 mL). The separated aqueous layer was extracted with DCM and the organic layers were washed with brine, dried over Na₂SO₄, filtered and concentrated in vacuo. The residue was purified by column chromatography on SiO₂ (EtOAc/MeOH=10:1) to obtain the title compound (194 mg, 60%) as a yellow solid.

¹H-NMR (400 MHz, CDCl₃): δ 7.85 (s, 1H), 7.75 (dd, J=8.0, 2.0 Hz, 1H), 7.73 (s, 1H), 7.55 (d, J=8.8 Hz, 2H), 7.49-7.44 (m, 2H), 7.35 (d, J=8.4 Hz, 2H), 4.83 (s, 2H), 4.71 (d, J=6.8 Hz, 2H), 4.18 (t, J=6.4 Hz, 1H), 3.73 (s, 2H), 2.64 (s, 3H), 0.94 (s, 9H), 0.20 (s, 3H), 0.16 (s, 3H).

Step 3: Preparation of (R)-2-(4-(6-(4-chlorophenyl)-4-(hydroxymethyl)-1-methyl-4H-benzo[f][1,2,4]triazolo[4,3-a][1,4]diazepin-8-yl)-1H-pyrazol-1-yl)acetamide (Intermediate 28)

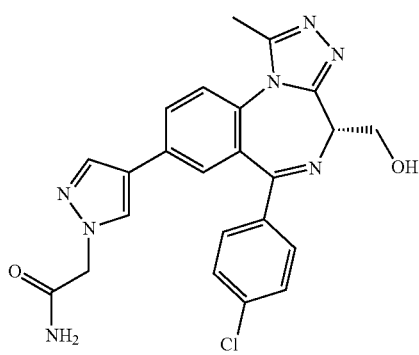

28

To a solution of (R)-2-(4-(4-(((tert-butyldimethylsilyl)oxy)methyl)-6-(4-chlorophenyl)-1-methyl-4H-benzo[f][1,2,4]triazolo[4,3-a][1,4]diazepin-8-yl)-1H-pyrazol-1-yl)acetamide (194 mg, 0.337 mmol) in THF (2.0 mL) was added TBAF (673 µL, 0.673 mmol, 1 M solution in THF) at room temperature. The reaction mixture was stirred at room temperature overnight and quenched with saturated aq. NH$_4$Cl. The mixture was extracted with EtOAc twice. The combined organic layers were washed with brine, dried over Na$_2$SO$_4$, filtered and concentrated in vacuo. The residue was purified by column chromatography on SiO$_2$ (EtOAc only to EtOAc:MeOH=10:1) to obtain the title compound (73.0 mg, 47%) as a yellow solid.

LC/MS m/z 462.32 [M+H]$^+$, Rt=0.20 min.

Step 4: Preparation of (R)-(8-(1-(2-amino-2-oxoethyl)-1H-pyrazol-4-yl)-6-(4-chlorophenyl)-1-methyl-4H-benzo[f][1,2,4]triazolo[4,3-a][1,4]diazepin-4-yl)methyl methanesulfonate (Compound 12)

Compound 12

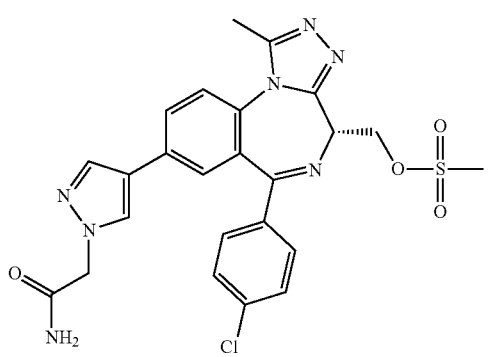

To a solution of (R)-2-(4-(6-(4-chlorophenyl)-4-(hydroxymethyl)-1-methyl-4H-benzo[f][1,2,4]triazolo[4,3-a][1,4]diazepin-8-yl)-1H-pyrazol-1-yl)acetamide (73.0 mg, 0.158 mmol) in DCM (0.80 mL) was added MsCl (24.6 µL, 0.316 mmol) followed by TEA (55.1 µL, 0.395 mmol) at 0° C. The reaction mixture was stirred at room temperature for 12 hours and diluted with DCM. The resulting mixture was washed with 2 N aq. HCl and saturated aq. NaHCO$_3$, dried over Na$_2$SO$_4$, filtered and concentrated in vacuo. The residue was purified by prep-HPLC to obtain the title compound (36.0 mg, 43%) as a white solid.

$^1$H-NMR (400 MHz, CDCl$_3$): δ 7.82 (s, 1H), 7.79 (dd, J=8.6, 1.8 Hz, 1H), 7.75 (s, 1H), 7.53 (d, J=8.4 Hz, 2H), 7.49 (d, J=8.0 Hz, 2H), 7.35 (d, J=8.4 Hz, 2H), 6.32 and 5.78 (brs, 2H), 5.29 (ABX, J$_{AB}$=10.5 Hz, J$_{BX}$=6.1 Hz, 1H), 5.16 (ABX, J$_{AB}$=10.5 Hz, J$_{AX}$=6.7 Hz, 1H), 4.83 (s, 2H), 4.47 (t, J=6.6 Hz, 1H), 3.18 (s, 3H), 2.65 (s, 3H).

LC-MS m/z 540.3 [M+H]$^+$ Rt=2.83 min.

Example 13: Preparation of (R)-(6-(4-chlorophenyl)-8-(1-(2-(dimethylamino)-2-oxoethyl)-1H-pyrazol-4-yl)-1-methyl-4H-benzo[f][1,2,4]triazolo[4,3-a][1,4]diazepin-4-yl)methyl methanesulfonate (Compound 13)

Step 1: Preparation of N,N-dimethyl-2-(4-(4,4,5,5-tetramethyl-1,3,2-dioxaborolan-2-yl)-1H-pyrazol-1-yl)acetamide (Intermediate 25)

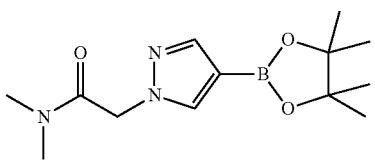

25

A mixture of 4-(4,4,5,5-tetramethyl-1,3,2-dioxaborolan-2-yl)-1H-pyrazole (100 mg, 0.515 mmol), 2-chloro-N,N-dimethylacetamide (58.3 µL, 0.567 mmol) and Cs$_2$CO$_3$ (252 mg, 0.773 mmol) in DMF (3.0 mL) was stirred at 90° C. for 3 hours. After being cooled to room temperature, the reaction mixture was treated with water and extracted with EtOAc twice. The combined organic layers were dried over Na$_2$SO$_4$, filtered and concentrated in vacuo to obtain the title compound (106 mg, 74%) as a white solid, which was used for the next reaction without further purification.

$^1$H-NMR (400 MHz, CDCl$_3$): δ 7.81 (d, J=5.6 Hz, 2H), 4.99 (s, 2H), 3.07 (s, 3H), 2.98 (s, 3H), 1.31 (s, 12H).

Step 2: Preparation of (R)-2-(4-(4-(((tert-butyldimethylsilyl)oxy)methyl)-6-(4-chlorophenyl)-1-methyl-4H-benzo[f][1,2,4]triazolo[4,3-a][1,4]diazepin-8-yl)-1H-pyrazol-1-yl)-N,N-dimethylacetamide (Intermediate 27)

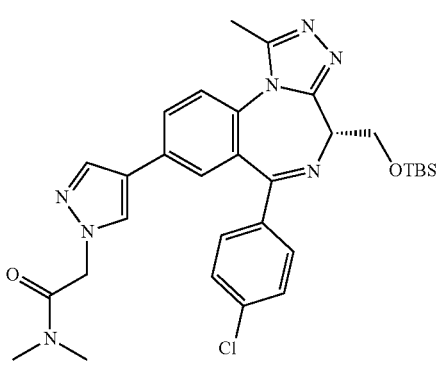

27

The procedure in accordance with Step 2 in Example 12 was repeated except that Intermediate 25 was used instead of Intermediate 24 to obtain the title compound (66.0 mg, 45%) as a yellow solid.

LC/MS m/z 604.48 [M+H]$^+$, Rt=0.28 min.

Step 3: Preparation of (R)-2-(4-(6-(4-chlorophenyl)-4-(hydroxymethyl)-1-methyl-4H-benzo[f][1,2,4]triazolo[4,3-a][1,4]diazepin-8-yl)-1H-pyrazol-1-yl)-N,N-dimethylacetamide (Intermediate 29)

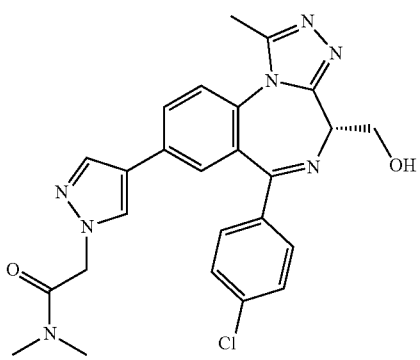

29

The procedure in accordance with Step 3 in Example 12 was repeated except that Intermediate 27 was used instead of Intermediate 26 to obtain the title compound (35 mg, 72%) as a yellow solid.

LC/MS m/z 490.3 [M+H]$^+$, Rt=0.31 min.

Step 4: Preparation of (R)-(6-(4-chlorophenyl)-8-(1-(2-(dimethylamino)-2-oxoethyl)-1H-pyrazol-4-yl)-1-methyl-4H-benzo[f][1,2,4]triazolo[4,3-a][1,4]diazepin-4-yl)methyl methanesulfonate (Compound 13)

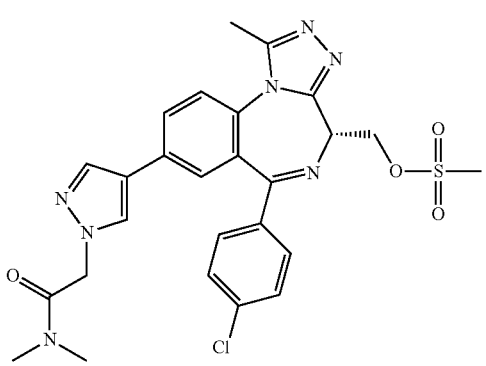

Compound 13

To a solution of (R)-2-(4-(6-(4-chlorophenyl)-4-(hydroxymethyl)-1-methyl-4H-benzo[f][1,2,4]triazolo[4,3-a][1,4]diazepin-8-yl)-1H-pyrazol-1-yl)-N,N-dimethylacetamide (15.0 mg, 0.031 mmol) in DCM (0.5 mL) was added MsCl (4.77 μL, 0.061 mmol) followed by TEA (10.7 μL, 0.077 mmol) at 0° C. The reaction mixture was stirred at room temperature for 3 days and diluted with DCM. The resulting mixture was washed with 2 N aq. HCl and saturated aq. NaHCO$_3$, dried over Na$_2$SO$_4$, filtered and concentrated in vacuo. The residue was purified by column chromatography on SiO$_2$ (EtOAc:MeOH=10:1) to obtain the title compound (11.9 mg, 68%) as a yellow solid.

$^1$H-NMR (400 MHz, CDCl$_3$): δ 7.82-7.76 (m, 3H), 7.55 (d, J=8.4 Hz, 2H), 7.50 (d, J=3.6 Hz, 1H), 7.48 (d, J=8.4 Hz, 1H), 7.37 (d, J=8.4 Hz, 2H), 5.32 (ABX, J$_{AB}$=10.2 Hz, J$_{BX}$=6.8 Hz, 1H), 5.18 (ABX, J$_{AB}$=10.2 Hz, J$_{AX}$=7.2 Hz, 1H), 5.02 (s, 2H), 4.49 (t, J=6.8 Hz, 1H), 3.21 (s, 3H), 3.12 (s, 3H), 3.01 (s, 3H), 2.67 (s, 3H).

LC-MS m/z 568.3 [M+H]$^+$ Rt=2.71 min.

Example 14: Preparation of (R)-(6-(4-chlorophenyl)-8-((2-hydroxyethyl)carbamoyl)-1-methyl-4H-benzo[f][1,2,4]triazolo[4,3-a][1,4]diazepin-4-yl)methyl methanesulfonate (Compound 14)

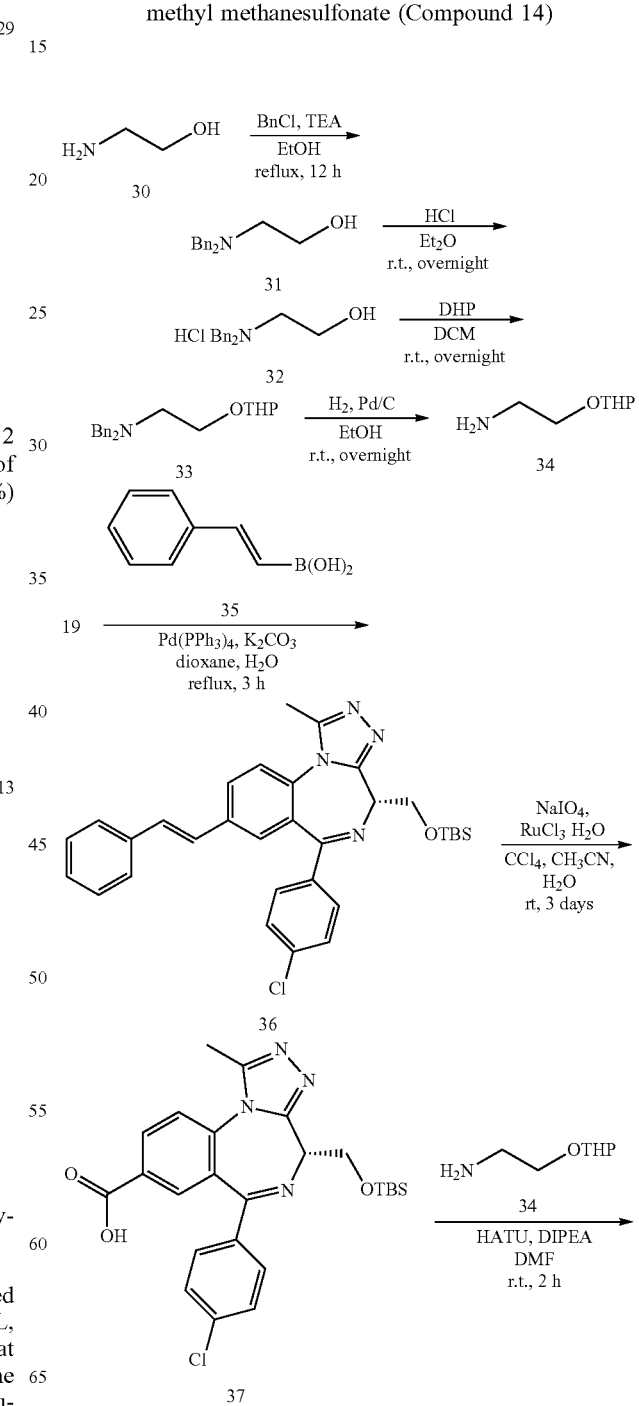

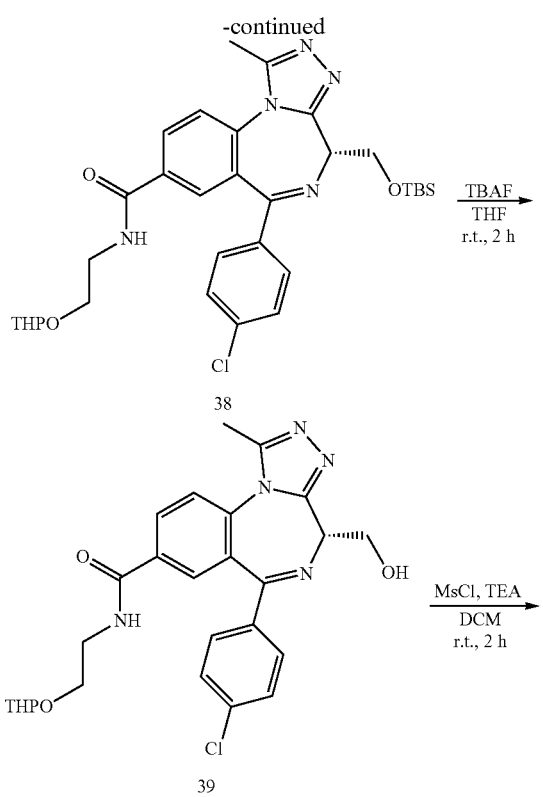

Step 1: Preparation of 2-(dibenzylamino ethanol (Intermediate 31)

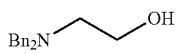

To a solution of 2-aminoethanol (500 mg, 8.19 mmol) and TEA (2.74 mL, 19.7 mmol) in EtOH (11 mL) was added benzyl chloride (1.90 mL, 16.4 mmol) in EtOH (2.0 mL) at room temperature. The reaction mixture was refluxed for 12 hours. After evaporation of volatiles, the residue was diluted with diethyl ether. The mixture was extracted with diluted with diethyl ether and extracted with 2 N aq. HCl. The separated aqueous layer was neutralized with $Na_2CO_3$ and extracted with diethyl ether. The separated organic layer was dried over $Na_2SO_4$, filtered and concentrated in vacuo to obtain the title compound (980 mg, 50%), which was used for the next reaction without further purification.

$^1$H-NMR (400 MHz, $CDCl_3$): δ 7.36-7.15 (m, 10H), 3.63 (s, 4H), 3.58 (t, J=5.2 Hz, 2H), 2.67 (t, J=5.2 Hz, 2H) *OH peak was not observed.

Step 2: Preparation of 2-(dibenzylamino)ethanol hydrochloride (Intermediate 32)

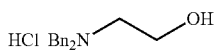

To a solution of 2-(dibenzylamino)ethanol (980 mg, 4.06 mmol) in diethyl ether (1.0 mL) was added HCl (2 M solution in ether, 2.0 mL) at 0° C. The reaction mixture was stirred at room temperature overnight and then concentrated in vacuo to obtain the title compound (980 mg, 87%) as a white solid, which was used for the next reaction without further purification.

$^1$H-NMR (400 MHz, $D_2O$): δ 7.40-7.21 (m, 10H), 4.27 (s, 4H), 3.72 (t, J=5.0 Hz, 2H), 3.13 (t, J=5.0 Hz, 2H) *2HCl and OH peaks were not observed.

Step 3: Preparation of N,N-dibenzyl-2-(tetrahydro-2H-pyran-2-yloxy)ethanamine (Intermediate 33)

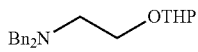

To a solution of 2-(dibenzylamino)ethanol hydrochloride (980 mg, 3.55 mmol) in DCM (5.0 mL) was added dropwise 3,4-dihydro-2H-pyran (DHP) (485 μL, 5.32 mmol). The reaction mixture was stirred at room temperature overnight and then poured into saturated aq. $Na_2CO_3$. The aqueous layer was extracted with DCM, dried over $Na_2SO_4$ and concentrated to in vacuo to obtain the title compound (1.00 g, 87%), which was used in the next step without purification.

$^1$H-NMR (400 MHz, $CDCl_3$): δ 7.58-7.12 (m, 10H), 4.57 (s, 1H), 3.94-3.79 (m, 2H), 3.67 (brs, 4H), 3.58-3.43 (m, 2H), 2.71 (brs, 2H), 1.64-1.42 (m, 6H).

Step 4: Preparation of 2-(tetrahydro-2H-pyran-2-yloxy)ethanamine (Intermediate 34)

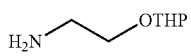

34

A suspension of N,N-dibenzyl-2-(tetrahydro-2H-pyran-2-yloxy)ethanamine (1.00 g, 3.07 mmol) and Pd/C (5 wt %, 327 mg, 0.154 mmol) in EtOH (15 mL) was stirred at room temperature overnight under hydrogen atmosphere (balloon). After filtration through a Celite pad, the filtrate was concentrated in vacuo to give the title compound (430 mg, 96%) as colorless oil, which was used for the next step without further purification.

$^1$H-NMR (400 MHz, CDCl$_3$): δ 4.60 (brs, 1H), 3.93-3.84 (m, 1H), 3.83-3.76 (m, 1H), 3.56-3.44 (m, 2H), 2.92 (t, J=5.2 Hz, 2H), 2.29 (brs, 2H), 1.65-1.46 (m, 6H).

Step 5: Preparation of (R,E)-4-(((tert-butyldimethylsilyl)oxy)methyl)-6-(4-chlorophenyl)-1-methyl-8-styryl-4H-benzo[f][1,2,4]triazolo[4,3-a][1,4]diazepine (Intermediate 36)

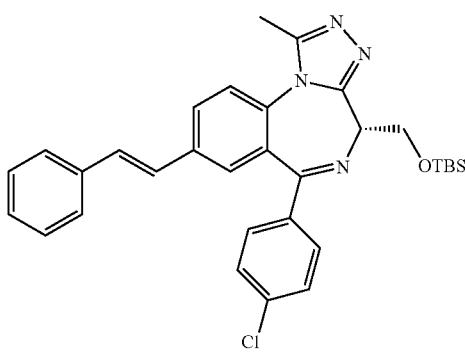

36

A dried round bottom flask was charged with (R)-8-bromo-4-(((tert-butyldimethylsilyl)oxy)methyl)-6-(4-chlorophenyl)-1-methyl-4H-benzo[f][1,2,4]triazolo[4,3-a][1,4]diazepine (Intermediate 19, 460 mg, 0.865 mmol), (E)-styrylboronic acid (256 mg, 1.73 mmol), dioxane (3.0 mL) and water (1.5 mL) was evacuated and refilled with nitrogen several times. After addition of Pd(PPh$_3$)$_4$ (100 mg, 0.0860 mmol), and K$_2$CO$_3$ (239 mg, 1.73 mmol) to the mixture, the reaction mixture was refluxed for 3 hours. After being cooled to room temperature, the reaction mixture was treated with water (5.0 mL) and then filtered through a Celite pad. The filtrate was partitioned between saturated aq. NaHCO$_3$ (5.0 mL) and DCM (10 mL). The separated aqueous layer was extracted with DCM, and the organic layers were washed with brine, dried over Na$_2$SO$_4$, filtered and concentrated in vacuo. The residue was purified by column chromatography on SiO$_2$ (EtOAc:MeOH=10:1) to obtain the title compound (389 mg, 81%) as a brown solid.

$^1$H-NMR (400 MHz, CDCl$_3$): δ 7.82 (d, J=8.8 Hz, 1H), 7.57 (d, J=8.4 Hz, 2H), 7.53-7.48 (m, 3H), 7.45 (d, J=8.4 Hz, 1H), 7.41-7.34 (m, 4H), 7.32 (d, J=6.8 Hz, 1H), 7.09 (d, J=7.6 Hz, 2H), 4.72 (d, J=6.8 Hz, 2H), 4.20 (t, J=6.6 Hz, 1H), 0.95 (s, 9H), 2.66 (s; 3H), 0.21 (s, 3H), 0.18 (s, 3H).

Step 6: Preparation of (R)-4-(((tert-butyldimethylsilyl)oxy)methyl)-6-(4-chlorophenyl)-1-methyl-4H-benzo[f][1,2,4]triazolo[4,3-a][1,4]diazepine-8-carboxylic acid (Intermediate 37)

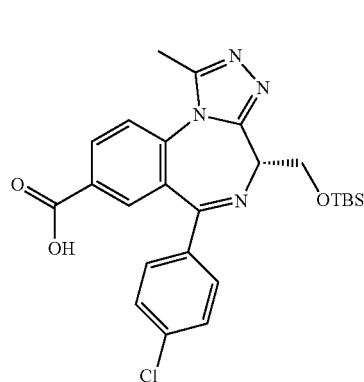

37

To a solution of (R,E)-4-(((tert-butyldimethylsilyl)oxy)methyl)-6-(4-chlorophenyl)-1-methyl-8-styryl-4H-benzo[f][1,2,4]triazolo[4,3-a][1,4]diazepine (310 mg, 0.558 mmol) in CCl$_4$ (0.80 mL), CH$_3$CN (0.80 mL) and water (1.2 mL) was added NaIO$_4$ (478 mg, 2.23 mmol) and ruthenium (III) chloride (3.94 mg, 0.0150 mmol) at room temperature. The reaction mixture was stirred for 3 days at room temperature. The reaction mixture was extracted with DCM twice, and the separated organic layers were washed with brine, dried over Na$_2$SO$_4$, filtered and concentrated in vacuo. The residue was purified by column chromatography on SiO$_2$ (EtOAc:MeOH=5:1) to obtain the title compound (70.0 mg, 25%) as a brown solid.

$^1$H-NMR (400 MHz, CDCl$_3$): δ 8.38 (d, J=8.0 Hz, 1H), 8.18 (s, 1H), 7.57 (d, J=8.0 Hz, 1H), 7.51 (d, J=8.0 Hz, 2H), 7.36 (d, J=8.4 Hz, 2H), 4.72 (d, J=6.8 Hz, 2H), 4.17 (t, J=6.4 Hz, 1H), 2.69 (s, 3H), 0.94 (s, 9H), 0.20 (s, 3H), 0.17 (s, 3H).

*COOH peak was not observed.

Step 7: Preparation of (4R)-2-((tetrahydro-2H-pyran-2-yl)oxy)ethyl 4-(((tert-butyldimethylsilyl)oxy)methyl)-6-(4-chlorophenyl)-1-methyl-4H-benzo[f][1,2,4]triazolo[4,3-a][1,4]diazepine-8-carboxylate (Intermediate 38)

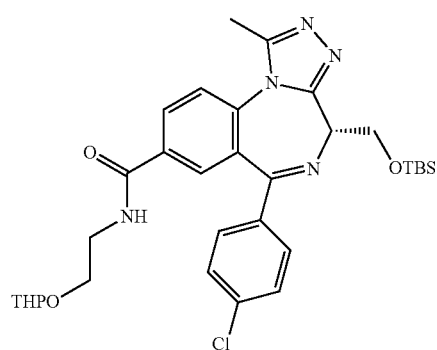

38

To a solution of (R)-4-(((tert-butyldimethylsilyl)oxy)methyl)-6-(4-chlorophenyl)-1-methyl-4H-benzo[f][1,2,4]triazolo[4,3-a][1,4]diazepine-8-carboxylic acid (70.0 mg, 0.141 mmol) in DMF (0.70 mL) was added 2-(tetrahydro-2H-pyran-2-yloxy)ethanamine (30.7 mg, 0.211 mmol), (1-[Bis(dimethylamino)methylene]-1H-1,2,3-triazolo[4,5-b]pyridinium 3-oxid hexafluorophosphate) (HATU) (80.0 mg, 0.211 mmol) and N,N-diisopropylethylamine (DIPEA) (36.9 μL, 0.211 mmol) at room temperature. The resulting mixture was stirred for 2 hours at room temperature. After concentration of the mixture in vacuo, the residue was diluted with EtOAc, washed with water and brine, dried over $Na_2SO_4$, filtered and concentrated in vacuo. The residue was purified by column chromatography on $SiO_2$ (Hex:EtOAc=10:1) to obtain the title compound (44.0 mg, 50%) as a yellow solid.

$^1$H-NMR (400 MHz, $CDCl_3$): δ 8.16 (d, J=8.8 Hz, 1H), 7.84 (s, 1H), 7.55 (d, J=8.4 Hz, 1H), 7.51 (d, J=8.4 Hz, 2H), 7.35 (d, J=7.6 Hz, 2H), 7.18 (d, J=14.8 Hz, 1H), 4.71 (d, J=7.2 Hz, 2H), 4.91 (s, 1H), 4.13 (t, J=7.4 Hz, 1H), 3.91-3.84 (m, 1H), 3.83-3.72 (m, 2H), 3.71-3.63 (m, 1H), 3.60-3.51 (m, 1H), 3.45-3.35 (m, 1H), 2.65 (s, 3H), 1.56-1.44 (m, 6H), 0.94 (s, 9H), 0.20 (s, 3H), 0.16 (s, 3H).

Step 8: Preparation of (4R)-2-((tetrahydro-2H-pyran-2-yl)oxy)ethyl 6-(4-chlorophenyl)-4-(hydroxymethyl)-1-methyl-4H-benzo[f][1,2,4]triazolo[4,3-a][1,4]diazepine-8-carboxylate (Intermediate 39)

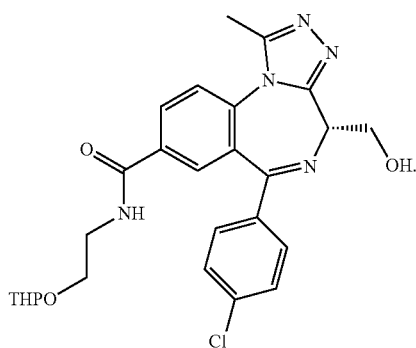

39

To a solution of (4R)-2-((tetrahydro-2H-pyran-2-yl)oxy) ethyl 4-(((tert-butyldimethylsilyl)oxy)methyl)-6-(4-chlorophenyl)-1-methyl-4H-benzo[f][1,2,4]triazolo[4,3-a][1,4]diazepine-8-carboxylate (44.0 mg, 0.0700 mmol) in THF (0.35 mL) was added TBAF (141 μL, 0.141 mmol, 1 M solution in THF) at room temperature. The reaction mixture was stirred at room temperature for 2 hours and quenched with saturated aq. $NH_4Cl$. The mixture was extracted with EtOAc twice. The combined organic layers were washed with brine, dried over $Na_2SO_4$, filtered and concentrated in vacuo. The residue was purified by column chromatography on $SiO_2$ (EtOAc only to EtOAc:MeOH=9:1) to obtain the title compound (30.0 mg, 83%) as a yellow solid.

LC/MS m/z 510.23 [M+H]$^+$, Rt=0.31 min

Step 9: Preparation of (4R)-2-((tetrahydro-2H-pyran-2-yl)oxy)ethyl 6-(4-chlorophenyl)-1-methyl-4-(((methylsulfonyl)oxy)methyl)-4H-benzo[f][1,2,4]triazolo[4,3-a][1,4]diazepine-8-carboxylate (Intermediate 40)

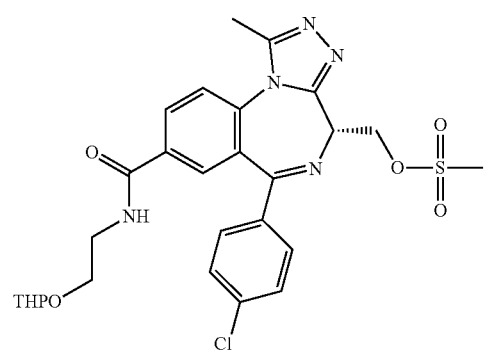

40

To a solution of (4R)-2-((tetrahydro-2H-pyran-2-yl)oxy) ethyl 6-(4-chlorophenyl)-4-(hydroxymethyl)-1-methyl-4H-benzo[f][1,2,4]triazolo[4,3-a][1,4]diazepine-8-carboxylate (30.0 mg, 0.0590 mmol) in DCM (0.30 mL) was added MsCl (9.17 μL, 0.118 mmol) followed by TEA (20.5 μL, 0.147 mmol) at 0° C. The reaction mixture was stirred at room temperature for 2 hours and diluted with DCM. The resulting mixture was washed with 2 N aq. HCl and saturated aq. $NaHCO_3$, dried over $Na_2SO_4$, filtered and concentrated in vacuo. The residue was purified by column chromatography on $SiO_2$ (EtOAc only to EtOAc:MeOH=9:1) to obtain the title compound (30.0 mg, 87%) as a yellow foam.

LC/MS m/z 588.2 [M+H]$^+$, Rt=0.42 min.

Step 10: Preparation of (R)-(6-(4-chlorophenyl)-8-((2-hydroxyethyl)carbamoyl)-1-methyl-4H-benzo[f][1,2,4]triazolo[4,3-a][1,4]diazepin-4-yl)methyl methanesulfonate (Compound 14)

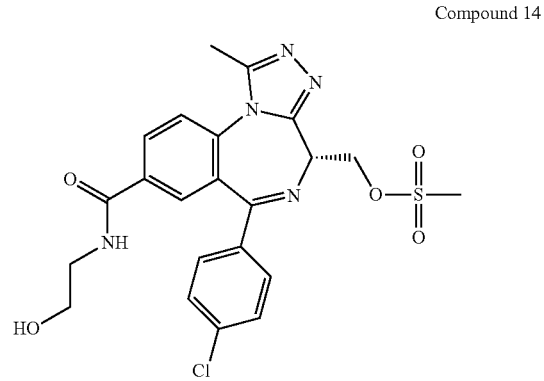 [SMILES: Cc1nnc2n1-c1ccc(C(=O)NCCO)cc1C(c1ccc(Cl)cc1)=N[C@H]2COS(C)(=O)=O]

Compound 14

To a solution of (4R)-2-((tetrahydro-2H-pyran-2-yl)oxy) ethyl 6-(4-chlorophenyl)-1-methyl-4-(((methylsulfonyl) oxy)methyl)-4H-benzo[f][1,2,4]triazolo[4,3-a][1,4]diazepine-8-carboxylate (30.0 mg, 0.0510 mmol) in MeOH (0.26 mL) was added p-toluenesulfonic acid (p-TsOH) (0.97 mg, 5.10 μmol) at room temperature. The reaction mixture was stirred at room temperature for 2 hours and diluted with DCM. The resulting mixture was washed with saturated aq. NaHCO₃, dried over Na₂SO₄, filtered and concentrated in vacuo. The residue was purified by prep-HPLC to obtain the title compound (5.8 mg, 23%) as yellow foam.

¹H-NMR (400 MHz, CDCl₃): δ 8.27 (d, J=8.4 Hz, 1H), 7.98 (s, 1H), 7.91 (d, J=8.8 Hz, 1H), 7.59 (d, J=8.4 Hz, 2H), 7.44 (d, J=8.0 Hz, 2H), 5.13 (d, J=6.4 Hz, 2H), 4.58 (t, J=6.4 Hz, 1H), 3.68 (t, J=5.6 Hz, 2H), 3.48 (t, J=5.4 Hz, 2H), 3.23 (s, 3H), 2.69 (s, 3H). *OH and NH peaks were not observed. LC-MS m/z 504.1 [M+H]⁺ Rt=3.03 min.

Example 15: Preparation of (R)-(4-(4-chlorophenyl)-2,3,9-trimethyl-6H-thieno[3,2-f][1,2,4]triazolo[4,3-a][1,4]diazepin-6-yl)methyl methanesulfonate (Compound 15)

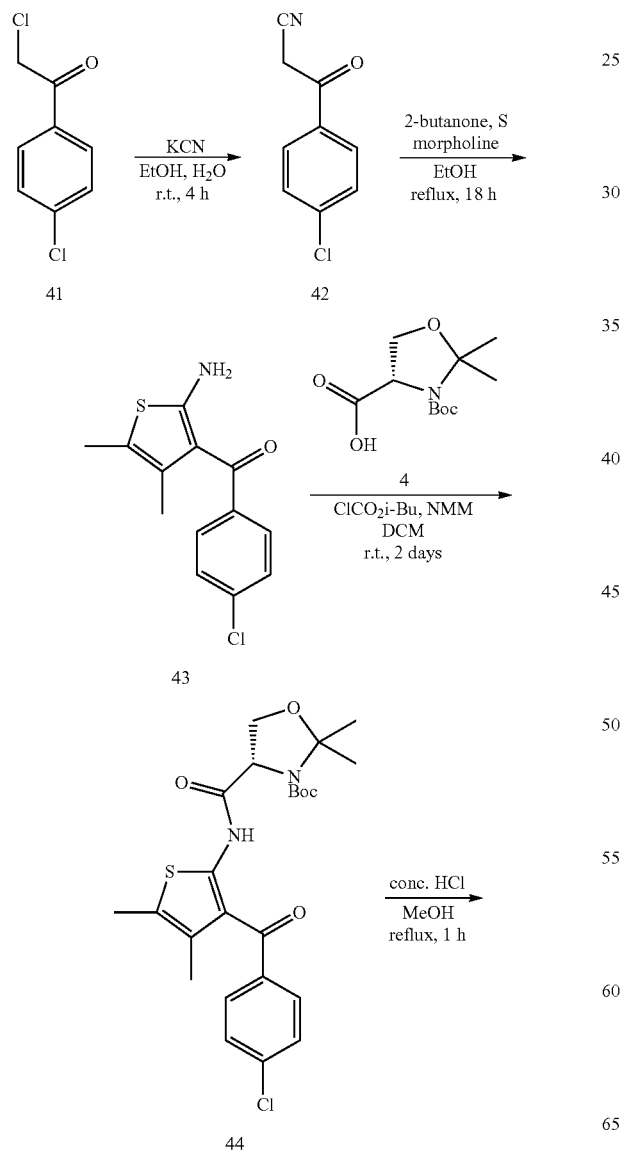

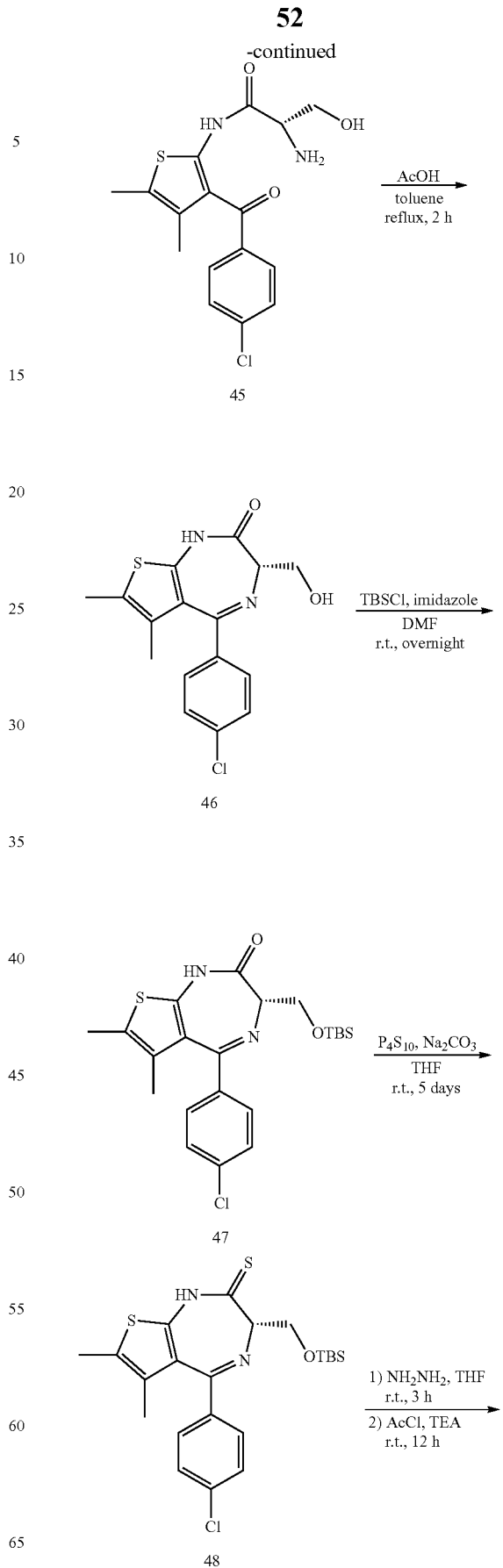

53

-continued

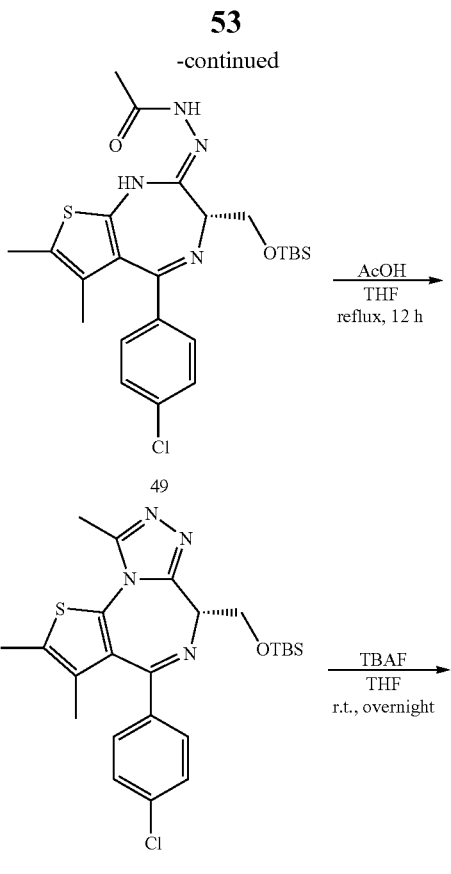

49

50

51

Compound 15

54

Step 1: Preparation of
3-(4-chlorophenyl)-3-oxopropanenitrile
(Intermediate 42)

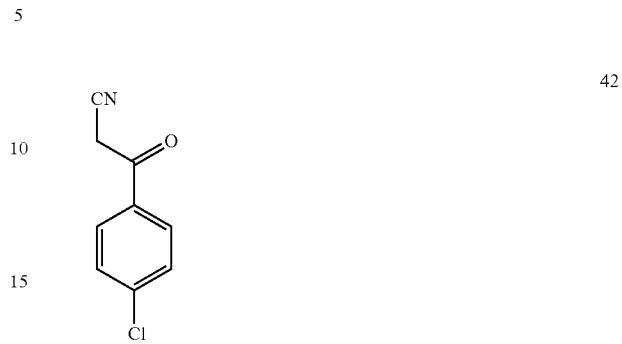

42

To a solution of 2-chloro-1-(4-chlorophenyl)ethanone (15.5 g, 66.4 mmol) in EtOH (101 mL) was added a solution of KCN (10.8 g, 166 mmol) in water (10 mL). The reaction mixture was stirred at room temperature for 4 hours, then diluted with water and DCM. The mixture was treated with acetic acid (20 mL). The separated organic layer was washed with brine, dried over $Na_2SO_4$, filtered and concentrated in vacuo to give the title compound (11.8 g, 99%) as a yellow solid.

$^1$H-NMR (400 MHz, $CDCl_3$): δ 7.88 (d, J=8.4 Hz, 2H), 7.52 (d, J=8.4 Hz, 2H), 4.06 (s, 2H).

Step 2: Preparation of (2-amino-4,5-dimethylthiophen-3-yl)(4-chlorophenyl)methanone (Intermediate 43)

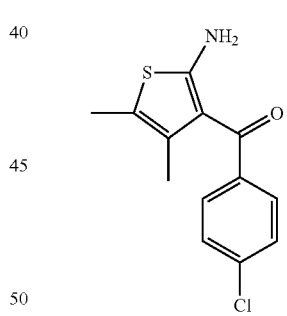

43

To a solution of 3-(4-chlorophenyl)-3-oxopropanenitrile (12.0 g, 66.8 mmol), 2-butanone (5.98 mL, 66.8 mmol) and morpholine (5.82 mL, 66.8 mmol) in EtOH (191 mL) was added sulfur (2.14 g, 66.8 mmol) at room temperature. The reaction mixture was refluxed for 18 hours, cooled to room temperature and poured into water. The mixture was extracted with EtOAc twice. The combined organic layers were dried over $Na_2SO_4$, filtered and concentrated in vacuo. The residue was purified by column chromatography on $SiO_2$ (Hex:EtOAc=1:1) to obtain the title compound (8.97 g, 51%) as a yellow solid.

$^1$H-NMR (400 MHz, $CDCl_3$): δ 7.47 (d, J=8.4 Hz, 2H), 7.38 (d, J=8.4 Hz, 2H), 6.43 (brs, 2H), 2.14 (s, 3H), 1.56 (s, 3H).

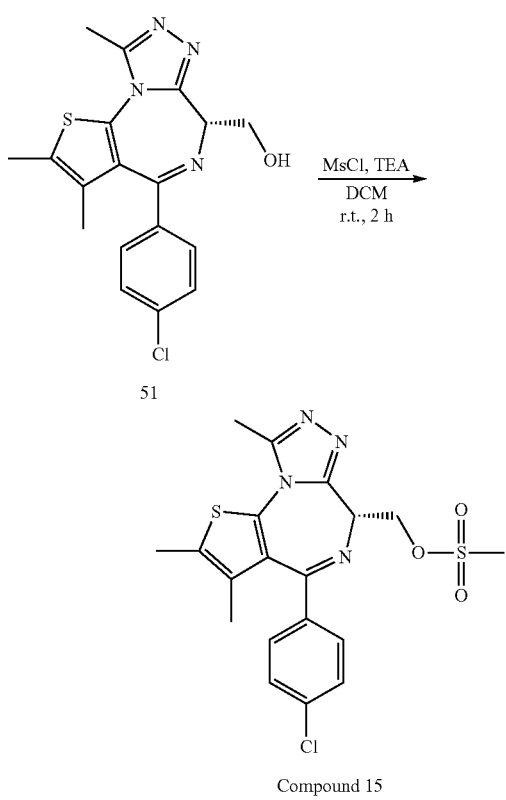

Step 3: Preparation of (S)-tert-butyl-4-(3-(4-chlorobenzoyl)-4,5-dimethylthiophen-2-ylcarbamoyl)-2,2-dimethyloxazolidine-3-carboxylate (Intermediate 44)

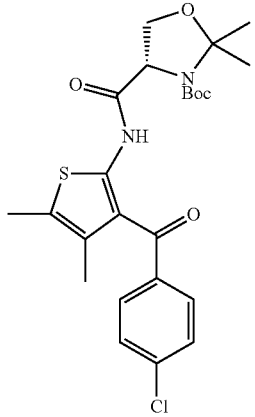

44

To a solution of (S)-3-(tert-butoxycarbonyl)-2,2-dimethyloxazolidine-4-carboxylic acid (Intermediate 4, 0.886 g, 3.61 mmol) in DCM (9 mL) was added N-methylmorpholine (NMM) (0.397 mL, 3.61 mmol) followed by isobutyl chloroformate (0.474 mL, 3.61 mmol) at 0° C. The mixture was stirred for 30 min at room temperature. After addition of (2-amino-4,5-dimethylthiophen-3-yl)(4-chlorophenyl)methanone (Intermediate 43, 0.800 g, 3.01 mmol) to the mixture, the reaction mixture was stirred for 2 days at room temperature. The reaction mixture was diluted with DCM, washed with 2 N aq. HCl, saturated aq. NaHCO₃ and water, dried over Na₂SO₄, filtered and concentrated in vacuo. The residue was purified by column chromatography on SiO₂ (Hex:EtOAc=5:1 to 3:1 to 1:1) to obtain the title compound (1.80 g, 88%) as a viscous yellow oil.

$^1$H-NMR (400 MHz, CDCl₃): (two sets from rotamers) δ 11.4 (brs, 1H), 7.53 (d, J=8.0 Hz, 2H), 7.41 (d, J=8.4 Hz, 2H), 4.65-4.13 (m, 3H), 2.26 (s, 3H), 1.84 and 1.79 (s and s, 3H), 1.68 (s, 3H), 1.57 and 1.56 (s and s, 4H), 1.47 (s, 3H), 1.29-1.24 (m, 5H).

Step 4: Preparation of (S)-2-amino-N-(3-(4-chlorobenzoyl)-4,5-dimethylthiophen-2-yl)-3-hydroxypropanamide (Intermediate 45)

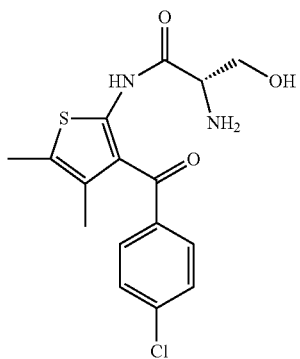

45

To a solution of (S)-tert-butyl-4-(3-(4-chlorobenzoyl)-4,5-dimethylthiophen-2-ylcarbamoyl)-2,2-dimethyloxazolidine-3-carboxylate (1.30 g, 2.64 mmol) in MeOH (13 mL) was added conc. HCl (2.64 mL, 4.34 mmol) at room temperature. The reaction mixture was refluxed for 1 hour and then concentrated in vacuo. The residue was diluted with EtOAc and washed with saturated aq. NaHCO₃ and brine, dried over Na₂SO₄, filtered and concentrated in vacuo to obtain the title compound (770 mg, 82%) as a yellow solid, which was used for the next reaction without further purification.

$^1$H-NMR (400 MHz, CDCl₃): δ 12.1 (s, 1H), 7.59 (d, J=8.0 Hz, 2H), 7.43 (d, J=8.4 Hz, 2H), 4.03 (dd, J=10.6, 5.0 Hz, 1H), 3.82 (dd, J=10.6, 5.4 Hz, 1H), 3.65 (t, J=4.8 Hz, 1H), 2.28 (s, 3H), 1.72 (s, 3H). *Three protons from NH₂ and OH were not observed.

Step 5: Preparation of (S,Z)-5-(4-chlorophenyl)-3-(hydroxymethyl)-6,7-dimethyl-1H-thieno[2,3-e][1,4]diazepin-2(3H)-one (Intermediate 46)

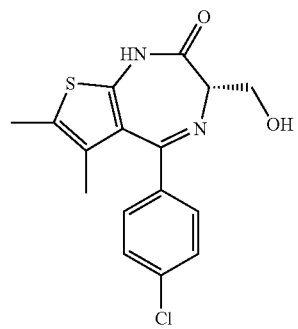

46

A mixture of (S)-2-amino-N-(3-(4-chlorobenzoyl)-4,5-dimethylthiophen-2-yl)-3-hydroxypropanamide (770 mg, 2.18 mmol) and acetic acid (AcOH) (3.12 mL, 54.6 mmol) in toluene (10 mL) was refluxed for 2 hours and then concentrated in vacuo to obtain the title compound (723 mg, 99%) as a yellow solid, which was used for the next reaction without further purification.

LC/MS m/z 335.1[M+H]⁺, Rt=0.46 min.

Step 6: Preparation of (S,Z)-3-((tert-butyldimethylsilyloxy)methyl)-5-(4-chlorophenyl)-6,7-dimethyl-1H-thieno[2,3-e][1,4]diazepin-2(3H)-one (Intermediate 47)

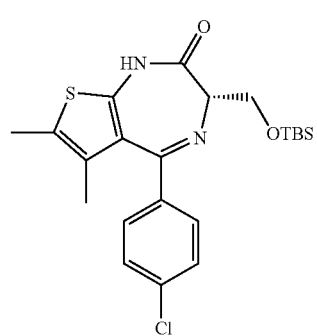

47

To a solution of (S,Z)-5-(4-chlorophenyl)-3-(hydroxymethyl)-6,7-dimethyl-1H-thieno-[2,3-e][1,4]diazepin-2(3H)-one (723 mg, 2.16 mmol) in DMF (11 mL) was added imidazole (250 mg, 3.67 mmol) followed by TBDMS-Cl (488 mg, 3.24 mmol) at room temperature. The reaction mixture was stirred at room temperature overnight. After concentration in vacuo, the residue was diluted with EtOAc, washed with 2 N aq. HCl, saturated aq. NaHCO$_3$, water and brine successively, dried over Na$_2$SO$_4$, filtered and concentrated in vacuo. The residue was purified by column chromatography on SiO$_2$ (Hex:EtOAc=7:1 to 5:1 to 3:1) to obtain the title compound (417 mg, 43%) as a white solid.

$^1$H-NMR (400 MHz, CDCl$_3$): δ 8.30 (s, 1H), 7.46 (d, J=8.8 Hz, 2H), 7.34 (d, J=8.4 Hz, 2H), 4.58 (dd, J=10.4, 7.2 Hz, 1H), 4.26 (dd, J=10.4, 6.0 Hz, 1H), 3.86 (t, J=6.6 Hz, 1H), 2.29 (s, 3H), 1.60 (s, 3H), 0.93 (s, 9H), 0.16 (s, 3H), 0.14 (s, 3H).

Step 7: Preparation of (S,Z)-3-((tert-butyldimethylsilyloxy)methyl)-5-(4-chlorophenyl)-6,7-dimethyl-1H-thieno[2,3-e][1,4]diazepine-2(3H)-thione (Intermediate 48)

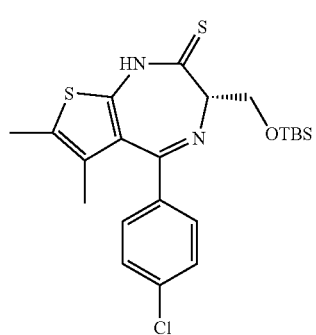

48

A mixture of P$_4$S$_{10}$ (206 mg, 0.464 mmol) and sodium carbonate (49.2 mg, 0.464 mmol) in THF (5 mL) was stirred for 1 hour at room temperature and cooled to 0° C. After addition of a solution of (S,Z)-3-((tert-butyldimethylsilyloxy)methyl)-5-(4-chlorophenyl)-6,7-dimethyl-1H-thieno[2,3-e][1,4]diazepin-2(3H)-one (417 mg, 0.929 mmol) in THF (1.0 mL) to the mixture, the reaction mixture was stirred at 0° C. for 30 min and then for 5 days at room temperature. After filtration through a Celite pad, the filtrate was concentrated in vacuo. The residue was dissolved in EtOAc, washed with saturated aq. NaHCO$_3$ twice and brine, dried over Na$_2$SO$_4$, filtered and concentrated in vacuo. The residue was purified by column chromatography on SiO$_2$ (Hex:EtOAc=5:1) to obtain the title compound (90.0 mg, 21%) as a viscous oil.

$^1$H-NMR (400 MHz, CDCl$_3$): δ 9.89 (brs, 1H), 7.45 (d, J=8.0 Hz, 2H), 7.35 (d, J=8.0 Hz, 2H), 4.67 (dd, J=10.2, 5.4 Hz, 1H), 4.44 (dd, J=9.4, 7.4 Hz, 1H), 4.00 (t, J=6.0 Hz, 1H), 2.31 (s, 3H), 1.62 (s, 3H), 0.93 (s, 9H), 0.18 (s, 3H), 0.16 (s, 3H).

Step 8: Preparation of (Z)—N'—((R,Z)-3-((tert-butyldimethylsilyloxy)methyl)-5-(4-chlorophenyl)-6,7-dimethyl-1H-thieno[2,3-e][1,4]diazepin-2(3H)-ylidene)acetohydrazide (Intermediate 49)

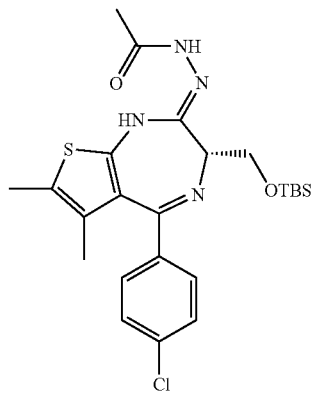

49

To a solution of (S,Z)-3-((tert-butyldimethylsilyloxy)methyl)-5-(4-chlorophenyl)-6,7-dimethyl-1H-thieno[2,3-e][1,4]diazepine-2(3H)-thione (202 mg, 0.434 mmol) in THF (2.0 mL) was added hydrazine monohydrate (82.0 μL, 2.61 mmol) at 0° C. The reaction mixture was stirred for 3 hours at room temperature and cooled to 0° C. After addition of TEA (363 μL, 2.61 mmol) followed by acetyl chloride (185 μL, 2.61 mmol) to the mixture, the reaction mixture was stirred at room temperature for 12 hours. After concentration in vacuo, the residue was dissolved in DCM and washed with water. The separated organic layer was dried over Na$_2$SO$_4$, filtered and concentrated in vacuo to obtain the title compound (204 mg, 93%) as a white solid, which was used for the next reaction without further purification.

LC/MS m/z 505.2 [M+H]$^+$, Rt=0.29 min

Step 9: Preparation of (R)-6-(((tert-butyldimethylsilyl)oxy)methyl)-4-(4-chlorophenyl)-2,3,9-trimethyl-6H-thieno[3,2-f][1,2,4]triazolo[4,3-a][1,4]diazepine (Intermediate 50)

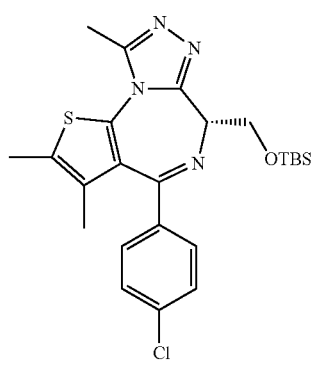

50

A mixture of (Z)—N'—((R,Z)-3-((tert-butyldimethylsilyloxy)methyl)-5-(4-chlorophenyl)-6,7-dimethyl-1H-thieno[2,3-e][1,4]diazepin-2(3H)-ylidene)acetohydrazide (204 mg, 0.404 mmol) and acetic acid (763 μL, 13.3 mmol) in THF (2.0 mL) was refluxed for 12 hours. After concentration in vacuo, the residue was diluted with EtOAc, washed with saturated aq. NaHCO$_3$, dried over Na$_2$SO$_4$, filtered and concentrated in vacuo to obtain the title compound (195 mg, 92%) as a viscous yellow oil, which was used for the next reaction without further purification.

$^1$H-NMR (400 MHz, CDCl$_3$): δ 7.46 (d, J=8.4 Hz, 2H), 7.34 (d, J=8.0 Hz, 2H), 4.75-4.68 (m, 2H), 4.18 (dd, J=7.2, 5.6 Hz, 1H), 2.67 (s, 3H), 2.41 (s, 3H), 1.70 (s, 3H), 0.95 (s, 9H), 0.21 (s, 3H), 0.18 (s, 3H).

Step 10: Preparation of (R)-(4-(4-chlorophenyl)-2,3,9-trimethyl-6H-thieno[3,2-f][1,2,4]triazolo[4,3-a][1,4]diazepin-6-yl)methanol (Intermediate 51)

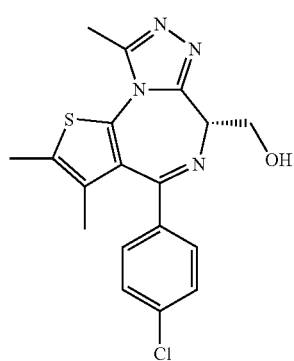

51

To a solution of (R)-6-(((tert-butyldimethylsilyl)oxy)methyl)-4-(4-chlorophenyl)-2,3,9-trimethyl-6H-thieno[3,2-f][1,2,4]triazolo[4,3-a][1,4]diazepine (195 mg, 0.402 mmol) in THF (2.0 mL) was added TBAF (805 μL, 0.805 mmol, 1 M solution in THF) at room temperature. The reaction mixture was stirred at room temperature overnight and quenched with saturated aq. NH$_4$Cl. The mixture was extracted with EtOAc twice. The combined organic layers were washed with brine, dried over Na$_2$SO$_4$, filtered and concentrated in vacuo. The residue was purified by column chromatography on SiO$_2$ (EtOAc only to EtOAc:MeOH=10:1) to obtain the title compound (110 mg, 73%) as a white solid.

$^1$H-NMR (400 MHz, CDCl$_3$): δ 7.46 (d, J=8.4 Hz, 2H), 7.35 (d, J=8.0 Hz, 2H), 4.66 (dd, J=11.2, 7.2 Hz, 1H), 4.54 (dd, J=11.6, 5.6 Hz, 1H), 4.26 (t, J=6.2 Hz, 1H), 3.23 (brs, 1H), 2.69 (s, 3H), 2.42 (s, 3H), 1.69 (s, 3H).

Step 11: Preparation of (R)-(4-(4-chlorophenyl)-2,3,9-trimethyl-6H-thieno[3,2-f][1,2,4]triazolo[4,3-a][1,4]diazepin-6-yl)methyl methanesulfonate (Compound 15)

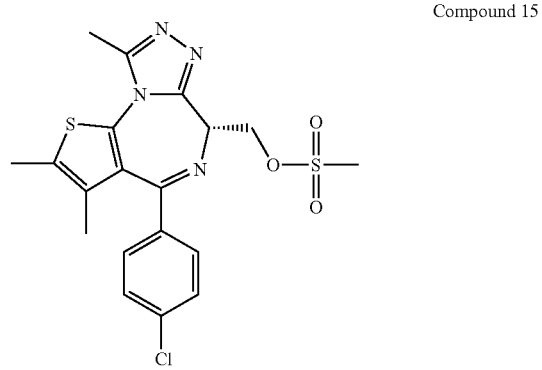

Compound 15

To a solution of (R)-(4-(4-chlorophenyl)-2,3,9-trimethyl-6H-thieno[3,2-f][1,2,4]triazolo[4,3-a][1,4]diazepin-6-yl)methanol (48.0 mg, 0.131 mmol) in DCM (1.0 mL) was added MsCl (20.4 μL, 0.261 mmol) followed by TEA (45.5 μL, 0.327 mmol) at 0° C. The reaction mixture was stirred at room temperature for 2 hours and diluted with DCM. The resulting mixture was washed with 2 N aq. HCl and saturated aq. NaHCO$_3$, dried over Na$_2$SO$_4$, filtered and concentrated in vacuo. The residue was purified by column chromatography on SiO$_2$ (EtOAc:MeOH=10:1) to obtain the title compound (46.0 mg, 78%) as a yellow solid.

$^1$H-NMR (400 MHz, CDCl$_3$): δ 7.45 (d, J=8.4 Hz, 2H), 7.36 (d, J=8.8 Hz, 2H), 5.32 (dd, J=10.4, 6.4 Hz, 1H), 5.18 (dd, J=10.4, 6.8 Hz, 1H), 4.48 (t, J=6.6 Hz, 1H), 3.21 (s, 3H), 2.69 (s, 3H), 2.43 (s, 3H), 1.71 (s, 3H).

LC-MS m/z 451.1 [M+H]$^+$, Rt=3.21 min

Example 16 to 18

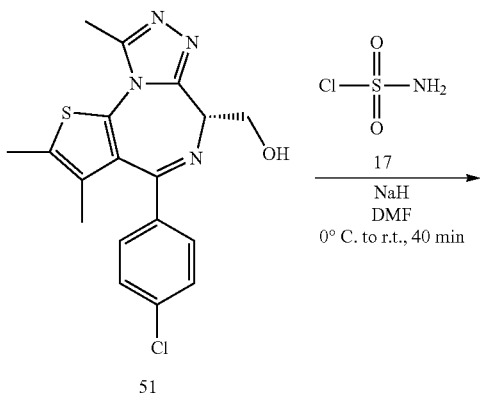

51

-continued

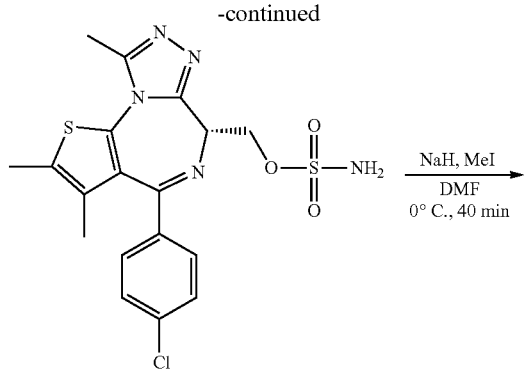
Compound 16

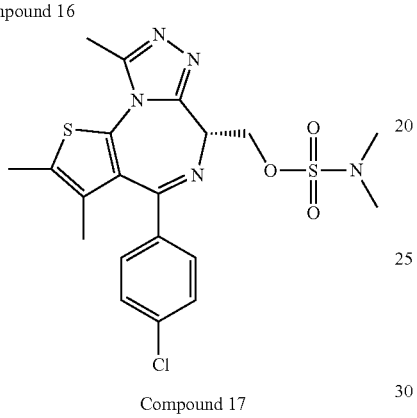
Compound 17

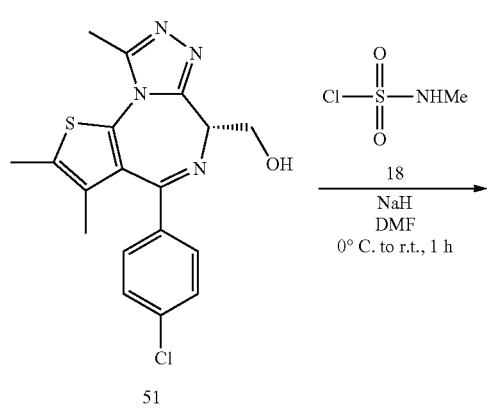
51

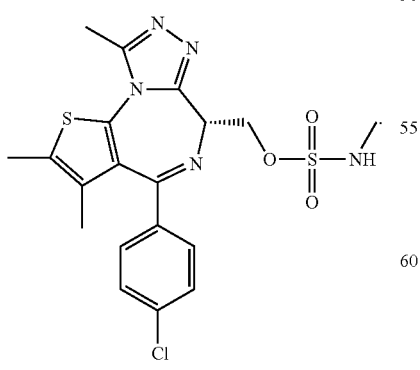
Compound 16

Example 16: Preparation of (R)-(4-(4-chlorophenyl)-2,3,9-trimethyl-6H-thieno[3,2-f][1,2,4]triazolo[4,3-a][1,4]diazepin-6-yl)methyl sulfamate (Compound 16)

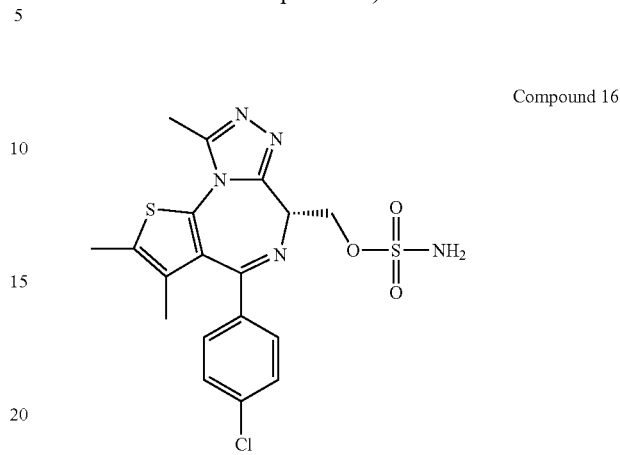
Compound 16

To a solution of (R)-(4-(4-chlorophenyl)-2,3,9-trimethyl-6H-thieno[3,2-f][1,2,4]triazolo[4,3-a][1,4]diazepin-6-yl)methanol (Intermediate 51, 85.0 mg, 0.228 mmol) in DMF (1.0 mL) was added NaH (55 wt %, 15.0 mg, 0.342 mmol) followed by sulfamoyl chloride (Intermediate 17, 342 μL, 0.684 mmol) at 0° C. The reaction mixture was stirred at room temperature for 40 min and diluted with EtOAc. The resulting mixture was washed with 2 N aq. HCl and saturated aq. NaHCO$_3$, dried over Na$_2$SO$_4$, filtered and concentrated in vacuo. The residue was purified by column chromatography on SiO$_2$ (EtOAc:MeOH=10:1) to obtain the title compound (78.0 mg, 76%) as a white solid.

$^1$H-NMR (400 MHz, CDCl$_3$): δ 7.45 (d, J=8.8 Hz, 2H), 7.36 (d, J=8.0 Hz, 2H), 5.63 (s, 2H), 5.36 (dd, J=10.4, 8 Hz, 1H), 5.05 (dd, J=10.6, 5.4 Hz, 1H), 4.47 (t, J=6.6 Hz, 1H), 2.69 (s, 3H), 2.43 (s, 3H), 1.71 (s, 3H).

LC-MS m/z 452.1 [M+H]$^+$, Rt=2.99 min.

Example 17: Preparation of (R)-(4-(4-chlorophenyl)-2,3,9-trimethyl-6H-thieno[3,2-f][1,2,4]triazolo[4,3-a][1,4]diazepin-6-yl)methyl dimethylsulfamate (Compound 17)

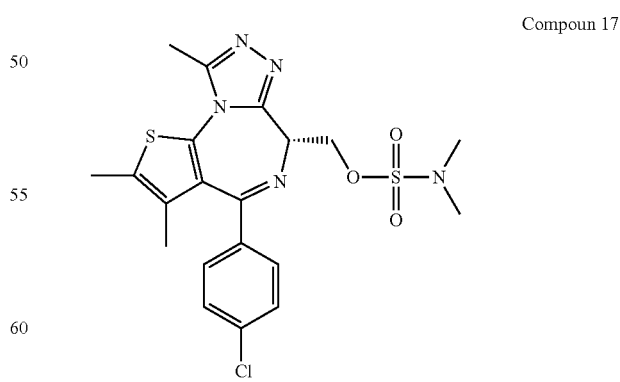
Compoun 17

To a solution of (R)-(4-(4-chlorophenyl)-2,3,9-trimethyl-6H-thieno[3,2-f][1,2,4]triazolo[4,3-a][1,4]diazepin-6-yl)methyl sulfamate (Compound 16, 58.3 mg, 0.129 mmol) in DMF (645 μL) added NaH (55 wt %, 12.4 mg, 0.284 mmol)

followed by MeI (32.3 µL, 0.516 mmol) at 0° C. The reaction mixture was stirred at 0° C. for 40 min and diluted with EtOAc. The resulting mixture was washed with 2 N aq. HCl and saturated aq. NaHCO$_3$, dried over Na$_2$SO$_4$, filtered and concentrated in vacuo. The residue was purified by prep-HPLC to obtain the title compound (31.0 mg, 50%) as a white solid.

$^1$H-NMR (400 MHz, CDCl$_3$): δ 7.45 (d, J=8.0 Hz, 2H), 7.35 (d, J=8.0 Hz, 2H), 5.25 (dd, J=10.4, 6.0 Hz, 1H), 5.12 (dd, J=9.8, 7.8 Hz, 1H), 4.49 (t, J=6.8 Hz, 1H), 3.01 (s, 6H), 2.68 (s, 3H), 2.43 (s, 3H), 1.71 (s, 3H).

LC-MS m/z 480.2 [M+H]$^+$, Rt=3.00 min.

Example 18: Preparation of (R)-(4-(4-chlorophenyl)-2,3,9-trimethyl-6H-thieno[3,2-f][1,2,4]triazolo[4,3-a][1,4]diazepin-6-yl)methyl methylsulfamate (Compound 18)

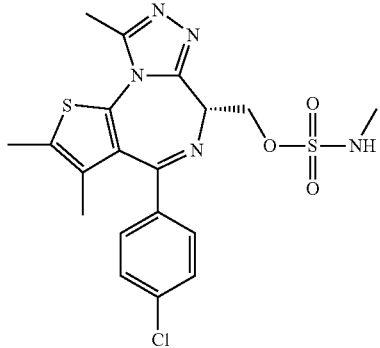

Compound 18

To a solution of (R)-(4-(4-chlorophenyl)-2,3,9-trimethyl-6H-thieno[3,2-f][1,2,4]triazolo[4,3-a][1,4]diazepin-6-yl) methanol (Intermediate 51, 20.0 mg, 0.0540 mmol) in DMF (0.27 mL) were added NaH (55 wt %, 3.51 mg, 0.0800 mmol) followed by methylsulfamoyl chloride (Intermediate 18, 9.18 µL, 0.161 mmol) at 0° C. The reaction mixture was stirred at room temperature for 1 hour and diluted with EtOAc. The resulting mixture was washed with 2 N aq. HCl and saturated aq. NaHCO$_3$, dried over Na$_2$SO$_4$, filtered and concentrated in vacuo. The residue was purified by column chromatography on SiO$_2$ (EtOAc:MeOH=10:1) to obtain the title compound (15.0 mg, 60%) as a white solid.

$^1$H-NMR (400 MHz, CDCl$_3$): δ 7.45 (d, J=8.4 Hz, 2H), 7.35 (d, J=8.4 Hz, 2H), 5.26 (dd, J=10.8, 6.4 Hz, 1H), 5.14-5.19 (m, 1H), 5.07 (dd, J=10.4, 6.8 Hz, 1H), 4.48 (t, J=6.6 Hz, 1H), 2.91 (d, J=5.6 Hz, 3H), 2.69 (s, 3H), 2.43 (s, 3H), 1.71 (s, 3H).

LC-MS m/z 466.2 [M+H]$^+$, Rt=2.98 min.

Test Example 1: Bromodomain Binding Assay (IC$_{50}$ Measurement for Inhibitors Using BRD4 Alpha-Screen)

Bromodomain binding assays were carried out in Reaction Biology (PA, USA) to test the degrees of the inventive compounds in inhibiting the human BRD4 bromodomain 1 by Alpha-screen assay method.

Recombinant human BRD4 bromodomain 1 expressed in E. coli with N-terminal His-tag was used as the enzyme target.

A synthetic peptide (SGRGACKGGACKGLGACKG-GAACKRH-GSGSK-biotin) containing 1 to 21$^{th}$ amino acids of histone H4 acetylated at lysine 5, 8, 12 and 16 and conjugated to biotin was purchased from Millipore.

BRD4-1 (44 to 170$^{th}$ amino acids; Genbank Accession # NM_058243) was expressed in E. coli with N-terminal His-tag (see, Ni-NTA spin Kit Handbook (Qiagen), second edition, January, 2008). Nickel-Chelate ALPHA acceptor beads (Perkin Elmer) were used to specifically bind BRD4-1, and ALPHA streptavidin donor beads (Perkin Elmer) were used because they specifically recognized the biotinylated H4 peptide. Binding of BRD4-1 to the synthetic peptide resulted in proximity of the donor and acceptor beads, which leads to an increase in ALPHA signal whereas in a decrease in ALPHA signal.

BRD binding assays were performed in a mixture comprising 50 mM Hepes (pH7.5), 100 mM NaCl, 0.05% CHAPS, 0.1% BSA, and 1% DMSO. After an assay reaction time of 60 min at 25° C., binding was measured with streptavidin donor beads and nickel-chelate acceptor beads. ALPHA signal was detected on Enspire (Ex/Em=680/520-620 nm). IC$_{50}$ values were calculated from the fit of the dose-response curves. All IC$_{50}$ values represent geometric mean values of a minimum of four determinations. These assays generally produced results within 3-fold of the reported mean.

The results are shown in Table 1.

Test Example 2: Anti-Proliferative Activity Test

IC$_{50}$ (uM) of the compounds obtained in Examples 1 to 18 against hematological cancer cells and solid tumors was measured for identifying anti-proliferative activities.

A human prostatic adenocarcinoma cell line, LnCAP (ATCC®, CRL-1740) and human leukemia cell line MV4-11 (ATCC®, CRL-9591) were used to test the degrees of the compounds 1 to 18 in inhibiting the cancer cell growth. The testing cell concentration was adjusted to 6.7×10$^3$ cells/ml with a culture medium supplemented with 10% FBS, in the temperature of 37° C., 5% CO$_2$ and 95% humidity. Culture media and FBS were purchased from GIBCO. 90 µL of cell suspensions thus obtained was added to two 96-well plates with the final cell density of 600 cells/well, followed by addition of 10 µL of culture medium to each well of plate. The plates were incubated overnight in a humidified incubator at 37° C. with 5% CO$_2$.

Compounds 1 to 18 were each dissolved with dimethylsulfoxide (DMSO) or phosphate buffer solution (PBS) as a stock solution, and 200× solutions of test compound (2 mM) using DMSO were prepared. Then, the DMSO solution thus obtained was diluted 20-fold with culture medium or PBS to obtain 10× working solution. 10 µL of 10× working solution (drug solution) was dispensed to each well (triplicate for each concentration). The final concentration of DMSO in culture medium was 0.5% [v/v].

Cell viability was determined using CellTiter-Glo® (CTG) assay. 100 µL of CellTiter-Glo® was added to the equal volume of the cultured cells to read luminescence in EnVision Multi Label Reader. The results are shown in Table 1.

Test Example 3: Human/Mouse Liver Microsomal Stability

Human and mouse liver microsomal clearance assays were carried out in CROWN Biosciences (Taicang, China). The human liver microsomes (Cat No. X008067, Lot No.

KQB) and mouse liver microsomes (Cat No. M1000, Lot No. 1210302) were purchased from Celsis and Xenotech, respectively.

5 μL of test compound stock solution was diluted with 495 μL of 1:1 Methanol/Water (final concentration: 100 μM, 50% MeOH) and combined with 534 μL of the respective liver microsome solution (final concentration: 1.111 μM, 0.555% MeOH). The final concentration of the liver microsome solution was 0.7 mg protein/mL.

Incubations of the liver microsome solutions were performed in a 96 well plate at 37° C. 90 μL of the liver microsome solutions were added to Blank, and 90 μL of working solution of the test compound was added to all plates except the Blank.

All plates thus obtained were warmed in water bath at 37° C. for 10 min, and 10 μL of NADPH co-factor solution comprising 42 mg of β-nicotinamide adenine dinucleotide phosphate (Sigma Cat. No. N0505 Lot 020M7009V), 84 mg of isocitric acid (Sigma Cat. No. 11252 Lot 119K1099) and 0.478 mL of isocitric dehydrogenase (Sigma Cat. No. 12002 Lot 086K7055, 15 units/mg protein, warmed in water bath at 37° C. for 5 min was added to the plates. The resulting plates were incubated at 37° C. in the following order: T60 (The test compounds were incubated with the liver microsomal solution and NADPH for 60 min at 37° C.), T30 (such as for 30 min.), and T10 (such as for 10 min.). 300 μL of a cold (4° C.) stop solution (acetonitrile (ACN) including 500 nM of tolbutamide as internal standard) and 10 μL of NADPH co-factor solution to starting plate (T0: 100% of the parent compound without any reaction) were added to the plates. The reaction was stopped by adding 300 μL of the cold (4° C.) stop solution to the other plates in the following order: T10 first, then T30 and T60.

The samples were centrifuged at 4,000 rpm for 20 min and transferred to Bioanalytical Services for liquid chromatography-mass spectrometry (LC-MS)/MS (Waters UPLC/API 4000, 10 μL injection) analysis. The results are shown in Table 1.

TABLE 1

| | TEST EXAMPLE 1 BRD4-1 binding $IC_{50}$ (μM) | TEST EXAMPLE 2 Cell proliferation $IC_{50}$ (μM) (LnCAP/MV4-11) | TEST EXAMPLE 3 Liver microsomal clearance (Human/Mouse) (μL/min/mg) |
|---|---|---|---|
| Compound 1 | 0.19 | 0.47/0.31 | 2.3/4.7 |
| Compound 2 | 0.22 | 0.60/0.41 | 1.9/8.1 |
| Compound 3 | 0.39 | 0.83/1.81 | 71.3/39.7 |
| Compound 4 | 0.42 | 0.13/0.69 | 6.3/8.9 |
| Compound 5 | 0.90 | — | — |
| Compound 6 | 1.41 | — | — |
| Compound 7 | 0.23 | 0.83/3.34 | 2.1/3.4 |
| Compound 8 | 0.22 | 0.96/1.49 | 5/5 |
| Compound 9 | 0.28 | 1.90/1.49 | 126/86 |
| Compound 10 | 0.40 | 0.57/0.35 | 29/21 |
| Compound 11 | 0.087 | 0.19/0.32 | 8.6/8.6 |
| Compound 12 | 0.11 | 44.05/1.07 | 5.6/6.9 |
| Compound 13 | 0.11 | 0.43/0.29 | 12.3/7.4 |
| Compound 14 | 0.38 | — | 8.3/6.3 |
| Compound 15 | 0.10 | 0.48/0.50 | 20/22 |
| Compound 16 | 0.25 | — | 10/9 |
| Compound 17 | 0.90 | — | 171/138 |
| Compound 18 | 0.16 | — | 51/49 |

As shown in Table 1, the compounds of Examples 1 to 18 exhibited good enzyme binding activity, and cancer cell anti-proliferative activity on LnCAP (human prostatic adenocarcinoma) and MV4-11 (human leukemia). Furthermore, said compounds were extremely stable in human and mouse liver microsomes.

Further, the anti-proliferative activities of Compounds 1 and 2 on additional cancer cell lines, i.e., OPM-2 (multiple myeloma, DSMZ®, ACC50), A375 (malignant melanoma, ATCC®, CRL-1619), SK-LU-1 (adenocarcinoma, ATCC® HTB-57™), RS4; 11 (acute lymphoblastic leukemia, ATCC® CRL-1873™), MOLM13 (acute myeloid Leukemia, DSMZ®, ACC554), HL60 (acute promyelocytic leukemia, SIBS®, TCHu23), MOLT-4 (acute lymphoblastic leukemia, SIBS®, TCHu37), Daudi (B lymphoma, ATCC® CCL-213™), MDA-MB-435 (breast, ATCC® HTB-129™), and NCI-H526 (variant small cell lung cancer, ATCC® CRL-5811™) were tested according to the method described in Test Example 2. The results were shown in Table 2.

TABLE 2

| Cell proliferation, $IC_{50}$ (uM) | Compound 1 | Compound 2 |
|---|---|---|
| OPM-2 (Multiple myeloma) | 1.45 | 0.65 |
| A375 (Malignant melanoma) | 5.57 | 9.30 |
| SKLU-1 (Adenocarcinoma) | 6.96 | 1.45 |
| RS4;11 (Acute lymphoblastic leukemia) | 3.14 | — (not determined) |
| MOLM13 (Acute myeloid Leukemia) | 1.52 | — |
| HL60 (Acute promyelocytic leukemia) | 1.24 | — |
| MOLT-4 (Acute lymphoblastic leukemia) | 2.63 | — |
| Daudi (B lymphoma) | 5.09 | — |
| MDA-MB-435 (Breast) | 5.99 | — |
| NCI-H526 (Variant small cell lung cancer) | 2.62 | — |

As shown in Table 2, Compounds 1 and 2 showed good anti-proliferative activities in solid tumor cell lines.

Test Example 4: Animal Pharmacokinetics (PK)

Pharmacokinetics of the compounds of 1, 2, 7, 8 11 and 15 were evaluated in ICR mice (6~8 weeks, 20~25 g) following intravenous (IV) administration at 10 mg/kg and per oral (PO) administration at 10 mg/kg dose level, respectively. Especially, the additional dose level of Compound 1 was 30 mg/kg.

For serum compound analysis, blood samples were collected by cardiac puncture over 24 hr time course. 20 μL of spiked plasma was added into a 96-well plate, adding ten volumes of internal standard (IS) in acetonitrile (ACN) to the obtained precipitated protein mixed thoroughly, centrifuged at 4,000 rpm for 10 min. 150 μL of supernatant thus obtained was transferred to another pre-labeled 96-well plate, mixed with 150 μL of water. 5 μL or 10 μL of the mixture was injected into the LC-MS system under the following conditions:

Column: API-4000+Waters UPLC (TCLM08);

Mobile phase: water:MeOH=100:0, 30:70, 5:95 and 100:0 (v/v %);

Flow rate: 0.45 mL/min.

Lower limit of quantification (LLOQ) was at 1 ng/mL. Pharmacokinetic parameters of half-life ($T_{1/2}$), clearance (CL), maximum plasma concentration ($C_{max}$), mean residence time (MRT) and bioavailability (F %), plasma exposure (AUC) of the compound were calculated using Phoenix WinNonlin 6.3 (non-compartmental model). The results of mouse pharmacokinetics are shown in Table 3.

TABLE 3

| Compound | Route | mpk (mg/kg) | AUC (uM · hr) | CL (mL/min/kg) | $T_{1/2}$ | MRT (hr) | F % |
|---|---|---|---|---|---|---|---|
| Compound 1 | IV | 10 | 74 | 5.1 | 2.9 | 4.7 | — |
|  | PO | 10 | 76 | — | 2.7 | 6.2 | 103.3 |
|  | IV | 30 | 302 | 3.7 | 2.7 | — | — |
|  | PO | 30 | 260 | — | 2.4 | — | 86.2 |
| Compound 2 | IV | 10 | 73 | 4.9 | 2.4 | 3.9 | — |
|  | PO | 10 | 66 | — | 2.3 | 4.1 | 89.8 |
| Compound 7 | IV | 10 | 17.3 | 22.5 | 3.6 | — | — |
|  | PO | 10 | 8.19 | — | 4.3 | — | 47.4 |
| Compound 8 | IV | 10 | 41 | 9 | 2.6 | — | — |
|  | PO | 10 | 31.5 | — | 3.2 | — | 62.3 |
| Compound 11 | IV | 10 | 20 | 16.8 | 1.3 | — | — |
|  | PO | 10 | 11.7 | — | 1.9 | — | 58.4 |
| Compound 15 | IV | 10 | 27 | 13.5 | 1.6 | 1.9 | — |
|  | PO | 10 | 31 | — | 2.5 | 2.5 | 105.4 |

As shown in Table 3, the tested compounds exhibited an excellent mouse PK, both in IV and PO routes.

Also, mouse pharmacokinetics of compound 1 is shown in FIG. 1. As shown in FIG. 1, compound 1 showed good dose linearity in plasma exposure.

Figure 2:
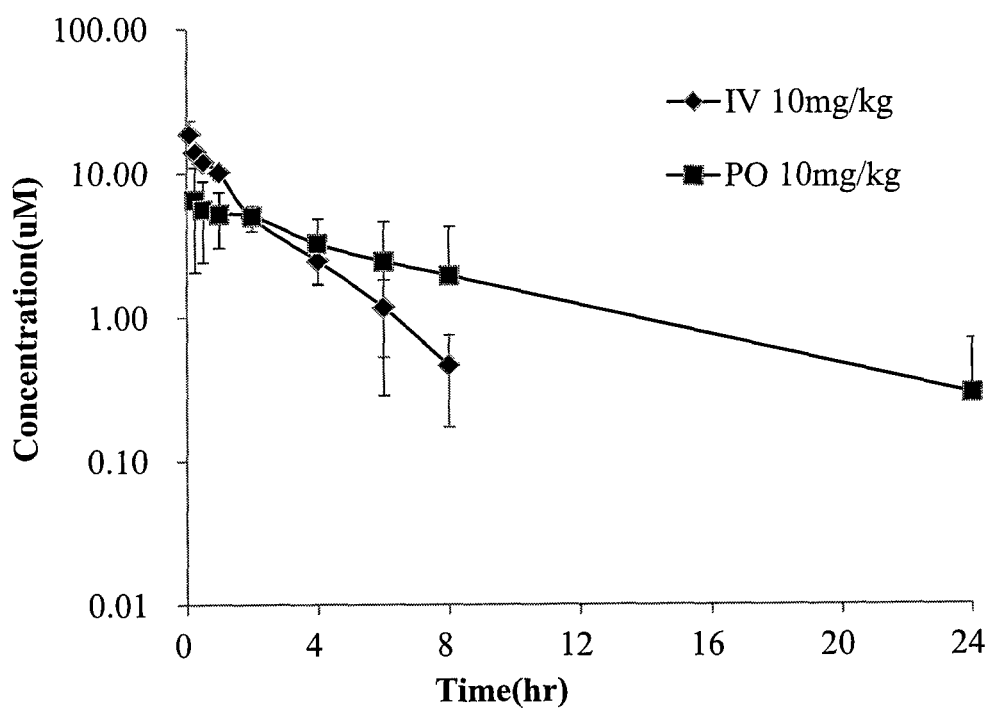
FIG. 2: Pharmacokinetics of Compound 1 in rat through PO administration route.

Also, pharmacokinetics of compound 1 was evaluated in Sprague Dawley (SD) rats following IV administration at 3 mg/kg or 10 mg/kg dose level, and PO administration at 3 mg/kg or 10 mg/kg dose level, respectively. The analytical procedures were as described in the above and the results of rat pharmacokinetics are shown in Table 4 and FIG. 2.

TABLE 4

| Compound | Route | mpk (mg/kg) | AUC (uM · hr) | CL (mL/min/kg) | T½ | MRT (hr) | F % |
|---|---|---|---|---|---|---|---|
| Compound 1 | IV | 3 | 2 | 54.8 | 0.7 | — | — |
|  | PO | 3 | 1 | — | 1.5 | — | 50.6 |
|  | IV | 10 | 15.4 | 24.9 | 1.57 | 1.86 | — |
|  | PO | 10 | 13.6 | — | 5.06 | — | 88.6 |

As shown in Table 4, Compound 1 showed excellent rat PK profiles.

Figure 3:
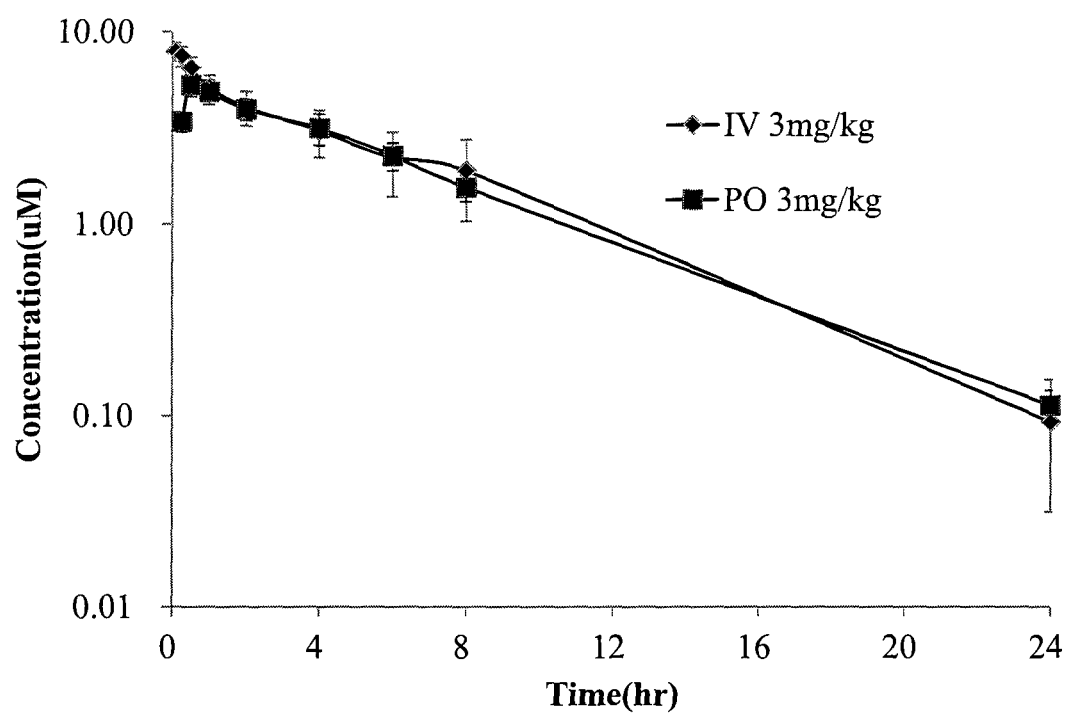
FIG. 3: Pharmacokinetics of Compound 1 in dog through PO administration route.

Further, pharmacokinetics of Compound 1 in dog was evaluated in beagle dogs following IV administration at 3 mg/kg and PO administration at 3 mg/kg dose level, respectively. The analytical procedures were as described in the above and the results of dog pharmacokinetics are shown in Table 5 and FIG. 3.

TABLE 5

| Compound | Route | mpk (mg) | AUC (uM · hr) | CL (mL/min/kg) | T½ | MRT (hr) | F % |
|---|---|---|---|---|---|---|---|
| Compound 1 | IV | 3 | 19.7 | 5.6 | 3.86 | 4.9 | — |
|  | PO | 3 | 17.3 | — | 4.2 | — | 92.3 |

Dog PK data of Compound 1 was an excellent plasma exposure in IV and PO, and it shows high bioavailability (%).

Test Example 5: Efficacy of Compound 1 in MV4-11 Human Leukemia Model Mouse Xenograft Tumor growth inhibition (TGI) activities of compound 1 were tested in MV4-11 human leukemia mouse xenograft. Tumor growth inhibitions were observed in in vivo subcutaneous mouse xenograft model (MV4-11 cell line, ATCC®, CRL-9591). A total of 48 NOD/SCID female mice of 6-8 weeks age and weighing approximately 18 to 22 g, purchased from HFK (Beijing HFK Bio-Technology Co. Ltd.), were used for tumor inoculation.

The MV4-11 cell line was maintained in vitro in IMDM (Iscove's modified Dulbecco's media) supplemented with 10% fetal bovine serum at 37° C. in an atmosphere of 5% $CO_2$ in air. The tumor cells were routinely subcultured twice weekly by trypsin-EDTA treatment. The cells growing in an exponential growth phase were harvested and counted for tumor inoculation. The treatments were started when the tumor size reached approximately 150-200 mm$^3$.

Each mouse was inoculated subcutaneously at the right flank with MV4-11 tumor cells ($1\times10^7$ cells) in mixture of 100 ul PBS and 100 ul of Matrigel™ for tumor development. A total of 48 mice were used for each group. The amounts of treated compounds are represented in milligram (mg) of compound per kilogram (kg) of animal body weight (mg/kg, mpk). Administration route of the test compound was PO (oral) injection. Three groups, i.e., vehicle group (Control group), 50 mpk group (treatment at 50 mpk of compound 1 through PO injection) and 100 mpk group (treatment at 100 mpk of compound 1 through PO injection) of mice were used. The overall administration schedule was 2 cycles of treatment for 5 days (5 d ON), followed by 2 days of non-treatment (2 d OFF).

Tumor sizes were measured using a caliper, once every 4 days, and the tumor volume was expressed in mm³ using Equation 1:

$$V = 0.5 a \times b^2 \quad \text{[Equation 1]}$$

wherein, a and b are the long and short diameters of the tumor, respectively.

Figure 4:
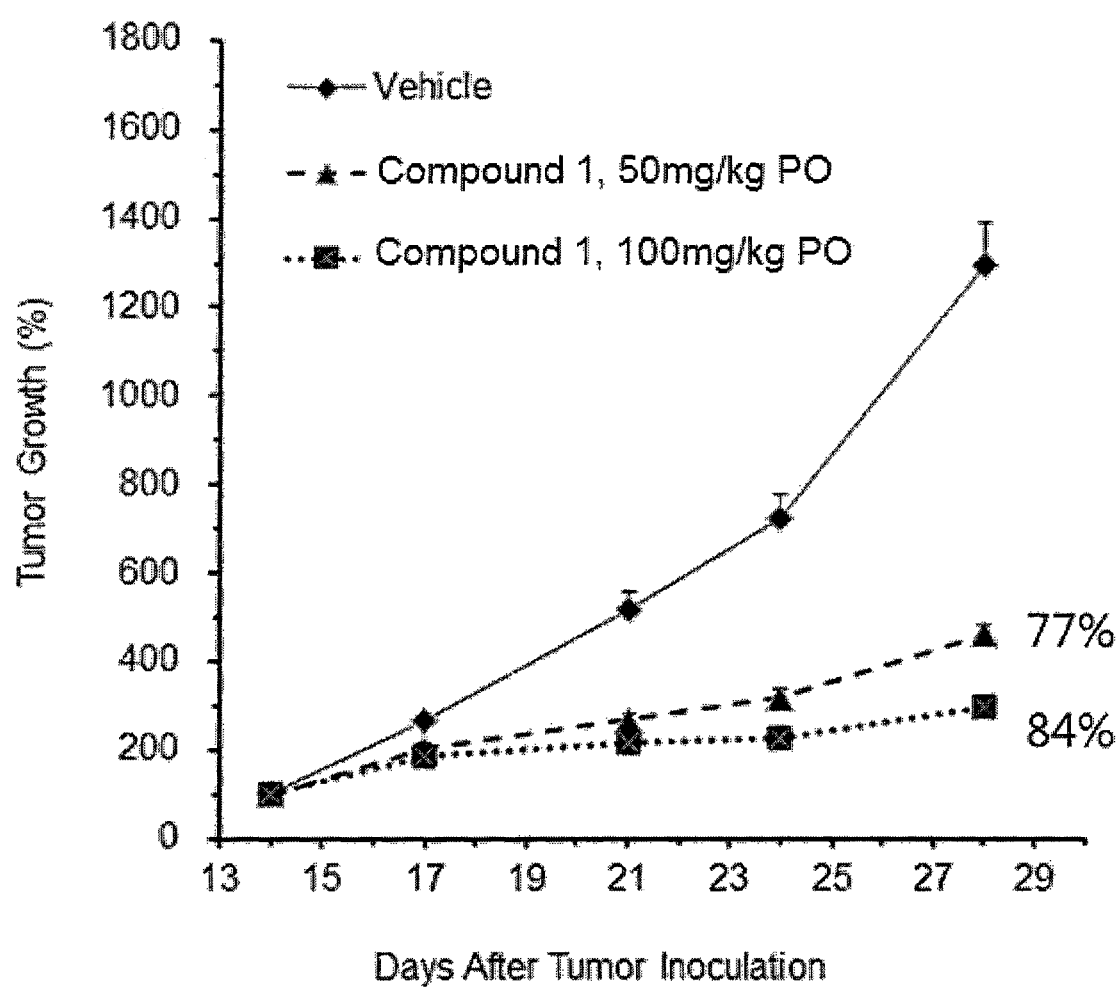
FIG. 4: Tumor growth inhibition (TGI) activities of Compound 1 in MV4-11 human leukemia xenograft.

The tumor growth inhibition (% TGI) results of the three groups are shown in FIG. 4. Also, the body weight change (% BW change) compared to that of vehicle were shown in Table 6.

TABLE 6

| Sample | Route | Administration schedule (14 days) | % TGI | % BW change |
|---|---|---|---|---|
| Vehicle | PO | 5 d ON/2 d Off × 2 | 0 | >5% |
| Compound 1 | 50 mpk, PO | 5 d ON/2 d Off × 2 | 77 | >5% |
|  | 100 mpk, PO | 5 d ON/2 d Off × 2 | 84 | >5% |

As shown in FIG. 4 and Table 6, Compound 1 showed 84% (% TGI) at 100 mpk and 77% at 50 mpk compared to that of vehicle (0%). Also, the BW change (%) was very low.

What is claimed is:

1. A compound of formula (I), or a pharmaceutically acceptable salt, a hydrate, a solvate, or an isomer thereof:

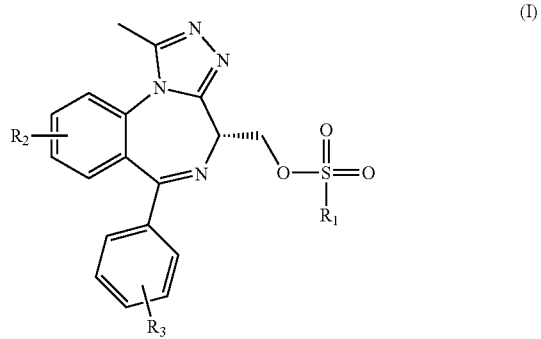

(I)

wherein, $R_1$ is selected from the group consisting of $C_{1-10}$ alkyl, $C_{3-10}$ cycloalkyl, $C_{3-10}$ cycloalkyl$C_{1-10}$ alkyl, $C_{1-10}$ alkyl$C_{3-10}$ cycloalkyl, halo$C_{1-10}$ alkyl, $C_{2-10}$ alkenyl, and NRbRb', wherein, Rb, and Rb' are each independently selected from the group consisting of hydrogen, $C_{1-10}$ alkyl, $C_{1-10}$ alkylaryl, $C_{3-10}$ cycloalkyl, $C_{3-10}$ cycloalkyl$C_{1-10}$ alkyl, $C_{1-10}$ alkylcycloalkyl, formyl, heterocyclyl, heterocyclylalkyl, halo$C_{1-10}$ alkyl, heteroaryl, aralkyl, heteroaryl$C_{1-10}$ alkyl, heteroarylaryl, fused bicyclyl, biaryl, aryloxyaryl, heteroaryloxyaryl, aryloxyheteroaryl, heteroaryloxyheteroaryl, $C_{2-10}$ alkenyl, $C_{2-10}$ alkynyl, azido, nitro and cyano;

$R_2$ is selected from the group consisting of halo, halo $C_{1-6}$ alkyl, $C_{1-6}$ alkoxy, halo $C_{1-6}$ alkoxy, cyano, $CF_3$, —$OCF_3$, —CONHRd, and heteroaromatic groups selected from the group consisting of:

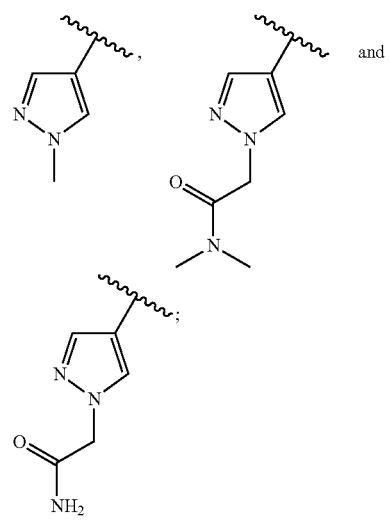

$R_3$ is selected from the group consisting of hydrogen, hydroxyl, halo, $C_{1-6}$ alkyl, halo $C_{1-6}$ alkyl, $C_{1-6}$ alkoxy, halo $C_{1-6}$ alkoxy, nitro, cyano, $CF_3$, —$OCF_3$, —CORd and —CONHRd; and Rd is $C_{1-3}$ alkyl or hydroxy $C_{1-3}$ alkyl.

2. The compound of claim 1, wherein $R_1$ is $C_{1-6}$ alkyl, $C_{3-10}$ cycloalkyl, or NRbRb', wherein Rb and Rb' are each independently hydrogen or $C_{1-6}$ alkyl; and $R_2$ is, $C_{1-6}$ alkoxy, —CONHRd or heteroaromatic groups selected from the group consisting of:

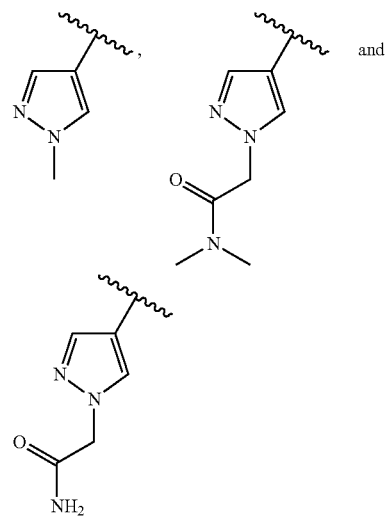

$R_3$ is halo; and

Rd is $C_{1-3}$ alkyl or hydroxy $C_{1-3}$ alkyl.

3. The compound of claim 1, which is selected from the group consisting of:

(R)-(6-(4-chlorophenyl)-8-methoxy-1-methyl-4H-benzo[f][1,2,4]triazolo[4,3-a][1,4]diazepin-4-yl)methyl methanesulfonate;

(R)-(6-(4-chlorophenyl)-8-methoxy-1-methyl-4H-benzo[f][1,2,4]triazolo[4,3-a][1,4]diazepin-4-yl)methyl ethanesulfonate;

(R)-(6-(4-chlorophenyl)-8-methoxy-1-methyl-4H-benzo[f][1,2,4]triazolo[4,3-a][1,4]diazepin-4-yl)methyl propane-1-sulfonate;

(R)-(6-(4-chlorophenyl)-1-methyl-4H-benzo[f][1,2,4]triazolo[4,3-a][1,4]diazepin-4-yl)methyl methanesulfonate;

(R)-(6-(4-cyanophenyl)-8-methoxy-1-methyl-4H-benzo[f][1,2,4]triazolo[4,3-a][1,4]diazepin-4-yl)methyl methanesulfonate;

(R)-(6-(4-chlorophenyl)-8-methoxy-1-methyl-4H-benzo[f][1,2,4]triazolo[4,3-a][1,4]diazepin-4-yl)methyl sulfamate;

(R)-(6-(4-chlorophenyl)-8-methoxy-1-methyl-4H-benzo[f][1,2,4]triazolo[4,3-a][1,4]diazepin-4-yl)methyl dimethylsulfamate;

(R)-(6-(4-chlorophenyl)-8-methoxy-1-methyl-4H-benzo[f][1,2,4]triazolo[4,3-a][1,4]diazepin-4-yl)methyl methylsulfamate;

(R)-(6-(4-chlorophenyl)-1-methyl-8-(1-methyl-1H-pyrazol-4-yl)-4H-benzo[f][1,2,4]triazolo[4,3-a][1,4]diazepin-4-yl)methyl methanesulfonate;

(R)-(8-(1-(2-amino-2-oxoethyl)-1H-pyrazol-4-yl)-6-(4-chlorophenyl)-1-methyl-4H-benzo[f][1,2,4]triazolo[4,3-a][1,4]diazepin-4-yl)methyl methanesulfonate;

(R)-(6-(4-chlorophenyl)-8-(1-(2-(dimethylamino)-2-oxoethyl)-1H-pyrazol-4-yl)-1-methyl-4H-benzo[f][1,2,4]triazolo[4,3-a][1,4]diazepin-4-yl)methyl methanesulfonate; and (R)-(6-(4-chlorophenyl)-8-((2-hydroxyethyl)carbamoyl)-1-methyl-4H-benzo[f][1,2,4]triazolo[4,3-a][1,4]diazepin-4-yl)methyl methanesulfonate.

4. The compound of claim 1, which is selected from the group consisting of:

(R)-(6-(4-chlorophenyl)-8-methoxy-1-methyl-4H-benzo[f][1,2,4]triazolo[4,3-a][1,4]diazepin-4-yl)methyl methanesulfonate;

(R)-(6-(4-chlorophenyl)-8-methoxy-1-methyl-4H-benzo[f][1,2,4]triazolo[4,3-a][1,4]diazepin-4-yl)methyl ethanesulfonate;

(R)-(6-(4-cyanophenyl)-8-methoxy-1-methyl-4H-benzo[f][1,2,4]triazolo[4,3-a][1,4]diazepin-4-yl)methyl methanesulfonate;

(R)-(6-(4-chlorophenyl)-8-methoxy-1-methyl-4H-benzo[f][1,2,4]triazolo[4,3-a][1,4]diazepin-4-yl)methyl sulfamate; and (R)-(6-(4-chlorophenyl)-1-methyl-8-(1-methyl-1H-pyrazol-4-yl)-4H-benzo[f][1,2,4]triazolo[4,3-a][1,4]diazepin-4-yl)methyl methanesulfonate.

5. The compound of claim 1, which is (R)-(6-(4-chlorophenyl)-8-methoxy-1-methyl-4H-benzo[f][1,2,4]triazolo[4,3-a][1,4]diazepin-4-yl)methyl methanesulfonate.

6. A pharmaceutical composition comprising the compound of claim 1 or a pharmaceutically acceptable salt, a hydrate, a solvate or an isomer thereof, and a pharmaceutically acceptable carrier.

7. The pharmaceutical composition of claim 6, wherein the pharmaceutically acceptable carrier is selected from the group consisting of a binder, a filler, an excipient, a disintegrating agent, a lubricant and a flavoring agent.

8. The pharmaceutical composition of claim 6, which further comprises at least one chemotherapeutic agent.

* * * * *